US012630880B2

(12) United States Patent
Sakamoto et al.

(10) Patent No.: US 12,630,880 B2
(45) Date of Patent: May 19, 2026

(54) METHOD FOR PREDICTING SENSITIVITY OF CANCER CELL TO HELICASE INHIBITOR

(71) Applicant: Chugai Seiyaku Kabushiki Kaisha, Tokyo (JP)

(72) Inventors: Hiroshi Sakamoto, Kanagawa (JP); Kenji Kashima, Kanagawa (JP); Kiyomoto Ogasawara, Kanagawa (JP); Yuki Ohte, Kanagawa (JP); Mayumi Soga, Kanagawa (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 989 days.

(21) Appl. No.: 17/777,135

(22) PCT Filed: Nov. 20, 2020

(86) PCT No.: PCT/JP2020/043487
§ 371 (c)(1),
(2) Date: May 16, 2022

(87) PCT Pub. No.: WO2021/100869
PCT Pub. Date: May 27, 2021

(65) Prior Publication Data
US 2022/0389516 A1 Dec. 8, 2022

(30) Foreign Application Priority Data
Nov. 21, 2019 (JP) ................................. 2019-210304

(51) Int. Cl.
*C07H 21/04* (2006.01)
*C12Q 1/6886* (2018.01)
(52) U.S. Cl.
CPC ..... *C12Q 1/6886* (2013.01); *C12Q 2600/106* (2013.01); *C12Q 2600/156* (2013.01)
(58) Field of Classification Search
CPC .................................................. C12Q 1/6886
See application file for complete search history.

(56) References Cited

PUBLICATIONS

Heikkinen et al. (Carcinogenesis vol. 27 No. 8 pp. 1593-1599, 2006).*
Shamanna et al. (Oncotarget, vol. 7, No. 12, 13269-13284).*
Wang et al. (Nature Genetics, 37, 7, 2005, 750-755).*
Elbashir et al. (The EMBO Journal, vol. 20, No. 23, pp. 6877-6888, 2001).*
Fujita et al. (Int. J. Mol. Sci. 2015, 16, 5254-5270).*
Maga et al. (Biochemistry 2005, 44, 9637-9644).*
Datta et al., "New Insights Into DNA Helicases as Druggable Targets for Cancer Therapy," Front Mol Biosci, Jun. 26, 2018, vol. 5, Article 59, 22 pages.
Fan et al., "RAD50 germline mutations are associated with poor survival in BRCA1/2-negative breast cancer patients," Int J Cancer, Oct. 15, 2018, 143(8):1935-1942. doi: 10.1002/ijc.31579. Epub Jul. 26, 2018.
Havrysh et al., "Silencing of the RAD50 gene contributes to enhancing the sensitivity of the triple-negative breast cancer cells to carboplatin," Cancer Res, Jul. 1, 2019, 79(13 Supplement):4927, 2 pages.
Monnat, "Human RECQ helicases: Roles in DNA metabolism, mutagenesis and cancer biology," Seminars in Cancer Biology, Oct. 2010, 20(5):329-339.
Behan et al., "Prioritisation of cancer therapeutic targets using CRISPR-Cas9 screens," Nature, Apr. 2019, 568(7753):511-516.
Camidge et al., "Updated Efficacy and Safety Data and Impact of the EML4-ALK Fusion Variant on the Efficacy of Alectinib in Untreated ALK-Positive Advanced Non-Small Cell Lung Cancer in the Global Phase III Alex Study," J Thorac Oncol, Jul. 2019, 14(7):1233-1243.
Chan et al., "WRN helicase is a synthetic lethal target in microsatellite unstable cancers," Nature, Apr. 25, 2019, 568(7753):551-556.
Chapman et al., "Improved Survival with Vemurafenib in Melanoma with Braf V600E Mutation," NEJM, Jun. 30, 2011, 364(26):2507-2516.
Cheng et al., "Targeting Werner syndrome protein sensitizes U-2 Os osteosarcoma cells to selenium-induced DNA damage response and necrotic death," Biochemical and Biophysical Research Communications, Mar. 30, 2012, 420:24-28.
Jia et al., "Role of human DNA2 (hDNA2) as a potential target for cancer and other diseases: A systematic review," DNA Repair, Nov. 2017, 59:9-19.
Kategaya et al., "Werner Syndrome Helicase is Required for the Survival of Cancer Cells with Microsatellite Instability," iScience, Mar. 29, 2019, 13:488-497.
Lieb et al., "Werner syndrome helicase is a selective vulnerability of microsatellite instability-high tumor cells," eLife, Mar. 25, 2019, 8:e43333, 22 pages. doi: https://doi.org/10.7554/eLife.4333.
Maemondo et al., "Gefitinib or Chemotherapy for Non-Small-Cell Lung Cancer with Mutated EGFR," NEJM, Jun. 24, 2010, 362(25):2380-2388.
Meiss et al., "Clinicopathologic characterization of breast carcinomas in patients with non-BRCA germline mutations: results from a single institution's high-risk population," Human Pathology, Dec. 2018, 82:20-31.
Moore et al., "Maintenance Olaparib in Patients with Newly Diagnosed Advanced Ovarian Cancer," NEJM, Dec. 2, 20187, 379(26):2495-2505.

(Continued)

*Primary Examiner* — Amy Rose Hudson
(74) *Attorney, Agent, or Firm* — Fish & Richardson P.C.

(57) ABSTRACT

Provided is a method for predicting sensitivity of a cancer cell to a helicase inhibitor, the method comprising the step of:

predicting a cancer cell having at least one mutation detected selected from the first group consisting of TTK mutation and RAD 50 mutation, as having sensitivity to a helicase inhibitor, or predicting a cancer cell having at least one mutation detected selected from the second group consisting of RAD 50 mutation, MRE 11 mutation, NBN mutation, DNA 2 mutation and RBBP 8 mutation, as having sensitivity to a helicase inhibitor.

2 Claims, 3 Drawing Sheets

Specification includes a Sequence Listing.

(56)                References Cited

PUBLICATIONS

Uchizaka, "MRE11 point mutation from two brothers with lung cancer," The Japanese Society of Pediatric Hematology, Proceedings of the Annual Meeting and the Public Symposium Program of the Society for the Purpose of Protecting Children with Oncology, 2009, 1 page (non-official translation).

Wessendorf et al., "Deficiency of the DNA repair protein nibrin increases the basal but not the radiation induced mutation frequency in vivo," Mutat Res, Nov. 2014, 769:11-16.

International Search Report in PCT/JP2020/043487, mailed Dec. 15, 2020, 2 pages.

Van Wietmarschen et al., "Repeat expansions confer WRN dependence in microsatellite-unstable cancers," Nature, Oct. 2020, 586(7828):292-298. doi:10.1038/s41586-020-2769-8, including online content (37 pages).

English translation of International Preliminary Report on Patentability for Appn. Ser. No. PCT/JP2020/043487, dated Jun. 2, 2022, 5 pages.

Aggarwal et al., "Inhibition of helicase activity by a small molecule impairs Werner syndrome helicase (WRN) function in the cellular response to DNA damage or replication stress," Proc Natl Acad Sci USA, Jan. 2, 20115, 108(4):1525-1530, and 8 pages of supplemental information, 14 pages total.

Aggarwal et al., "Werner Syndrome Helicase Has a Critical Role in DNA Damage Responses in the Absence of a Functional Fanconi Anemia Pathway," Cancer Res, Sep. 1, 2013, 73(17):5497-5507, and 25 pages of supplemental information, 36 pages total.

Sommers et al., "A high-throughput screen to identify novel small molecule inhibitors of the Werner Syndrome Helicase-Nuclease (WRN)," PLoS One, Jan. 9, 2019, 14(1):e0210525, https://doi.org/10.1371/journal.pone.0210525, and supplemental information, 42 pages total.

* cited by examiner

SEQUENCE LISTING

```
<160> NUMBER OF SEQ ID NOS: 30

<210> SEQ ID NO 1
<211> LENGTH: 3000
<212> TYPE: DNA
<213> ORGANISM: Homo sapiens

<400> SEQUENCE: 1
atgagtgaaa aaaaattgga aacaactgca cagcagcgga aatgtcctga atggatgaat      60
gtgcagaata aaagatgtgc tgtagaagaa agaaaggcat gtgttcggaa gagtgttttt     120
gaagatgacc tccccttctt agaattcact ggatccattg tgtatagtta cgatgctagt     180
gattgctctt tcctgtcaga agatattagc atgagtctat cagatgggga tgtggtggga     240
tttgacatgg agtggccacc attatacaat agagggaaac ttggcaaagt tgcactaatt     300
cagttgtgtg tttctgagag caaatgttac ttgttccacg tttcttccat gtcagttttt     360
ccccagggat taaaaatgtt gcttgaaaat aaagcagtta aaaaggcagg tgtaggaatt     420
gaaggagatc agtggaaact tctacgtgac tttgatatca aattgaagaa ttttgtggag     480
ttgacagatg ttgccaataa aaagctgaaa tgcacagaga cctggagcct taacagtctg     540
gttaaacacc tcttaggtaa acagctcctg aaagacaagt ctatccgctg tagcaattgg     600
agtaaatttc ctctcactga ggaccagaaa ctgtatgcag ccactgatgc ttatgctggt     660
tttattattt accgaaattt agagattttg gatgatactg tgcaaaggtt tgctataaat     720
aaagaggaag aaatcctact tagcgacatg aacaaacagt tgacttcaat ctctgaggaa     780
```

-continued

```
gtgatggatc tggctaagca tcttcctcat gctttcagta aattggaaaa cccacggagg        840
gtttctatct tactaaagga tatttcagaa aatctatatt cactgaggag gatgataatt        900
gggtctacta acattgagac tgaactgagg cccagcaata atttaaactt attatccttt        960
gaagattcaa ctactggggg agtacaacag aaacaaatta gagaacatga agttttaatt       1020
cacgttgaag atgaaacatg ggacccaaca cttgatcatt tagctaaaca tgatggagaa       1080
gatgtacttg gaaataaagt ggaacgaaaa gaagatggat ttgaagatgg agtagaagac       1140
aacaaattga agagaatat ggaaagagct tgtttgatgt cgttagatat tacagaacat        1200
gaactccaaa ttttggaaca gcagtctcag gaagaatatc ttagtgatat tgcttataaa       1260
tctactgagc atttatctcc caatgataat gaaaacgata cgtcctatgt aattgagagt       1320
gatgaagatt tagaaatgga gatgcttaag catttatctc ccaatgataa tgaaaacgat       1380
acgtcctatg taattgagag tgatgaagat ttagaaatgg agatgcttaa gtctttagaa       1440
aacctcaata gtggcacggt agaaccaact cattctaaat gcttaaaaat ggaaagaaat       1500
ctgggtcttc ctactaaaga agaagaagaa gatgatgaaa atgaagctaa tgaaggggaa       1560
gaagatgatg ataaggactt tttgtggcca gcacccaatg aagagcaagt tacttgcctc       1620
aagatgtact ttggccattc cagttttaaa ccagttcagt ggaaagtgat tcattcagta       1680
ttagaagaaa aagagataa tgttgctgtc atggcaactg gatatggaaa gagtttgtgc       1740
ttccagtatc cacctgttta tgtaggcaag attggccttg ttatctctcc ccttatttct       1800
ctgatggaag accaagtgct acagcttaaa atgtccaaca tcccagcttg cttccttgga       1860
tcagcacagt cagaaaatgt tctaacagat attaaattag gtaaataccg gattgtatac       1920
gtaactccag aatactgttc aggtaacatg ggcctgctcc agcaacttga ggctgatatt       1980
ggtatcacgc tcattgctgt ggatgaggct cactgtattt ctgagtgggg gcatgatttt       2040
agggattcat tcaggaagtt gggctcccta aagacagcac tgccaatggt tccaatcgtt       2100
gcacttactg ctactgcaag ttcttcaatc cgggaagaca ttgtacgttg cttaaatctg       2160
agaaatcctc agatcacctg tactggtttt gatcgaccaa acctgtattt agaagttagg       2220
cgaaaaacag ggaatatcct tcaggatctg cagccatttc ttgtcaaaac aagttcccac       2280
tgggaatttg aaggtccaac aatcatctac tgtccttcta gaaaaatgac acaacaagtt       2340
acaggtgaac ttaggaaact gaatctatcc tgtggaacat accatgcggg catgagtttt       2400
agcacaagga aagacattca tcataggttt gtaagagatg aaattcagtg tgtcatagct       2460
accatagctt ttggaatggg cattaataaa gctgacattc gccaagtcat tcattacggt       2520
gctcctaagg acatggaatc atattatcag gagattggta gagctggtcg tgatggactt       2580
caaagttctt gtcacgtcct ctgggctcct gcagacatta acttaaatag gcaccttctt       2640
actgagatac gtaatgagaa gtttcgatta tacaaattaa agatgatggc aaagatggaa       2700
aaatatcttc attctagcag atgtaggaga caaatcatct gtctcatttt gaggacaaa       2760 caagtacaaa aagcctcctt gggaattatg ggaactgaaa atgctgtga taattgcagg       2820 tccagattgg atcattgcta ttccatggat gactcagagg atacatcctg ggactttggt       2880
ccacaagcat ttaagctttt gtctgctgtg gacatcttag cgaaaaatt tggaattggg       2940 cttccaattt tatttctccg aggatctaat tctcagcgtc ttgccgatca atatcgcagg       3000
```

```
<210> SEQ ID NO 2
<211> LENGTH: 1432
<212> TYPE: PRT
```

```
<213> ORGANISM: Homo sapiens

<400> SEQUENCE: 2

Met Ser Glu Lys Lys Leu Glu Thr Thr Ala Gln Gln Arg Lys Cys Pro
1               5                   10                  15

Glu Trp Met Asn Val Gln Asn Lys Arg Cys Ala Val Glu Glu Arg Lys
                20                  25                  30

Ala Cys Val Arg Lys Ser Val Phe Glu Asp Asp Leu Pro Phe Leu Glu
            35                  40                  45

Phe Thr Gly Ser Ile Val Tyr Ser Tyr Asp Ala Ser Asp Cys Ser Phe
        50                  55                  60

Leu Ser Glu Asp Ile Ser Met Ser Leu Ser Asp Gly Asp Val Val Gly
65                  70                  75                  80

Phe Asp Met Glu Trp Pro Pro Leu Tyr Asn Arg Gly Lys Leu Gly Lys
                85                  90                  95

Val Ala Leu Ile Gln Leu Cys Val Ser Glu Ser Lys Cys Tyr Leu Phe
                100                 105                 110

His Val Ser Ser Met Ser Val Phe Pro Gln Gly Leu Lys Met Leu Leu
            115                 120                 125

Glu Asn Lys Ala Val Lys Lys Ala Gly Val Gly Ile Glu Gly Asp Gln
    130                 135                 140

Trp Lys Leu Leu Arg Asp Phe Asp Ile Lys Leu Lys Asn Phe Val Glu
145                 150                 155                 160

Leu Thr Asp Val Ala Asn Lys Lys Leu Lys Cys Thr Glu Thr Trp Ser
                165                 170                 175

Leu Asn Ser Leu Val Lys His Leu Leu Gly Lys Gln Leu Leu Lys Asp
            180                 185                 190

Lys Ser Ile Arg Cys Ser Asn Trp Ser Lys Phe Pro Leu Thr Glu Asp
        195                 200                 205

Gln Lys Leu Tyr Ala Ala Thr Asp Ala Tyr Ala Gly Phe Ile Ile Tyr
    210                 215                 220

Arg Asn Leu Glu Ile Leu Asp Asp Thr Val Gln Arg Phe Ala Ile Asn
225                 230                 235                 240

Lys Glu Glu Glu Ile Leu Leu Ser Asp Met Asn Lys Gln Leu Thr Ser
                245                 250                 255

Ile Ser Glu Glu Val Met Asp Leu Ala Lys His Leu Pro His Ala Phe
                260                 265                 270

Ser Lys Leu Glu Asn Pro Arg Arg Val Ser Ile Leu Leu Lys Asp Ile
    275                 280                 285

Ser Glu Asn Leu Tyr Ser Leu Arg Arg Met Ile Ile Gly Ser Thr Asn
    290                 295                 300

Ile Glu Thr Glu Leu Arg Pro Ser Asn Asn Leu Asn Leu Leu Ser Phe
305                 310                 315                 320

Glu Asp Ser Thr Thr Gly Gly Val Gln Gln Lys Gln Ile Arg Glu His
                325                 330                 335

Glu Val Leu Ile His Val Glu Asp Glu Thr Trp Asp Pro Thr Leu Asp
            340                 345                 350

His Leu Ala Lys His Asp Gly Glu Asp Val Leu Gly Asn Lys Val Glu
        355                 360                 365

Arg Lys Glu Asp Gly Phe Glu Asp Gly Val Glu Asp Asn Lys Leu Lys
    370                 375                 380

Glu Asn Met Glu Arg Ala Cys Leu Met Ser Leu Asp Ile Thr Glu His
385                 390                 395                 400
```

```
Glu Leu Gln Ile Leu Glu Gln Gln Ser Gln Glu Glu Tyr Leu Ser Asp
                405             410             415

Ile Ala Tyr Lys Ser Thr Glu His Leu Ser Pro Asn Asp Asn Glu Asn
            420             425             430

Asp Thr Ser Tyr Val Ile Glu Ser Asp Glu Asp Leu Glu Met Glu Met
            435             440             445

Leu Lys His Leu Ser Pro Asn Asp Asn Glu Asn Asp Thr Ser Tyr Val
        450             455             460

Ile Glu Ser Asp Glu Asp Leu Glu Met Glu Met Leu Lys Ser Leu Glu
465             470             475             480

Asn Leu Asn Ser Gly Thr Val Glu Pro Thr His Ser Lys Cys Leu Lys
            485             490             495

Met Glu Arg Asn Leu Gly Leu Pro Thr Lys Glu Glu Glu Glu Asp Asp
            500             505             510

Glu Asn Glu Ala Asn Glu Gly Glu Glu Asp Asp Asp Lys Asp Phe Leu
            515             520             525

Trp Pro Ala Pro Asn Glu Glu Gln Val Thr Cys Leu Lys Met Tyr Phe
        530             535             540

Gly His Ser Ser Phe Lys Pro Val Gln Trp Lys Val Ile His Ser Val
545             550             555             560

Leu Glu Glu Arg Arg Asp Asn Val Ala Val Met Ala Thr Gly Tyr Gly
            565             570             575

Lys Ser Leu Cys Phe Gln Tyr Pro Pro Val Tyr Val Gly Lys Ile Gly
            580             585             590

Leu Val Ile Ser Pro Leu Ile Ser Leu Met Glu Asp Gln Val Leu Gln
            595             600             605

Leu Lys Met Ser Asn Ile Pro Ala Cys Phe Leu Gly Ser Ala Gln Ser
        610             615             620

Glu Asn Val Leu Thr Asp Ile Lys Leu Gly Lys Tyr Arg Ile Val Tyr
625             630             635             640

Val Thr Pro Glu Tyr Cys Ser Gly Asn Met Gly Leu Leu Gln Gln Leu
            645             650             655

Glu Ala Asp Ile Gly Ile Thr Leu Ile Ala Val Asp Glu Ala His Cys
            660             665             670

Ile Ser Glu Trp Gly His Asp Phe Arg Asp Ser Phe Arg Lys Leu Gly
            675             680             685

Ser Leu Lys Thr Ala Leu Pro Met Val Pro Ile Val Ala Leu Thr Ala
        690             695             700

Thr Ala Ser Ser Ser Ile Arg Glu Asp Ile Val Arg Cys Leu Asn Leu
705             710             715             720

Arg Asn Pro Gln Ile Thr Cys Thr Gly Phe Asp Arg Pro Asn Leu Tyr
            725             730             735

Leu Glu Val Arg Arg Lys Thr Gly Asn Ile Leu Gln Asp Leu Gln Pro
            740             745             750

Phe Leu Val Lys Thr Ser Ser His Trp Glu Phe Glu Gly Pro Thr Ile
            755             760             765

Ile Tyr Cys Pro Ser Arg Lys Met Thr Gln Gln Val Thr Gly Glu Leu
        770             775             780

Arg Lys Leu Asn Leu Ser Cys Gly Thr Tyr His Ala Gly Met Ser Phe
785             790             795             800

Ser Thr Arg Lys Asp Ile His His Arg Phe Val Arg Asp Glu Ile Gln
            805             810             815

Cys Val Ile Ala Thr Ile Ala Phe Gly Met Gly Ile Asn Lys Ala Asp
```

-continued

```
            820             825             830
Ile Arg Gln Val Ile His Tyr Gly Ala Pro Lys Asp Met Glu Ser Tyr
        835             840             845

Tyr Gln Glu Ile Gly Arg Ala Gly Arg Asp Gly Leu Gln Ser Ser Cys
    850             855             860

His Val Leu Trp Ala Pro Ala Asp Ile Asn Leu Asn Arg His Leu Leu
865             870             875             880

Thr Glu Ile Arg Asn Glu Lys Phe Arg Leu Tyr Lys Leu Lys Met Met
            885             890             895

Ala Lys Met Glu Lys Tyr Leu His Ser Ser Arg Cys Arg Arg Gln Ile
        900             905             910

Ile Leu Ser His Phe Glu Asp Lys Gln Val Gln Lys Ala Ser Leu Gly
        915             920             925

Ile Met Gly Thr Glu Lys Cys Cys Asp Asn Cys Arg Ser Arg Leu Asp
    930             935             940

His Cys Tyr Ser Met Asp Asp Ser Glu Asp Thr Ser Trp Asp Phe Gly
945             950             955             960

Pro Gln Ala Phe Lys Leu Leu Ser Ala Val Asp Ile Leu Gly Glu Lys
            965             970             975

Phe Gly Ile Gly Leu Pro Ile Leu Phe Leu Arg Gly Ser Asn Ser Gln
            980             985             990

Arg Leu Ala Asp Gln Tyr Arg Arg  His Ser Leu Phe Gly  Thr Gly Lys
        995             1000             1005

Asp Gln  Thr Glu Ser Trp Trp  Lys Ala Phe Ser Arg  Gln Leu Ile
    1010             1015             1020

Thr Glu  Gly Phe Leu Val Glu  Val Ser Arg Tyr Asn  Lys Phe Met
    1025             1030             1035

Lys Ile  Cys Ala Leu Thr Lys  Lys Gly Arg Asn Trp  Leu His Lys
    1040             1045             1050

Ala Asn  Thr Glu Ser Gln Ser  Leu Ile Leu Gln Ala  Asn Glu Glu
    1055             1060             1065

Leu Cys  Pro Lys Lys Leu Leu  Leu Pro Ser Ser Lys  Thr Val Ser
    1070             1075             1080

Ser Gly  Thr Lys Glu His Cys  Tyr Asn Gln Val Pro  Val Glu Leu
    1085             1090             1095

Ser Thr  Glu Lys Lys Ser Asn  Leu Glu Lys Leu Tyr  Ser Tyr Lys
    1100             1105             1110

Pro Cys  Asp Lys Ile Ser Ser  Gly Ser Asn Ile Ser  Lys Lys Ser
    1115             1120             1125

Ile Met  Val Gln Ser Pro Glu  Lys Ala Tyr Ser Ser  Ser Gln Pro
    1130             1135             1140

Val Ile  Ser Ala Gln Glu Gln  Glu Thr Gln Ile Val  Leu Tyr Gly
    1145             1150             1155

Lys Leu  Val Glu Ala Arg Gln  Lys His Ala Asn Lys  Met Asp Val
    1160             1165             1170

Pro Pro  Ala Ile Leu Ala Thr  Asn Lys Ile Leu Val  Asp Met Ala
    1175             1180             1185

Lys Met  Arg Pro Thr Thr Val  Glu Asn Val Lys Arg  Ile Asp Gly
    1190             1195             1200

Val Ser  Glu Gly Lys Ala Ala  Met Leu Ala Pro Leu  Leu Glu Val
    1205             1210             1215

Ile Lys  His Phe Cys Gln Thr  Asn Ser Val Gln Thr  Asp Leu Phe
    1220             1225             1230
```

-continued

```
Ser Ser  Thr Lys Pro Gln Glu  Glu Gln Lys Thr Ser  Leu Val Ala
    1235             1240             1245

Lys Asn  Lys Ile Cys Thr Leu  Ser Gln Ser Met Ala  Ile Thr Tyr
    1250             1255             1260

Ser Leu  Phe Gln Glu Lys Lys  Met Pro Leu Lys Ser  Ile Ala Glu
    1265             1270             1275

Ser Arg  Ile Leu Pro Leu Met  Thr Ile Gly Met His  Leu Ser Gln
    1280             1285             1290

Ala Val  Lys Ala Gly Cys Pro  Leu Asp Leu Glu Arg  Ala Gly Leu
    1295             1300             1305

Thr Pro  Glu Val Gln Lys Ile  Ile Ala Asp Val Ile  Arg Asn Pro
    1310             1315             1320

Pro Val  Asn Ser Asp Met Ser  Lys Ile Ser Leu Ile  Arg Met Leu
    1325             1330             1335

Val Pro  Glu Asn Ile Asp Thr  Tyr Leu Ile His Met  Ala Ile Glu
    1340             1345             1350

Ile Leu  Lys His Gly Pro Asp  Ser Gly Leu Gln Pro  Ser Cys Asp
    1355             1360             1365

Val Asn  Lys Arg Arg Cys Phe  Pro Gly Ser Glu Glu  Ile Cys Ser
    1370             1375             1380

Ser Ser  Lys Arg Ser Lys Glu  Glu Val Gly Ile Asn  Thr Glu Thr
    1385             1390             1395

Ser Ser  Ala Glu Arg Lys Arg  Arg Leu Pro Val Trp  Phe Ala Lys
    1400             1405             1410

Gly Ser  Asp Thr Ser Lys Lys  Leu Met Asp Lys Thr  Lys Arg Gly
    1415             1420             1425

Gly Leu  Phe Ser
    1430
```

```
<210> SEQ ID NO 3
<211> LENGTH: 2574
<212> TYPE: DNA
<213> ORGANISM: Homo sapiens

<400> SEQUENCE: 3
atggaatccg aggatttaag tggcagagaa ttgacaattg attccataat gaacaaagtg      60
agagacatta aaaataagtt taaaaatgaa gaccttactg atgaactaag cttgaataaa     120
atttctgctg atactacaga taactcggga actgttaacc aaattatgat gatggcaaac     180
aacccagagg actggttgag tttgttgctc aaactagaga aaaacagtgt tccgctaagt     240
gatgctcttt taaataaatt gattggtcgt tacagtcaag caattgaagc gcttccccca     300
gataaatatg gccaaaatga gagttttgct agaattcaag tgagatttgc tgaattaaaa     360
gctattcaag agccagatga tgcacgtgac tactttcaaa tggccagagc aaactgcaag     420
aaatttgctt ttgttcatat atcttttgca caatttgaac tgtcacaagg taatgtcaaa     480
aaaagtaaac aacttcttca aaaagctgta gaacgtggag cagtaccact agaaatgctg     540
gaaattgccc tgcggaattt aaacctccaa aaaaagcagc tgctttcaga ggaggaaaag     600
aagaatttat cagcatctac ggtattaact gcccaagaat cattttccgg ttcacttggg     660
catttacaga ataggaacaa cagttgtgat tccagaggac agactactaa agccaggttt     720
ttatatggag agaacatgcc accacaagat gcagaaatag gttaccggaa ttcattgaga     780
caaactaaca aaactaaaca gtcatgccca tttggaagag tcccagttaa ccttctaaat     840
```

-continued

```
agcccagatt gtgatgtgaa gacagatgat tcagttgtac cttgttttat gaaaagacaa      900
acctctagat cagaatgccg agatttggtt gtgcctggat ctaaaccaag tggaaatgat      960
tcctgtgaat taagaaattt aaagtctgtt caaaatagtc atttcaagga acctctggtg     1020
tcagatgaaa agagttctga acttattatt actgattcaa taaccctgaa gaataaaacg     1080
gaatcaagtc ttctagctaa attagaagaa actaaagagt atcaagaacc agaggttcca     1140
gagagtaacc agaaacagtg gcaatctaag agaaagtcag agtgtattaa ccagaatcct     1200
gctgcatctt caaatcactg gcagattccg gagttagccc gaaaagttaa tacagagcag     1260
aaacatacca cttttgagca acctgtcttt tcagtttcaa aacagtcacc accaatatca     1320
acatctaaat ggtttgaccc aaaatctatt tgtaagacac caagcagcaa taccttggat     1380
gattacatga gctgttttag aactccagtt gtaaagaatg actttccacc tgcttgtcag     1440
ttgtcaacac cttatggcca acctgcctgt ttccagcagc aacagcatca aatacttgcc     1500
actccacttc aaaatttaca ggtttttagca tcttcttcag caaatgaatg catttcggtt     1560
aaaggaagaa tttattccat attaaagcag ataggaagtg gaggttcaag caaggtattt     1620
caggtgttaa atgaaaagaa acagatatat gctataaaat atgtgaactt agaagaagca     1680
gataaccaaa ctcttgatag ttaccggaac gaaatagctt atttgaataa actacaacaa     1740
cacagtgata agatcatccg actttatgat tatgaaatca cggaccagta catctacatg     1800
gtaatggagt gtggaaatat tgatcttaat agttggctta aaaagaaaaa atccattgat     1860
ccatgggaac gcaagagtta ctggaaaaat atgttagagg cagttcacac aatccatcaa     1920
catggcattg ttcacagtga tcttaaacca gctaactttc tgatagttga tggaatgcta     1980
aagctaattg attttgggat tgcaaaccaa atgcaaccag atacaacaag tgttgttaaa     2040
gattctcagg ttggcacagt taattatatg ccaccagaag caatcaaaga tatgtcttcc     2100
tccagagaga atgggaaatc taagtcaaag ataagcccca aaagtgatgt ttggtcctta     2160
ggatgtattt tgtactatat gacttacggg aaaacaccat ttcagcagat aattaatcag     2220
atttctaaat tacatgccat aattgatcct aatcatgaaa ttgaatttcc cgatattcca     2280
gagaaagatc ttcaagatgt gttaaagtgt gtgtttaaaaa gggacccaaa acagaggata     2340
tccattcctg agctcctggc tcatccatat gttcaaattc aaactcatcc agttaaccaa     2400
atggccaagg gaaccactga agaaatgaaa tatgttctgg gccaacttgt tggtctgaat     2460
tctcctaact ccattttgaa agctgctaaa actttatatg aacactatag tggtggtgaa     2520
agtcataatt cttcatcctc caagactttt gaaaaaaaaa ggggaaaaaa atga          2574
```

<210> SEQ ID NO 4
<211> LENGTH: 857
<212> TYPE: PRT
<213> ORGANISM: Homo sapiens

<400> SEQUENCE: 4

```
Met Glu Ser Glu Asp Leu Ser Gly Arg Glu Leu Thr Ile Asp Ser Ile
1               5                   10                  15

Met Asn Lys Val Arg Asp Ile Lys Asn Lys Phe Lys Asn Glu Asp Leu
            20                  25                  30

Thr Asp Glu Leu Ser Leu Asn Lys Ile Ser Ala Asp Thr Thr Asp Asn
        35                  40                  45

Ser Gly Thr Val Asn Gln Ile Met Met Met Ala Asn Asn Pro Glu Asp
    50                  55                  60

Trp Leu Ser Leu Leu Leu Lys Leu Glu Lys Asn Ser Val Pro Leu Ser
```

-continued

```
65              70              75              80

Asp Ala Leu Leu Asn Lys Leu Ile Gly Arg Tyr Ser Gln Ala Ile Glu
                85              90              95

Ala Leu Pro Pro Asp Lys Tyr Gly Gln Asn Glu Ser Phe Ala Arg Ile
            100             105             110

Gln Val Arg Phe Ala Glu Leu Lys Ala Ile Gln Glu Pro Asp Asp Ala
            115             120             125

Arg Asp Tyr Phe Gln Met Ala Arg Ala Asn Cys Lys Lys Phe Ala Phe
        130             135             140

Val His Ile Ser Phe Ala Gln Phe Glu Leu Ser Gln Gly Asn Val Lys
145             150             155             160

Lys Ser Lys Gln Leu Leu Gln Lys Ala Val Glu Arg Gly Ala Val Pro
                165             170             175

Leu Glu Met Leu Glu Ile Ala Leu Arg Asn Leu Asn Leu Gln Lys Lys
            180             185             190

Gln Leu Leu Ser Glu Glu Lys Lys Asn Leu Ser Ala Ser Thr Val
            195             200             205

Leu Thr Ala Gln Glu Ser Phe Ser Gly Ser Leu Gly His Leu Gln Asn
        210             215             220

Arg Asn Asn Ser Cys Asp Ser Arg Gly Gln Thr Thr Lys Ala Arg Phe
225             230             235             240

Leu Tyr Gly Glu Asn Met Pro Pro Gln Asp Ala Glu Ile Gly Tyr Arg
            245             250             255

Asn Ser Leu Arg Gln Thr Asn Lys Thr Lys Gln Ser Cys Pro Phe Gly
            260             265             270

Arg Val Pro Val Asn Leu Leu Asn Ser Pro Asp Cys Asp Val Lys Thr
            275             280             285

Asp Asp Ser Val Val Pro Cys Phe Met Lys Arg Gln Thr Ser Arg Ser
        290             295             300

Glu Cys Arg Asp Leu Val Val Pro Gly Ser Lys Pro Ser Gly Asn Asp
305             310             315             320

Ser Cys Glu Leu Arg Asn Leu Lys Ser Val Gln Asn Ser His Phe Lys
            325             330             335

Glu Pro Leu Val Ser Asp Glu Lys Ser Ser Glu Leu Ile Ile Thr Asp
            340             345             350

Ser Ile Thr Leu Lys Asn Lys Thr Glu Ser Ser Leu Leu Ala Lys Leu
            355             360             365

Glu Glu Thr Lys Glu Tyr Gln Glu Pro Glu Val Pro Glu Ser Asn Gln
        370             375             380

Lys Gln Trp Gln Ser Lys Arg Lys Ser Glu Cys Ile Asn Gln Asn Pro
385             390             395             400

Ala Ala Ser Ser Asn His Trp Gln Ile Pro Glu Leu Ala Arg Lys Val
            405             410             415

Asn Thr Glu Gln Lys His Thr Thr Phe Glu Gln Pro Val Phe Ser Val
        420             425             430

Ser Lys Gln Ser Pro Pro Ile Ser Thr Ser Lys Trp Phe Asp Pro Lys
        435             440             445

Ser Ile Cys Lys Thr Pro Ser Ser Asn Thr Leu Asp Asp Tyr Met Ser
        450             455             460

Cys Phe Arg Thr Pro Val Val Lys Asn Asp Phe Pro Pro Ala Cys Gln
465             470             475             480

Leu Ser Thr Pro Tyr Gly Gln Pro Ala Cys Phe Gln Gln Gln His
        485             490             495
```

```
Gln Ile Leu Ala Thr Pro Leu Gln Asn Leu Gln Val Leu Ala Ser Ser
        500                 505                 510

Ser Ala Asn Glu Cys Ile Ser Val Lys Gly Arg Ile Tyr Ser Ile Leu
        515                 520                 525

Lys Gln Ile Gly Ser Gly Gly Ser Ser Lys Val Phe Gln Val Leu Asn
        530                 535                 540

Glu Lys Lys Gln Ile Tyr Ala Ile Lys Tyr Val Asn Leu Glu Glu Ala
545                 550                 555                 560

Asp Asn Gln Thr Leu Asp Ser Tyr Arg Asn Glu Ile Ala Tyr Leu Asn
                565                 570                 575

Lys Leu Gln Gln His Ser Asp Lys Ile Ile Arg Leu Tyr Asp Tyr Glu
                580                 585                 590

Ile Thr Asp Gln Tyr Ile Tyr Met Val Met Glu Cys Gly Asn Ile Asp
        595                 600                 605

Leu Asn Ser Trp Leu Lys Lys Lys Lys Ser Ile Asp Pro Trp Glu Arg
        610                 615                 620

Lys Ser Tyr Trp Lys Asn Met Leu Glu Ala Val His Thr Ile His Gln
625                 630                 635                 640

His Gly Ile Val His Ser Asp Leu Lys Pro Ala Asn Phe Leu Ile Val
                645                 650                 655

Asp Gly Met Leu Lys Leu Ile Asp Phe Gly Ile Ala Asn Gln Met Gln
                660                 665                 670

Pro Asp Thr Thr Ser Val Val Lys Asp Ser Gln Val Gly Thr Val Asn
        675                 680                 685

Tyr Met Pro Pro Glu Ala Ile Lys Asp Met Ser Ser Ser Arg Glu Asn
        690                 695                 700

Gly Lys Ser Lys Ser Lys Ile Ser Pro Lys Ser Asp Val Trp Ser Leu
705                 710                 715                 720

Gly Cys Ile Leu Tyr Tyr Met Thr Tyr Gly Lys Thr Pro Phe Gln Gln
                725                 730                 735

Ile Ile Asn Gln Ile Ser Lys Leu His Ala Ile Ile Asp Pro Asn His
                740                 745                 750

Glu Ile Glu Phe Pro Asp Ile Pro Glu Lys Asp Leu Gln Asp Val Leu
        755                 760                 765

Lys Cys Cys Leu Lys Arg Asp Pro Lys Gln Arg Ile Ser Ile Pro Glu
        770                 775                 780

Leu Leu Ala His Pro Tyr Val Gln Ile Gln Thr His Pro Val Asn Gln
785                 790                 795                 800

Met Ala Lys Gly Thr Thr Glu Glu Met Lys Tyr Val Leu Gly Gln Leu
                805                 810                 815

Val Gly Leu Asn Ser Pro Asn Ser Ile Leu Lys Ala Ala Lys Thr Leu
                820                 825                 830

Tyr Glu His Tyr Ser Gly Gly Glu Ser His Asn Ser Ser Ser Ser Lys
        835                 840                 845

Thr Phe Glu Lys Lys Arg Gly Lys Lys
        850                 855
```

```
<210> SEQ ID NO 5
<211> LENGTH: 3000
<212> TYPE: DNA
<213> ORGANISM: Homo sapiens

<400> SEQUENCE: 5
atgtcccgga tcgaaaagat gagcattctg ggcgtgcgga gttttggaat agaggacaaa      60
```

```
gataagcaaa ttatcacttt cttcagcccc cttacaattt tggttggacc caatggggcg      120
ggaaagacga ccatcattga atgtctaaaa tatatttgta ctggagattt ccctcctgga      180
accaaaggaa atacatttgt acacgatccc aaggttgctc aagaaacaga tgtgagagcc      240
cagattcgtc tgcaatttcg tgatgtcaat ggagaactta tagctgtgca aagatctatg      300
gtgtgtactc agaaaagcaa aaagacagaa tttaaaactc tggaaggagt cattactaga      360
acaaagcatg gtgaaaaggt cagtctgagc tctaagtgtg cagaaattga ccgagaaatg      420
atcagttctc ttggggtttc caaggctgtg ctaaataatg tcattttctg tcatcaagaa      480
gattctaatt ggcctttaag tgaaggaaag gctttgaagc aaaagtttga tgagattttt      540
tcagcaacaa gatacattaa agccttagaa acacttcggc aggtacgtca gacacaaggt      600
cagaaagtaa aagaatatca aatggaacta aaatatctga agcaatataa ggaaaaagct      660
tgtgagattc gtgatcagat tacaagtaag gaagcccagt taacatcttc aaaggaaatt      720
gtcaaatcct atgagaatga acttgatcca ttgaagaatc gtctaaaaga aattgaacat      780
aatctctcta aaataatgaa acttgacaat gaaattaaag ccttggatag ccgaaagaag      840
caaatggaga aagataatag tgaactggaa gagaaaatgg aaaaggtttt tcaagggact      900
gatgagcaac taaatgactt atatcacaat caccagagaa cagtaaggga gaaagaaagg      960
aaattggtag actgtcatcg tgaactggaa aaactaaata agaatctag gcttctcaat     1020 caggaaaaat cagaactgct tgttgaacag ggtcgtctac agctgcaagc agatcgccat     1080
caagaacata tccgagctag agattcatta attcagtctt tggcaacaca gctagaattg     1140
gatggctttg agcgtggacc attcagtgaa agacagatta aaaattttca caacttgtg     1200 agagagagac aagaagggga agcaaaaact gccaaccaac tgatgaatga ctttgcagaa     1260
aaagagactc tgaaacaaaa acagatagat gagataagag ataagaaaac tggactggga     1320
agaataattg agttaaaatc agaaatccta agtaagaagc agaatgagct gaaaaatgtg     1380
aagtatgaat tacagcagtt ggaaggatct tcagacagga ttcttgaact ggaccaggag     1440
ctcataaaag ctgaacgtga gttaagcaag gctgagaaaa acagcaatgt agaaaccta     1500 aaaatggaag taataagtct ccaaaatgaa aaagcagact tagacaggac cctgcgtaaa     1560
cttgaccagg agatggagca gttaaaccat catacaacaa cacgtaccca aatggagatg     1620
ctgaccaaag acaaagctga caaagatgaa caaatcagaa aaataaaatc taggcacagt     1680
gatgaattaa cctcactgtt gggatatttt cccaacaaaa aacagcttga agactggcta     1740
catagtaaat caaaagaaat taatcagacc agggacagac ttgccaaatt gaacaaggaa     1800
ctagcttcat ctgagcagaa taaaaatcat ataaataatg aactaaaaag aaaggaagag     1860
cagttgtcca gttacgaaga caagctgttt gatgtttgtg gtagccagga ttttgaaagt     1920
gatttagaca ggcttaaaga ggaaattgaa aaatcatcaa acagcgagc catgctggct     1980 ggagccacag cagtttactc ccagttcatt actcagctaa cagacgaaaa ccagtcatgt     2040
tgccccgttt gtcagagagt tttttcagaca gaggctgagt tacaagaagt catcagtgat     2100
ttgcagtcta aactgcgact tgctccagat aaactcaagt caacagaatc agagctaaaa     2160
aaaaaggaaa agcggcgtga tgaaatgctg ggacttgtgc ccatgaggca aagcataatt     2220
gatttgaagg agaaggaaat accagaatta agaaacaaac tgcagaatgt caatagagac     2280
atacagcgcc taaagaacga catagaagaa caagaaacac tcttgggtac aataatgcct     2340
gaagaagaaa gtgccaaagt atgcctgaca gatgttacaa ttatggagag gttccagatg     2400
```

```
gaacttaaag atgttgaaag aaaaattgca caacaagcag ctaagctaca aggaatagac    2460
ttagatcgaa ctgtccaaca agtcaaccag gagaaacaag agaaacagca caagttagac    2520
acagtttcta gtaagattga attgaatcgt aagcttatac aggaccagca ggaacagatt    2580
caacatctaa aaagtacaac aaatgagcta aaatctgaga aacttcagat atccactaat    2640
ttgcaacgtc gtcagcaact ggaggagcag actgtggaat tatccactga agttcagtct    2700
ttgtacagag agataaagga tgctaaagag caggtaagcc ctttggaaac aacattggaa    2760
aagttccagc aagaaaaaga agaattaatc aacaaaaaaa atacaagcaa caaaatagca    2820
caggataaac tgaatgatat taaagagaag gttaaaaata ttcatggcta tatgaaagac    2880
attgagaatt atattcaaga tgggaaagac gactataaga agcaaaaaga aactgaactt    2940
aataaagtaa tagctcaact aagtgaatgc gagaaacaca agaaaagat aaatgaagat     3000
```

```
<210> SEQ ID NO 6
<211> LENGTH: 1312
<212> TYPE: PRT
<213> ORGANISM: Homo sapiens

<400> SEQUENCE: 6

Met Ser Arg Ile Glu Lys Met Ser Ile Leu Gly Val Arg Ser Phe Gly
1               5                   10                  15

Ile Glu Asp Lys Asp Lys Gln Ile Ile Thr Phe Phe Ser Pro Leu Thr
            20                  25                  30

Ile Leu Val Gly Pro Asn Gly Ala Gly Lys Thr Thr Ile Ile Glu Cys
        35                  40                  45

Leu Lys Tyr Ile Cys Thr Gly Asp Phe Pro Pro Gly Thr Lys Gly Asn
    50                  55                  60

Thr Phe Val His Asp Pro Lys Val Ala Gln Glu Thr Asp Val Arg Ala
65                  70                  75                  80

Gln Ile Arg Leu Gln Phe Arg Asp Val Asn Gly Glu Leu Ile Ala Val
                85                  90                  95

Gln Arg Ser Met Val Cys Thr Gln Lys Ser Lys Lys Thr Glu Phe Lys
            100                 105                 110

Thr Leu Glu Gly Val Ile Thr Arg Thr Lys His Gly Glu Lys Val Ser
        115                 120                 125

Leu Ser Ser Lys Cys Ala Glu Ile Asp Arg Glu Met Ile Ser Ser Leu
    130                 135                 140

Gly Val Ser Lys Ala Val Leu Asn Asn Val Ile Phe Cys His Gln Glu
145                 150                 155                 160

Asp Ser Asn Trp Pro Leu Ser Glu Gly Lys Ala Leu Lys Gln Lys Phe
                165                 170                 175

Asp Glu Ile Phe Ser Ala Thr Arg Tyr Ile Lys Ala Leu Glu Thr Leu
            180                 185                 190

Arg Gln Val Arg Gln Thr Gln Gly Gln Lys Val Lys Glu Tyr Gln Met
        195                 200                 205

Glu Leu Lys Tyr Leu Lys Gln Tyr Lys Glu Lys Ala Cys Glu Ile Arg
    210                 215                 220

Asp Gln Ile Thr Ser Lys Glu Ala Gln Leu Thr Ser Ser Lys Glu Ile
225                 230                 235                 240

Val Lys Ser Tyr Glu Asn Glu Leu Asp Pro Leu Lys Asn Arg Leu Lys
                245                 250                 255

Glu Ile Glu His Asn Leu Ser Lys Ile Met Lys Leu Asp Asn Glu Ile
            260                 265                 270
```

```
Lys Ala Leu Asp Ser Arg Lys Lys Gln Met Glu Lys Asp Asn Ser Glu
        275                 280                 285

Leu Glu Glu Lys Met Glu Lys Val Phe Gln Gly Thr Asp Glu Gln Leu
        290                 295                 300

Asn Asp Leu Tyr His Asn His Gln Arg Thr Val Arg Glu Lys Glu Arg
305                 310                 315                 320

Lys Leu Val Asp Cys His Arg Glu Leu Glu Lys Leu Asn Lys Glu Ser
                325                 330                 335

Arg Leu Leu Asn Gln Glu Lys Ser Glu Leu Leu Val Glu Gln Gly Arg
                340                 345                 350

Leu Gln Leu Gln Ala Asp Arg His Gln Glu His Ile Arg Ala Arg Asp
        355                 360                 365

Ser Leu Ile Gln Ser Leu Ala Thr Gln Leu Glu Leu Asp Gly Phe Glu
        370                 375                 380

Arg Gly Pro Phe Ser Glu Arg Gln Ile Lys Asn Phe His Lys Leu Val
385                 390                 395                 400

Arg Glu Arg Gln Glu Gly Glu Ala Lys Thr Ala Asn Gln Leu Met Asn
                405                 410                 415

Asp Phe Ala Glu Lys Glu Thr Leu Lys Gln Lys Gln Ile Asp Glu Ile
                420                 425                 430

Arg Asp Lys Lys Thr Gly Leu Gly Arg Ile Ile Glu Leu Lys Ser Glu
                435                 440                 445

Ile Leu Ser Lys Lys Gln Asn Glu Leu Lys Asn Val Lys Tyr Glu Leu
        450                 455                 460

Gln Gln Leu Glu Gly Ser Ser Asp Arg Ile Leu Glu Leu Asp Gln Glu
465                 470                 475                 480

Leu Ile Lys Ala Glu Arg Glu Leu Ser Lys Ala Glu Lys Asn Ser Asn
                485                 490                 495

Val Glu Thr Leu Lys Met Glu Val Ile Ser Leu Gln Asn Glu Lys Ala
                500                 505                 510

Asp Leu Asp Arg Thr Leu Arg Lys Leu Asp Gln Glu Met Glu Gln Leu
        515                 520                 525

Asn His His Thr Thr Thr Arg Thr Gln Met Glu Met Leu Thr Lys Asp
        530                 535                 540

Lys Ala Asp Lys Asp Glu Gln Ile Arg Lys Ile Lys Ser Arg His Ser
545                 550                 555                 560

Asp Glu Leu Thr Ser Leu Leu Gly Tyr Phe Pro Asn Lys Lys Gln Leu
                565                 570                 575

Glu Asp Trp Leu His Ser Lys Ser Lys Glu Ile Asn Gln Thr Arg Asp
        580                 585                 590

Arg Leu Ala Lys Leu Asn Lys Glu Leu Ala Ser Ser Glu Gln Asn Lys
        595                 600                 605

Asn His Ile Asn Asn Glu Leu Lys Arg Lys Glu Glu Gln Leu Ser Ser
        610                 615                 620

Tyr Glu Asp Lys Leu Phe Asp Val Cys Gly Ser Gln Asp Phe Glu Ser
625                 630                 635                 640

Asp Leu Asp Arg Leu Lys Glu Glu Ile Glu Lys Ser Ser Lys Gln Arg
                645                 650                 655

Ala Met Leu Ala Gly Ala Thr Ala Val Tyr Ser Gln Phe Ile Thr Gln
                660                 665                 670

Leu Thr Asp Glu Asn Gln Ser Cys Cys Pro Val Cys Gln Arg Val Phe
        675                 680                 685

Gln Thr Glu Ala Glu Leu Gln Glu Val Ile Ser Asp Leu Gln Ser Lys
```

```
          690             695             700

Leu Arg Leu Ala Pro Asp Lys Leu Lys Ser Thr Glu Ser Glu Leu Lys
705             710             715             720

Lys Lys Glu Lys Arg Arg Asp Glu Met Leu Gly Leu Val Pro Met Arg
                725             730             735

Gln Ser Ile Ile Asp Leu Lys Glu Lys Glu Ile Pro Glu Leu Arg Asn
            740             745             750

Lys Leu Gln Asn Val Asn Arg Asp Ile Gln Arg Leu Lys Asn Asp Ile
        755             760             765

Glu Glu Gln Glu Thr Leu Leu Gly Thr Ile Met Pro Glu Glu Glu Ser
    770             775             780

Ala Lys Val Cys Leu Thr Asp Val Thr Ile Met Glu Arg Phe Gln Met
785             790             795             800

Glu Leu Lys Asp Val Glu Arg Lys Ile Ala Gln Gln Ala Ala Lys Leu
                805             810             815

Gln Gly Ile Asp Leu Asp Arg Thr Val Gln Gln Val Asn Gln Glu Lys
            820             825             830

Gln Glu Lys Gln His Lys Leu Asp Thr Val Ser Ser Lys Ile Glu Leu
        835             840             845

Asn Arg Lys Leu Ile Gln Asp Gln Gln Glu Gln Ile Gln His Leu Lys
    850             855             860

Ser Thr Thr Asn Glu Leu Lys Ser Glu Lys Leu Gln Ile Ser Thr Asn
865             870             875             880

Leu Gln Arg Arg Gln Gln Leu Glu Glu Gln Thr Val Glu Leu Ser Thr
            885             890             895

Glu Val Gln Ser Leu Tyr Arg Glu Ile Lys Asp Ala Lys Glu Gln Val
            900             905             910

Ser Pro Leu Glu Thr Thr Leu Glu Lys Phe Gln Gln Glu Lys Glu Glu
        915             920             925

Leu Ile Asn Lys Lys Asn Thr Ser Asn Lys Ile Ala Gln Asp Lys Leu
    930             935             940

Asn Asp Ile Lys Glu Lys Val Lys Asn Ile His Gly Tyr Met Lys Asp
945             950             955             960

Ile Glu Asn Tyr Ile Gln Asp Gly Lys Asp Asp Tyr Lys Lys Gln Lys
            965             970             975

Glu Thr Glu Leu Asn Lys Val Ile Ala Gln Leu Ser Glu Cys Glu Lys
        980             985             990

His Lys Glu Lys Ile Asn Glu Asp  Met Arg Leu Met Arg  Gln Asp Ile
        995             1000            1005

Asp Thr  Gln Lys Ile Gln Glu  Arg Trp Leu Gln Asp  Asn Leu Thr
    1010            1015            1020

Leu Arg  Lys Arg Asn Glu Glu  Leu Lys Glu Val Glu  Glu Glu Arg
    1025            1030            1035

Lys Gln  His Leu Lys Glu Met  Gly Gln Met Gln Val  Leu Gln Met
    1040            1045            1050

Lys Ser  Glu His Gln Lys Leu  Glu Glu Asn Ile Asp  Asn Ile Lys
    1055            1060            1065

Arg Asn  His Asn Leu Ala Leu  Gly Arg Gln Lys Gly  Tyr Glu Glu
    1070            1075            1080

Glu Ile  Ile His Phe Lys Lys  Glu Leu Arg Glu Pro  Gln Phe Arg
    1085            1090            1095

Asp Ala  Glu Glu Lys Tyr Arg  Glu Met Met Ile Val  Met Arg Thr
    1100            1105            1110
```

```
Thr Glu  Leu Val Asn Lys Asp  Leu Asp Ile Tyr Tyr  Lys Thr Leu
    1115             1120              1125

Asp Gln  Ala Ile Met Lys Phe  His Ser Met Lys Met  Glu Glu Ile
    1130             1135              1140

Asn Lys  Ile Ile Arg Asp Leu  Trp Arg Ser Thr Tyr  Arg Gly Gln
    1145             1150              1155

Asp Ile  Glu Tyr Ile Glu Ile  Arg Ser Asp Ala Asp  Glu Asn Val
    1160             1165              1170

Ser Ala  Ser Asp Lys Arg Arg  Asn Tyr Asn Tyr Arg  Val Val Met
    1175             1180              1185

Leu Lys  Gly Asp Thr Ala Leu  Asp Met Arg Gly Arg  Cys Ser Ala
    1190             1195              1200

Gly Gln  Lys Val Leu Ala Ser  Leu Ile Ile Arg Leu  Ala Leu Ala
    1205             1210              1215

Glu Thr  Phe Cys Leu Asn Cys  Gly Ile Ile Ala Leu  Asp Glu Pro
    1220             1225              1230

Thr Thr  Asn Leu Asp Arg Glu  Asn Ile Glu Ser Leu  Ala His Ala
    1235             1240              1245

Leu Val  Glu Ile Ile Lys Ser  Arg Ser Gln Gln Arg  Asn Phe Gln
    1250             1255              1260

Leu Leu  Val Ile Thr His Asp  Glu Asp Phe Val Glu  Leu Leu Gly
    1265             1270              1275

Arg Ser  Glu Tyr Val Glu Lys  Phe Tyr Arg Ile Lys  Lys Asn Ile
    1280             1285              1290

Asp Gln  Cys Ser Glu Ile Val  Lys Cys Ser Val Ser  Ser Leu Gly
    1295             1300              1305

Phe Asn  Val His
    1310
```

```
<210> SEQ ID NO 7
<211> LENGTH: 3000
<212> TYPE: DNA
<213> ORGANISM: Homo sapiens

<400> SEQUENCE: 7
atgtctcgcc ggaagcctgc gtcgggcggc ctcgctgcct ccagctcagc ccctgcgagg    60
caagcggttt tgagccgatt cttccagtct acgggaagcc tgaaatccac ctcctcctcc   120
acaggtgcag ccgaccaggt ggaccctggc gctgcagcgg ctgcagcggc cgcagcggcc   180
gcagcgcccc cagcgccccc agctcccgcc ttcccgcccc agctgccgcc gcacatagct   240
acagaaattg acagaagaaa gaagagacca ttggaaaatg atgggcctgt taaaaagaaa   300
gtaaagaaag tccaacaaaa ggaaggagga agtgatctgg gaatgtctgg caactctgag   360
ccaaagaaat gtctgaggac caggaatgtt tcaaagtctc tggaaaaatt gaaagaattc   420
tgctgcgatt ctgcccttcc tcaaagtaga gtccagacag aatctctgca ggagagattt   480
gcagttctgc caaatgtac tgattttgat gatatcagtc ttctacacgc aaagaatgca   540
gtttcttctg aagattcgaa acgtcaaatt aatcaaaagg acacaacact ttttgatctc   600
agtcagtttg gatcatcaaa tacaagtcat gaaaatttac agaaaactgc ttccaaatca   660
gctaacaaac ggtccaaaag catctatacg ccgctagaat tacaatacat agaaatgaag   720
cagcagcaca aagatgcagt tttgtgtgtg gaatgtggat ataagtatag attctttggg   780
gaagatgcag agattgcagc ccgagagctc aatatttatt gccatttaga tcacaacttt   840
```

-continued

```
atgacagcaa gtatacctac tcacagactg tttgttcatg tacgccgcct ggtggcaaaa      900
ggatataagg tgggagttgt gaagcaaact gaaactgcag cattaaaggc cattggagac      960
aacagaagtt cactcttttc ccggaaattg actgcccttt atacaaaatc tacacttatt     1020
ggagaagatg tgaatcccct aatcaagctg gatgatgctg taaatgttga tgagataatg     1080
actgatactt ctaccagcta tcttctgtgc atctctgaaa ataaggaaaa tgttagggac     1140
aaaaaaaagg gcaacatttt tattggcatt gtgggagtgc agcctgccac aggcgaggtt     1200
gtgtttgata gtttccagga ctctgcttct cgttcagagc tagaaacccg gatgtcaagc     1260
ctgcagccag tagagctgct gcttccttcg gccttgtccg agcaaacaga ggcgctcatc     1320
cacagagcca catctgttag tgtgcaggat gacagaattc gagtcgaaag gatggataac     1380
atttattttg aatacagcca tgctttccag gcagttacag agtttttatgc aaaagataca     1440 gttgacatca aaggttctca aattatttct ggcattgtta acttagagaa gcctgtgatt     1500
tgctctttgg ctgccatcat aaaatacctc aaagaattca acttggaaaa gatgctctcc     1560
aaacctgaga attttaaaca gctatcaagt aaaatggaat ttatgacaat taatggaaca     1620
acattaagga atctggaaat cctacagaat cagactgata tgaaaaccaa aggaagtttg     1680
ctgtgggttt tagaccacac taaaacttca tttgggagac ggaagttaaa gaagtgggtg     1740
acccagccac tccttaaatt aagggaaata aatgcccggc ttgatgctgt atcggaagtt     1800
ctccattcag aatctagtgt gtttggtcag atagaaaatc atctacgtaa attgcccgac     1860
atagagaggg gactctgtag catttatcac aaaaaatgtt ctacccaaga gttcttcttg     1920
attgtcaaaa ctttatatca cctaaagtca gaatttcaag caataatacc tgctgttaat     1980
tcccacattc agtcagactt gctccggacc gttattttag aaattcctga actcctcagt     2040
ccagtggagc attacttaaa gatactcaat gaacaagctg ccaaagttgg ggataaaact     2100
gaattattta aagacctttc tgacttccct ttaataaaaa agaggaagga tgaaattcaa     2160
ggtgttattg acgagatccg aatgcatttg caagaaatac gaaaaatact aaaaaatcct     2220
tctgcacaat atgtgacagt atcaggacag gagtttatga tagaaataaa gaactctgct     2280
gtatcttgta taccaactga ttgggtaaag gttggaagca caaagctgt gagccgcttt     2340 cactctcctt ttattgtaga aaattacaga catctgaatc agctccggga gcagctagtc     2400
cttgactgca gtgctgaatg gcttgattttt ctagagaaat tcagtgaaca ttatcactcc     2460
ttgtgtaaag cagtgcatca cctagcaact gttgactgca ttttctccct ggccaaggtc     2520
gctaagcaag gagattactg cagaccaact gtacaagaag aaagaaaaat tgtaataaaa     2580
aatggaaggc accctgtgat tgatgtgttg ctgggagaac aggatcaata tgtcccaaat     2640
aatacagatt tatcagagga ctcagagaga gtaatgataa ttaccggacc aaacatgggt     2700
ggaaagagct cctacataaa acaagttgca ttgattacca tcatggctca gattggctcc     2760
tatgttcctg cagaagaagc gacaattggg attgtggatg gcattttcac aaggatgggt     2820
gctgcagaca atatatataa aggacagagt acatttatgg aagaactgac tgacacagca     2880
gaaataatca gaaaagcaac atcacagtcc ttggttatct ggatgaact aggaagaggg     2940 acgagcactc atgatggaat tgccattgcc tatgctacac ttgagtattt catcagagat     3000
```

```
<210> SEQ ID NO 8
<211> LENGTH: 1136
<212> TYPE: PRT
<213> ORGANISM: Homo sapiens

<400> SEQUENCE: 8
```

-continued

```
Met Ser Arg Arg Lys Pro Ala Ser Gly Gly Leu Ala Ala Ser Ser Ser
1               5                   10                  15

Ala Pro Ala Arg Gln Ala Val Leu Ser Arg Phe Phe Gln Ser Thr Gly
            20                  25                  30

Ser Leu Lys Ser Thr Ser Ser Ser Thr Gly Ala Ala Asp Gln Val Asp
        35                  40                  45

Pro Gly Ala Ala Ala Ala Ala Ala Ala Ala Ala Ala Ala Pro Pro
    50                  55                  60

Ala Pro Pro Ala Pro Ala Phe Pro Pro Gln Leu Pro Pro His Ile Ala
65                  70                  75                  80

Thr Glu Ile Asp Arg Arg Lys Lys Arg Pro Leu Glu Asn Asp Gly Pro
                85                  90                  95

Val Lys Lys Lys Val Lys Lys Val Gln Gln Lys Glu Gly Gly Ser Asp
            100                 105                 110

Leu Gly Met Ser Gly Asn Ser Glu Pro Lys Lys Cys Leu Arg Thr Arg
        115                 120                 125

Asn Val Ser Lys Ser Leu Glu Lys Leu Lys Glu Phe Cys Cys Asp Ser
    130                 135                 140

Ala Leu Pro Gln Ser Arg Val Gln Thr Glu Ser Leu Gln Glu Arg Phe
145                 150                 155                 160

Ala Val Leu Pro Lys Cys Thr Asp Phe Asp Asp Ile Ser Leu Leu His
                165                 170                 175

Ala Lys Asn Ala Val Ser Ser Glu Asp Ser Lys Arg Gln Ile Asn Gln
        180                 185                 190

Lys Asp Thr Thr Leu Phe Asp Leu Ser Gln Phe Gly Ser Ser Asn Thr
        195                 200                 205

Ser His Glu Asn Leu Gln Lys Thr Ala Ser Lys Ser Ala Asn Lys Arg
    210                 215                 220

Ser Lys Ser Ile Tyr Thr Pro Leu Glu Leu Gln Tyr Ile Glu Met Lys
225                 230                 235                 240

Gln Gln His Lys Asp Ala Val Leu Cys Val Glu Cys Gly Tyr Lys Tyr
                245                 250                 255

Arg Phe Phe Gly Glu Asp Ala Glu Ile Ala Ala Arg Glu Leu Asn Ile
            260                 265                 270

Tyr Cys His Leu Asp His Asn Phe Met Thr Ala Ser Ile Pro Thr His
        275                 280                 285

Arg Leu Phe Val His Val Arg Arg Leu Val Ala Lys Gly Tyr Lys Val
    290                 295                 300

Gly Val Val Lys Gln Thr Glu Thr Ala Ala Leu Lys Ala Ile Gly Asp
305                 310                 315                 320

Asn Arg Ser Ser Leu Phe Ser Arg Lys Leu Thr Ala Leu Tyr Thr Lys
            325                 330                 335

Ser Thr Leu Ile Gly Glu Asp Val Asn Pro Leu Ile Lys Leu Asp Asp
        340                 345                 350

Ala Val Asn Val Asp Glu Ile Met Thr Asp Thr Ser Thr Ser Tyr Leu
        355                 360                 365

Leu Cys Ile Ser Glu Asn Lys Glu Asn Val Arg Asp Lys Lys Lys Gly
    370                 375                 380

Asn Ile Phe Ile Gly Ile Val Gly Val Gln Pro Ala Thr Gly Glu Val
385                 390                 395                 400

Val Phe Asp Ser Phe Gln Asp Ser Ala Ser Arg Ser Glu Leu Glu Thr
                405                 410                 415
```

-continued

```
Arg Met Ser Ser Leu Gln Pro Val Glu Leu Leu Leu Pro Ser Ala Leu
        420             425             430

Ser Glu Gln Thr Glu Ala Leu Ile His Arg Ala Thr Ser Val Ser Val
        435             440             445

Gln Asp Asp Arg Ile Arg Val Glu Arg Met Asp Asn Ile Tyr Phe Glu
    450             455             460

Tyr Ser His Ala Phe Gln Ala Val Thr Glu Phe Tyr Ala Lys Asp Thr
465             470             475             480

Val Asp Ile Lys Gly Ser Gln Ile Ile Ser Gly Ile Val Asn Leu Glu
                485             490             495

Lys Pro Val Ile Cys Ser Leu Ala Ala Ile Ile Lys Tyr Leu Lys Glu
            500             505             510

Phe Asn Leu Glu Lys Met Leu Ser Lys Pro Glu Asn Phe Lys Gln Leu
        515             520             525

Ser Ser Lys Met Glu Phe Met Thr Ile Asn Gly Thr Thr Leu Arg Asn
    530             535             540

Leu Glu Ile Leu Gln Asn Gln Thr Asp Met Lys Thr Lys Gly Ser Leu
545             550             555             560

Leu Trp Val Leu Asp His Thr Lys Thr Ser Phe Gly Arg Arg Lys Leu
                565             570             575

Lys Lys Trp Val Thr Gln Pro Leu Leu Lys Leu Arg Glu Ile Asn Ala
            580             585             590

Arg Leu Asp Ala Val Ser Glu Val Leu His Ser Glu Ser Ser Val Phe
        595             600             605

Gly Gln Ile Glu Asn His Leu Arg Lys Leu Pro Asp Ile Glu Arg Gly
        610             615             620

Leu Cys Ser Ile Tyr His Lys Lys Cys Ser Thr Gln Glu Phe Phe Leu
625             630             635             640

Ile Val Lys Thr Leu Tyr His Leu Lys Ser Glu Phe Gln Ala Ile Ile
                645             650             655

Pro Ala Val Asn Ser His Ile Gln Ser Asp Leu Leu Arg Thr Val Ile
            660             665             670

Leu Glu Ile Pro Glu Leu Leu Ser Pro Val Glu His Tyr Leu Lys Ile
            675             680             685

Leu Asn Glu Gln Ala Ala Lys Val Gly Asp Lys Thr Glu Leu Phe Lys
        690             695             700

Asp Leu Ser Asp Phe Pro Leu Ile Lys Lys Arg Lys Asp Glu Ile Gln
705             710             715             720

Gly Val Ile Asp Glu Ile Arg Met His Leu Gln Glu Ile Arg Lys Ile
                725             730             735

Leu Lys Asn Pro Ser Ala Gln Tyr Val Thr Val Ser Gly Gln Glu Phe
            740             745             750

Met Ile Glu Ile Lys Asn Ser Ala Val Ser Cys Ile Pro Thr Asp Trp
        755             760             765

Val Lys Val Gly Ser Thr Lys Ala Val Ser Arg Phe His Ser Pro Phe
        770             775             780

Ile Val Glu Asn Tyr Arg His Leu Asn Gln Leu Arg Glu Gln Leu Val
785             790             795             800

Leu Asp Cys Ser Ala Glu Trp Leu Asp Phe Leu Glu Lys Phe Ser Glu
                805             810             815

His Tyr His Ser Leu Cys Lys Ala Val His His Leu Ala Thr Val Asp
            820             825             830

Cys Ile Phe Ser Leu Ala Lys Val Ala Lys Gln Gly Asp Tyr Cys Arg
```

-continued

```
          835                 840                 845

Pro Thr Val Gln Glu Glu Arg Lys Ile Val Ile Lys Asn Gly Arg His
    850                 855                 860

Pro Val Ile Asp Val Leu Leu Gly Glu Gln Asp Gln Tyr Val Pro Asn
865                 870                 875                 880

Asn Thr Asp Leu Ser Glu Asp Ser Glu Arg Val Met Ile Ile Thr Gly
                885                 890                 895

Pro Asn Met Gly Gly Lys Ser Ser Tyr Ile Lys Gln Val Ala Leu Ile
            900                 905                 910

Thr Ile Met Ala Gln Ile Gly Ser Tyr Val Pro Ala Glu Glu Ala Thr
            915                 920                 925

Ile Gly Ile Val Asp Gly Ile Phe Thr Arg Met Gly Ala Ala Asp Asn
    930                 935                 940

Ile Tyr Lys Gly Gln Ser Thr Phe Met Glu Glu Leu Thr Asp Thr Ala
945                 950                 955                 960

Glu Ile Ile Arg Lys Ala Thr Ser Gln Ser Leu Val Ile Leu Asp Glu
                965                 970                 975

Leu Gly Arg Gly Thr Ser Thr His Asp Gly Ile Ala Ile Ala Tyr Ala
            980                 985                 990

Thr Leu Glu Tyr Phe Ile Arg Asp  Val Lys Ser Leu Thr  Leu Phe Val
            995                 1000                1005

Thr His  Tyr Pro Pro Val Cys  Glu Leu Glu Lys Asn  Tyr Ser His
    1010                1015                1020

Gln Val  Gly Asn Tyr His Met  Gly Phe Leu Val Ser  Glu Asp Glu
    1025                1030                1035

Ser Lys  Leu Asp Pro Gly Ala  Ala Glu Gln Val Pro  Asp Phe Val
    1040                1045                1050

Thr Phe  Leu Tyr Gln Ile Thr  Arg Gly Ile Ala Ala  Arg Ser Tyr
    1055                1060                1065

Gly Leu  Asn Val Ala Lys Leu  Ala Asp Val Pro Gly  Glu Ile Leu
    1070                1075                1080

Lys Lys  Ala Ala His Lys Ser  Lys Glu Leu Glu Gly  Leu Ile Asn
    1085                1090                1095

Thr Lys  Arg Lys Arg Leu Lys  Tyr Phe Ala Lys Leu  Trp Thr Met
    1100                1105                1110

His Asn  Ala Gln Asp Leu Gln  Lys Trp Thr Glu Glu  Phe Asn Met
    1115                1120                1125

Glu Glu  Thr Gln Thr Ser Leu  Leu
    1130                1135
```

```
<210> SEQ ID NO 9
<211> LENGTH: 2127
<212> TYPE: DNA
<213> ORGANISM: Homo sapiens

<400> SEQUENCE: 9
atgagtactg cagatgcact tgatgatgaa aacacattta aaatattagt tgcaacagat      60
attcatcttg gatttatgga gaaagatgca gtcagaggaa atgatacgtt tgtaacactc     120
gatgaaattt taagacttgc ccaggaaaat gaagtggatt ttattttgtt aggtggtgat     180
ctttttcatg aaaataagcc ctcaaggaaa acattacata cctgcctcga gttattaaga     240
aaatattgta tgggtgatcg gcctgtccag tttgaaattc tcagtgatca gtcagtcaac     300
tttggtttta gtaagtttcc atgggtgaac tatcaagatg gcaacctcaa catttcaatt     360
```

```
ccagtgttta gtattcatgg caatcatgac gatcccacag gggcagatgc actttgtgcc        420
ttggacattt taagttgtgc tggatttgta aatcactttg gacgttcaat gtctgtggag        480
aagatagaca ttagtccggt tttgcttcaa aaaggaagca caaagattgc gctatatggt        540
ttaggatcca ttccagatga aaggctctat cgaatgtttg tcaataaaaa agtaacaatg        600
ttgagaccaa aggaagatga gaactcttgg tttaacttat ttgtgattca tcagaacagg        660
agtaaacatg gaagtactaa cttcattcca gaacaatttt tggatgactt cattgatctt        720
gttatctggg gccatgaaca tgagtgtaaa atagctccaa ccaaaaatga acaacagctg        780
ttttatatct cacaacctgg aagctcagtg gttacttctc tttccccagg agaagctgta        840
aagaaacatg ttggtttgct gcgtattaaa gggaggaaga tgaatatgca taaaattcct        900
cttcacacag tgcggcagtt tttcatggag gatattgttc tagctaatca tccagacatt        960
tttaacccag ataatcctaa agtaacccaa gccatacaaa gcttctgttt ggagaagatt       1020
gaagaaatgc ttgaaaatgc tgaacgggaa cgtctgggta attctcacca gccagagaag       1080
cctcttgtac gactgcgagt ggactatagt ggaggttttg aacctttcag tgttcttcgc       1140
tttagccaga aatttgtgga tcgggtagct aatccaaaag acattatcca ttttttcagg       1200
catagagaac aaaaggaaaa aacaggagaa gagatcaact ttgggaaact tatcacaaag       1260
ccttcagaag gaacaacttt aagggtagaa gatcttgtaa aacagtactt caaaccgca       1320 gagaagaatg tgcagctctc actgctaaca gaaagaggga tgggtgaagc agtacaagaa       1380
tttgtggaca aggaggagaa agatgccatt gaggaattag tgaaatacca gttggaaaaa       1440
acacagcgat ttcttaaaga acgtcatatt gatgccctcg aagacaaaat cgatgaggag       1500
gtacgtcgtt tcagagaaac cagacaaaaa aatactaatg aagaagatga tgaagtccgt       1560
gaggctatga ccagggccag agcactcaga tctcagtcag aggagtctgc ttctgccttt       1620
agtgctgatg accttatgag tatagattta gcagaacaga tggctaatga ctctgatgat       1680
agcatctcag cagcaaccaa caaaggaaga ggccgaggaa gaggtcgaag aggtggaaga       1740
gggcagaatt cagcatcgag aggagggtct caaagaggaa gagcagacac tggtctggag       1800
acttctaccc gtagcaggaa ctcaaagact gctgtgtcag catctagaaa tatgtctatt       1860
atagatgcct ttaaatctac aagacagcag ccttcccgaa atgtcactac taagaattat       1920
tcagaggtga ttgaggtaga tgaatcagat gtggaagaag acattttttcc taccacttca       1980 aagacagatc aaaggtggtc cagcacatca tccagcaaaa tcatgtccca gagtcaagta       2040
tcgaaagggg ttgattttga atcaagtgag gatgatgatg atgatccttt tatgaacact       2100
agttctttaa gaagaaatag aagataa                                           2127
```

```
<210> SEQ ID NO 10
<211> LENGTH: 708
<212> TYPE: PRT
<213> ORGANISM: Homo sapiens

<400> SEQUENCE: 10
```

```
Met Ser Thr Ala Asp Ala Leu Asp Asp Glu Asn Thr Phe Lys Ile Leu
1               5                   10                  15

Val Ala Thr Asp Ile His Leu Gly Phe Met Glu Lys Asp Ala Val Arg
            20                  25                  30

Gly Asn Asp Thr Phe Val Thr Leu Asp Glu Ile Leu Arg Leu Ala Gln
        35                  40                  45

Glu Asn Glu Val Asp Phe Ile Leu Leu Gly Gly Asp Leu Phe His Glu
    50                  55                  60
```

-continued

```
Asn Lys Pro Ser Arg Lys Thr Leu His Thr Cys Leu Glu Leu Leu Arg
65              70              75              80

Lys Tyr Cys Met Gly Asp Arg Pro Val Gln Phe Glu Ile Leu Ser Asp
                85              90              95

Gln Ser Val Asn Phe Gly Phe Ser Lys Phe Pro Trp Val Asn Tyr Gln
            100             105             110

Asp Gly Asn Leu Asn Ile Ser Ile Pro Val Phe Ser Ile His Gly Asn
            115             120             125

His Asp Asp Pro Thr Gly Ala Asp Ala Leu Cys Ala Leu Asp Ile Leu
    130             135             140

Ser Cys Ala Gly Phe Val Asn His Phe Gly Arg Ser Met Ser Val Glu
145             150             155             160

Lys Ile Asp Ile Ser Pro Val Leu Leu Gln Lys Gly Ser Thr Lys Ile
                165             170             175

Ala Leu Tyr Gly Leu Gly Ser Ile Pro Asp Glu Arg Leu Tyr Arg Met
            180             185             190

Phe Val Asn Lys Lys Val Thr Met Leu Arg Pro Lys Glu Asp Glu Asn
            195             200             205

Ser Trp Phe Asn Leu Phe Val Ile His Gln Asn Arg Ser Lys His Gly
    210             215             220

Ser Thr Asn Phe Ile Pro Glu Gln Phe Leu Asp Asp Phe Ile Asp Leu
225             230             235             240

Val Ile Trp Gly His Glu His Glu Cys Lys Ile Ala Pro Thr Lys Asn
            245             250             255

Glu Gln Gln Leu Phe Tyr Ile Ser Gln Pro Gly Ser Ser Val Val Thr
            260             265             270

Ser Leu Ser Pro Gly Glu Ala Val Lys Lys His Val Gly Leu Leu Arg
    275             280             285

Ile Lys Gly Arg Lys Met Asn Met His Lys Ile Pro Leu His Thr Val
    290             295             300

Arg Gln Phe Phe Met Glu Asp Ile Val Leu Ala Asn His Pro Asp Ile
305             310             315             320

Phe Asn Pro Asp Asn Pro Lys Val Thr Gln Ala Ile Gln Ser Phe Cys
            325             330             335

Leu Glu Lys Ile Glu Glu Met Leu Glu Asn Ala Glu Arg Glu Arg Leu
            340             345             350

Gly Asn Ser His Gln Pro Glu Lys Pro Leu Val Arg Leu Arg Val Asp
    355             360             365

Tyr Ser Gly Gly Phe Glu Pro Phe Ser Val Leu Arg Phe Ser Gln Lys
    370             375             380

Phe Val Asp Arg Val Ala Asn Pro Lys Asp Ile Ile His Phe Phe Arg
385             390             395             400

His Arg Glu Gln Lys Glu Lys Thr Gly Glu Glu Ile Asn Phe Gly Lys
            405             410             415

Leu Ile Thr Lys Pro Ser Glu Gly Thr Thr Leu Arg Val Glu Asp Leu
            420             425             430

Val Lys Gln Tyr Phe Gln Thr Ala Glu Lys Asn Val Gln Leu Ser Leu
    435             440             445

Leu Thr Glu Arg Gly Met Gly Glu Ala Val Gln Glu Phe Val Asp Lys
    450             455             460

Glu Glu Lys Asp Ala Ile Glu Glu Leu Val Lys Tyr Gln Leu Glu Lys
465             470             475             480
```

```
Thr Gln Arg Phe Leu Lys Glu Arg His Ile Asp Ala Leu Glu Asp Lys
                485                 490                 495

Ile Asp Glu Glu Val Arg Arg Phe Arg Glu Thr Arg Gln Lys Asn Thr
            500                 505                 510

Asn Glu Glu Asp Asp Glu Val Arg Glu Ala Met Thr Arg Ala Arg Ala
        515                 520                 525

Leu Arg Ser Gln Ser Glu Glu Ser Ala Ser Ala Phe Ser Ala Asp Asp
    530                 535                 540

Leu Met Ser Ile Asp Leu Ala Glu Gln Met Ala Asn Asp Ser Asp Asp
545                 550                 555                 560

Ser Ile Ser Ala Ala Thr Asn Lys Gly Arg Gly Arg Gly Arg Gly Arg
                565                 570                 575

Arg Gly Gly Arg Gly Gln Asn Ser Ala Ser Arg Gly Gly Ser Gln Arg
            580                 585                 590

Gly Arg Ala Asp Thr Gly Leu Glu Thr Ser Thr Arg Ser Arg Asn Ser
        595                 600                 605

Lys Thr Ala Val Ser Ala Ser Arg Asn Met Ser Ile Ile Asp Ala Phe
    610                 615                 620

Lys Ser Thr Arg Gln Gln Pro Ser Arg Asn Val Thr Thr Lys Asn Tyr
625                 630                 635                 640

Ser Glu Val Ile Glu Val Asp Glu Ser Asp Val Glu Glu Asp Ile Phe
                645                 650                 655

Pro Thr Thr Ser Lys Thr Asp Gln Arg Trp Ser Ser Thr Ser Ser Ser
            660                 665                 670

Lys Ile Met Ser Gln Ser Gln Val Ser Lys Gly Val Asp Phe Glu Ser
            675                 680                 685

Ser Glu Asp Asp Asp Asp Asp Pro Phe Met Asn Thr Ser Ser Leu Arg
    690                 695                 700

Arg Asn Arg Arg
705
```

```
<210> SEQ ID NO 11
<211> LENGTH: 2265
<212> TYPE: DNA
<213> ORGANISM: Homo sapiens

<400> SEQUENCE: 11
atgtggaaac tgctgcccgc cgcgggcccg gcaggaggag aaccatacag acttttgact        60
ggcgttgagt acgttgttgg aaggaaaaac tgtgccattc tgattgaaaa tgatcagtcg       120
atcagccgaa tcatgctgt gttaactgct aactttctg taaccaacct gagtcaaaca        180
gatgaaatcc ctgtattgac attaaaagat aattctaagt atggtacctt tgttaatgag       240
gaaaaaatgc agaatggctt ttcccgaact ttgaagtcgg gggatggtat tacttttgga       300
gtgtttggaa gtaaattcag aatagagtat gagcctttgg ttgcatgctc ttcttgttta       360
gatgtctctg ggaaaactgc tttaaatcaa gctatattgc aacttggagg atttactgta       420
aacaattgga cagaagaatg cactcacctt gtcatggtat cagtgaaagt taccattaaa       480
acaatatgtg cactcatttg tggacgtcca attgtaaagc cagaatattt tactgaattc       540
ctgaaagcag ttgagtccaa gaagcagcct ccacaaattg aaagtttta cccacctctt       600 gatgaaccat ctattggaag taaaaatgtt gatctgtcag acggcaggaa agaaaacaa        660 atcttcaaag ggaaaacatt tatattttg aatgccaaac agcataagaa attgagttcc       720
gcagttgtct ttggaggtgg ggaagctagg ttgataacag aagagaatga agaagaacat       780
```

-continued

```
aatttctttt tggctccggg aacgtgtgtt gttgatacag gaataacaaa ctcacagacc    840
ttaattcctg actgtcagaa gaaatggatt cagtcaataa tggatatgct ccaaaggcaa    900
ggtcttagac ctattcctga agcagaaatt ggattggcgg tgattttcat gactacaaag    960
aattactgtg atcctcaggg ccatcccagt acaggattaa agacaacaac tccaggacca   1020
agcctttcac aaggcgtgtc agttgatgaa aaactaatgc caagcgcccc agtgaacact   1080
acaacatacg tagctgacac agaatcagag caagcagata catgggattt gagtgaaagg   1140
ccaaaagaaa tcaaagtctc caaatggaa caaaaattca gaatgctttc acaagatgca   1200
cccactgtaa aggagtcctg caaaacaagc tctaataata atagtatggt atcaaatact   1260
ttggctaaga tgagaatccc aaactatcag cttttcaccaa ctaaattgcc aagtataaat   1320
aaaagtaaag atagggcttc tcagcagcag cagaccaact ccatcagaaa ctactttcag   1380
ccgtctacca aaaaaggga aagggatgaa gaaaatcaag aaatgtcttc atgcaaatca   1440
gcaagaatag aaacgtcttg ttctctttta gaacaaacac aacctgctac accctcattg   1500
tggaaaaata aggagcagca tctatctgag aatgagcctg tggacacaaa ctcagacaat   1560
aacttattta cagatacaga tttaaaatct attgtgaaaa attctgccag taaatctcat   1620
gctgcagaaa agctaagatc aaataaaaaa agggaaatgg atgatgtggc catagaagat   1680
gaagtattgg aacagttatt caaggacaca aaaccagagt tagaaattga tgtgaaagtt   1740
caaaaacagg aggaagatgt caatgttaga aaaaggccaa ggatggatat agaaacaaat   1800
gacactttca gtgatgaagc agtaccagaa agtagcaaaa tatctcaaga aaatgaaatt   1860
gggaagaaac gtgaactcaa ggaagactca ctatggtcag ctaaagaaat atctaacaat   1920
gacaaacttc aggatgatag tgagatgctt ccaaaaaagc tgttattgac tgaatttaga   1980
tcactggtga ttaaaaactc tacttccaga aatccatctg gcataaatga tgattatggt   2040
caactaaaaa atttcaagaa attcaaaaag gtcacatatc ctggagcagg aaaacttcca   2100
cacatcattg gaggatcaga tctaatagct catcatgctc gaaagaatac agaactagaa   2160
gagtggctaa ggcaggaaat ggaggtacaa aatcaacatg caaaagaaga gtctcttgct   2220
gatgatcttt ttagatacaa tccttattta aaaaggagaa gataa            2265
```

```
<210> SEQ ID NO 12
<211> LENGTH: 754
<212> TYPE: PRT
<213> ORGANISM: Homo sapiens

<400> SEQUENCE: 12

Met Trp Lys Leu Leu Pro Ala Ala Gly Pro Ala Gly Gly Glu Pro Tyr
1               5                   10                  15

Arg Leu Leu Thr Gly Val Glu Tyr Val Val Gly Arg Lys Asn Cys Ala
            20                  25                  30

Ile Leu Ile Glu Asn Asp Gln Ser Ile Ser Arg Asn His Ala Val Leu
        35                  40                  45

Thr Ala Asn Phe Ser Val Thr Asn Leu Ser Gln Thr Asp Glu Ile Pro
    50                  55                  60

Val Leu Thr Leu Lys Asp Asn Ser Lys Tyr Gly Thr Phe Val Asn Glu
65                  70                  75                  80

Glu Lys Met Gln Asn Gly Phe Ser Arg Thr Leu Lys Ser Gly Asp Gly
                85                  90                  95

Ile Thr Phe Gly Val Phe Gly Ser Lys Phe Arg Ile Glu Tyr Glu Pro
            100                 105                 110
```

-continued

```
Leu Val Ala Cys Ser Ser Cys Leu Asp Val Ser Gly Lys Thr Ala Leu
            115                 120                 125

Asn Gln Ala Ile Leu Gln Leu Gly Gly Phe Thr Val Asn Asn Trp Thr
    130                 135                 140

Glu Glu Cys Thr His Leu Val Met Val Ser Val Lys Val Thr Ile Lys
145                 150                 155                 160

Thr Ile Cys Ala Leu Ile Cys Gly Arg Pro Ile Val Lys Pro Glu Tyr
                165                 170                 175

Phe Thr Glu Phe Leu Lys Ala Val Glu Ser Lys Lys Gln Pro Pro Gln
            180                 185                 190

Ile Glu Ser Phe Tyr Pro Pro Leu Asp Glu Pro Ser Ile Gly Ser Lys
        195                 200                 205

Asn Val Asp Leu Ser Gly Arg Gln Glu Arg Lys Gln Ile Phe Lys Gly
    210                 215                 220

Lys Thr Phe Ile Phe Leu Asn Ala Lys Gln His Lys Lys Leu Ser Ser
225                 230                 235                 240

Ala Val Val Phe Gly Gly Gly Glu Ala Arg Leu Ile Thr Glu Glu Asn
                245                 250                 255

Glu Glu Glu His Asn Phe Phe Leu Ala Pro Gly Thr Cys Val Val Asp
            260                 265                 270

Thr Gly Ile Thr Asn Ser Gln Thr Leu Ile Pro Asp Cys Gln Lys Lys
            275                 280                 285

Trp Ile Gln Ser Ile Met Asp Met Leu Gln Arg Gln Gly Leu Arg Pro
    290                 295                 300

Ile Pro Glu Ala Glu Ile Gly Leu Ala Val Ile Phe Met Thr Thr Lys
305                 310                 315                 320

Asn Tyr Cys Asp Pro Gln Gly His Pro Ser Thr Gly Leu Lys Thr Thr
                325                 330                 335

Thr Pro Gly Pro Ser Leu Ser Gln Gly Val Ser Val Asp Glu Lys Leu
            340                 345                 350

Met Pro Ser Ala Pro Val Asn Thr Thr Thr Tyr Val Ala Asp Thr Glu
            355                 360                 365

Ser Glu Gln Ala Asp Thr Trp Asp Leu Ser Glu Arg Pro Lys Glu Ile
    370                 375                 380

Lys Val Ser Lys Met Glu Gln Lys Phe Arg Met Leu Ser Gln Asp Ala
385                 390                 395                 400

Pro Thr Val Lys Glu Ser Cys Lys Thr Ser Ser Asn Asn Asn Ser Met
                405                 410                 415

Val Ser Asn Thr Leu Ala Lys Met Arg Ile Pro Asn Tyr Gln Leu Ser
            420                 425                 430

Pro Thr Lys Leu Pro Ser Ile Asn Lys Ser Lys Asp Arg Ala Ser Gln
            435                 440                 445

Gln Gln Gln Thr Asn Ser Ile Arg Asn Tyr Phe Gln Pro Ser Thr Lys
    450                 455                 460

Lys Arg Glu Arg Asp Glu Glu Asn Gln Glu Met Ser Ser Cys Lys Ser
465                 470                 475                 480

Ala Arg Ile Glu Thr Ser Cys Ser Leu Leu Glu Gln Thr Gln Pro Ala
                485                 490                 495

Thr Pro Ser Leu Trp Lys Asn Lys Glu Gln His Leu Ser Glu Asn Glu
            500                 505                 510

Pro Val Asp Thr Asn Ser Asp Asn Asn Leu Phe Thr Asp Thr Asp Leu
            515                 520                 525

Lys Ser Ile Val Lys Asn Ser Ala Ser Lys Ser His Ala Ala Glu Lys
```

```
          530               535               540
Leu Arg Ser Asn Lys Lys Arg Glu Met Asp Asp Val Ala Ile Glu Asp
545                   550               555               560

Glu Val Leu Glu Gln Leu Phe Lys Asp Thr Lys Pro Glu Leu Glu Ile
                  565               570               575

Asp Val Lys Val Gln Lys Gln Glu Glu Asp Val Asn Val Arg Lys Arg
                  580               585               590

Pro Arg Met Asp Ile Glu Thr Asn Asp Thr Phe Ser Asp Glu Ala Val
            595               600               605

Pro Glu Ser Ser Lys Ile Ser Gln Glu Asn Glu Ile Gly Lys Lys Arg
            610               615               620

Glu Leu Lys Glu Asp Ser Leu Trp Ser Ala Lys Glu Ile Ser Asn Asn
625               630               635               640

Asp Lys Leu Gln Asp Asp Ser Glu Met Leu Pro Lys Lys Leu Leu Leu
                  645               650               655

Thr Glu Phe Arg Ser Leu Val Ile Lys Asn Ser Thr Ser Arg Asn Pro
                  660               665               670

Ser Gly Ile Asn Asp Asp Tyr Gly Gln Leu Lys Asn Phe Lys Lys Phe
            675               680               685

Lys Lys Val Thr Tyr Pro Gly Ala Gly Lys Leu Pro His Ile Ile Gly
            690               695               700

Gly Ser Asp Leu Ile Ala His His Ala Arg Lys Asn Thr Glu Leu Glu
705               710               715               720

Glu Trp Leu Arg Gln Glu Met Glu Val Gln Asn Gln His Ala Lys Glu
                  725               730               735

Glu Ser Leu Ala Asp Asp Leu Phe Arg Tyr Asn Pro Tyr Leu Lys Arg
            740               745               750

Arg Arg
```

<210> SEQ ID NO 13
<211> LENGTH: 3183
<212> TYPE: DNA
<213> ORGANISM: Homo sapiens

<400> SEQUENCE: 13

```
atggagcagc tgaacgaact ggagctgctg atggagaaga gttttttggga ggaggcggag      60 ctgccggcgg agctatttca gaagaaagtg gtagcttcct ttccaagaac agttctgagc     120
acaggaatgg ataaccggta cctggtgttg gcagtcaata ctgtacagaa caaagaggga     180
aactgtgaaa agcgcctggt catcactgct tcacagtcac tagaaaataa agaactatgc     240
atccttagga tgactggtg ttctgttcca gtagagccag gagatatcat tcatttggag      300
ggagactgca catctgacac ttggataata gataaagatt ttggatattt gattctgtat     360
ccagacatgc tgatttctgg caccagcata gccagtagta ttcgatgtat gagaagagct     420
gtcctgagtg aaacttttag gagctctgat ccagccacac gccaaatgct aattggtacg     480
gttctccatg aggtgtttca aaaagccata aataatagct ttgccccaga aaagctacaa     540
gaacttgctt ttcaaacaat tcaagaaata agacatttga aggaaatgta ccgcttaaat     600
ctaagtcaag atgaaataaa acaagaagta gaggactatc ttccttcgtt ttgtaaatgg     660
gcaggagatt tcatgcataa aaacacttcg actgacttcc ctcagatgca gctctctctg     720
ccaagtgata atagtaagga taattcaaca tgtaacattg aagtcgtgaa accaatggat     780
attgaagaaa gcatttggtc ccctaggttt ggattgaaag gcaaaataga tgttacagtt     840
```

-continued

```
ggtgtgaaaa tacatcgagg gtataaaaca aaatacaaga taatgccgct ggaacttaaa     900
actggcaaag aatcaaattc tattgaacac cgtagtcagg ttgttctgta cactctacta     960
agccaagaga gaagagctga tccagaggct ggcttgcttc tctacctcaa gactggtcag    1020
atgtaccctg tgcctgccaa ccatctagat aaaagagaat tattaaagct aagaaaccag    1080
atggcattct cattgtttca ccgtattagc aaatctgcta ctagacagaa gacacagctt    1140
gcttctttgc cacaaataat tgaggaagag aaaacttgta atattgttc acaaattggc      1200 aattgtgctc tttatagcag agcagttgaa caacagatgg attgtagttc agtcccaatt    1260
gtgatgctgc ccaaaataga agaagaaacc cagcatctga agcaaacaca cttagaatat    1320
ttcagccttt ggtgtctaat gttaaccctg gagtcacaat cgaaggataa taaaaagaat    1380
caccaaaata tctggctaat gcctgcttcg gaaatggaga agagtggcag ttgcattgga    1440
aacctgatta gaatggaaca tgtaaagata gtttgtgatg ggcaatattt acataatttc    1500
caatgtaaac atggtgccat acctgtcaca aatctaatgg caggtgacag agttattgta    1560
agtggagaag aaaggtcact gtttgctttg tctagaggat atgtgaagga gattaacatg    1620
acaacagtaa cttgtttatt agacagaaac ttgtcggtcc ttccagaatc aactttgttc    1680
agattagacc aagaagaaaa aaattgtgat atagataccc cattaggaaa tctttccaaa    1740
ttgatggaaa acacgtttgt cagcaaaaaa cttcgagatt taattattga ctttcgtgaa    1800
cctcagttta tatcctacct tagttctgtt cttccacatg atgcaaagga tacagttgcc    1860
tgcattctaa agggtttgaa taagcctcag aggcaagcga tgaaaaaggt acttctttca    1920
aaagactaca cactcatcgt gggtatgcct gggacaggaa aaacaactac gatatgtact    1980
ctcgtaagaa ttctctacgc ctgtggtttt agcgttttgt tgaccagcta tacacactct    2040
gctgttgaca atattctttt gaagttagcc aagtttaaaa taggattttt gcgtttgggt    2100
cagattcaga aggttcatcc agctatccag caatttacag agcaagaaat ttgcagatca    2160
aagtccatta aatccttagc tcttctagaa gaactctaca atagtcaact tatagttgca    2220
acaacatgta tgggaataaa ccatccaata ttttcccgta aaattttga ttttgtatt       2280 gtggatgaag cctctcaaat tagccaacca atttgtctgg ccccctttt tttttcacgg       2340 agatttgtgt tagtggggga ccatcagcag cttcctcccc tggtgctaaa ccgtgaagca    2400
agagctcttg gcatgagtga aagcttattc aagaggctgg agcagaataa gagtgctgtt    2460
gtacagttaa ccgtgcagta cagaatgaac agtaaaatta tgtccttaag taataagctg    2520
acctatgagg gcaagctgga gtgtggatca gacaaagtgg ccaatgcagt gataaaccta    2580 cgtcactta aagatgtgaa gctggaactg gaattttatg ctgactattc tgataatcct      2640
tggttgatgg gagtatttga acccaacaat cctgtttgtt tccttaatac agacaaggtt    2700
ccagcgccag aacaagttga aaaaggtggt gtgagcaatg taacagaagc caaactcata    2760
gttttcctaa cctccatttt tgttaaggct ggatgcagtc cctctgatat tggtattatt    2820
gcaccgtaca ggcagcaatt aaagatcatc aatgatttat tggcacgttc tattgggatg    2880
gtcgaagtta atacagtaga caaataccaa ggaagggaca aaagtattgt cctagtatct    2940
tttgttagaa gtaataagga tggaactgtt ggtgaactct tgaaagattg gcgacgtctt    3000
aatgttgcta taaccagagc caaacataaa ctgattcttc tggggtgtgt gccctcacta    3060
aattgctatc ctcctttgga gaagctgctt aatcatttaa actcagaaaa attaatcatt    3120
gatcttccat caagagaaca tgaaagtctt tgccacatat tgggtgactt tcaaagagaa    3180
taa                                                                  3183
```

```
<210> SEQ ID NO 14
<211> LENGTH: 1060
<212> TYPE: PRT
<213> ORGANISM: Homo sapiens

<400> SEQUENCE: 14

Met Glu Gln Leu Asn Glu Leu Glu Leu Leu Met Glu Lys Ser Phe Trp
1               5                   10                  15

Glu Glu Ala Glu Leu Pro Ala Glu Leu Phe Gln Lys Lys Val Val Ala
            20                  25                  30

Ser Phe Pro Arg Thr Val Leu Ser Thr Gly Met Asp Asn Arg Tyr Leu
        35                  40                  45

Val Leu Ala Val Asn Thr Val Gln Asn Lys Glu Gly Asn Cys Glu Lys
    50                  55                  60

Arg Leu Val Ile Thr Ala Ser Gln Ser Leu Glu Asn Lys Glu Leu Cys
65                  70                  75                  80

Ile Leu Arg Asn Asp Trp Cys Ser Val Pro Val Glu Pro Gly Asp Ile
                85                  90                  95

Ile His Leu Glu Gly Asp Cys Thr Ser Asp Thr Trp Ile Ile Asp Lys
            100                 105                 110

Asp Phe Gly Tyr Leu Ile Leu Tyr Pro Asp Met Leu Ile Ser Gly Thr
        115                 120                 125

Ser Ile Ala Ser Ser Ile Arg Cys Met Arg Arg Ala Val Leu Ser Glu
    130                 135                 140

Thr Phe Arg Ser Ser Asp Pro Ala Thr Arg Gln Met Leu Ile Gly Thr
145                 150                 155                 160

Val Leu His Glu Val Phe Gln Lys Ala Ile Asn Asn Ser Phe Ala Pro
                165                 170                 175

Glu Lys Leu Gln Glu Leu Ala Phe Gln Thr Ile Gln Glu Ile Arg His
            180                 185                 190

Leu Lys Glu Met Tyr Arg Leu Asn Leu Ser Gln Asp Glu Ile Lys Gln
            195                 200                 205

Glu Val Glu Asp Tyr Leu Pro Ser Phe Cys Lys Trp Ala Gly Asp Phe
    210                 215                 220

Met His Lys Asn Thr Ser Thr Asp Phe Pro Gln Met Gln Leu Ser Leu
225                 230                 235                 240

Pro Ser Asp Asn Ser Lys Asp Asn Ser Thr Cys Asn Ile Glu Val Val
                245                 250                 255

Lys Pro Met Asp Ile Glu Glu Ser Ile Trp Ser Pro Arg Phe Gly Leu
            260                 265                 270

Lys Gly Lys Ile Asp Val Thr Val Gly Val Lys Ile His Arg Gly Tyr
        275                 280                 285

Lys Thr Lys Tyr Lys Ile Met Pro Leu Glu Leu Lys Thr Gly Lys Glu
    290                 295                 300

Ser Asn Ser Ile Glu His Arg Ser Gln Val Val Leu Tyr Thr Leu Leu
305                 310                 315                 320

Ser Gln Glu Arg Arg Ala Asp Pro Glu Ala Gly Leu Leu Leu Tyr Leu
                325                 330                 335

Lys Thr Gly Gln Met Tyr Pro Val Pro Ala Asn His Leu Asp Lys Arg
            340                 345                 350

Glu Leu Leu Lys Leu Arg Asn Gln Met Ala Phe Ser Leu Phe His Arg
            355                 360                 365

Ile Ser Lys Ser Ala Thr Arg Gln Lys Thr Gln Leu Ala Ser Leu Pro
```

-continued

```
          370                 375                 380

Gln Ile Ile Glu Glu Glu Lys Thr Cys Lys Tyr Cys Ser Gln Ile Gly
385                 390                 395                 400

Asn Cys Ala Leu Tyr Ser Arg Ala Val Glu Gln Gln Met Asp Cys Ser
                405                 410                 415

Ser Val Pro Ile Val Met Leu Pro Lys Ile Glu Glu Glu Thr Gln His
                420                 425                 430

Leu Lys Gln Thr His Leu Glu Tyr Phe Ser Leu Trp Cys Leu Met Leu
                435                 440                 445

Thr Leu Glu Ser Gln Ser Lys Asp Asn Lys Lys Asn His Gln Asn Ile
                450                 455                 460

Trp Leu Met Pro Ala Ser Glu Met Glu Lys Ser Gly Ser Cys Ile Gly
465                 470                 475                 480

Asn Leu Ile Arg Met Glu His Val Lys Ile Val Cys Asp Gly Gln Tyr
                485                 490                 495

Leu His Asn Phe Gln Cys Lys His Gly Ala Ile Pro Val Thr Asn Leu
                500                 505                 510

Met Ala Gly Asp Arg Val Ile Val Ser Gly Glu Glu Arg Ser Leu Phe
                515                 520                 525

Ala Leu Ser Arg Gly Tyr Val Lys Glu Ile Asn Met Thr Thr Val Thr
                530                 535                 540

Cys Leu Leu Asp Arg Asn Leu Ser Val Leu Pro Glu Ser Thr Leu Phe
545                 550                 555                 560

Arg Leu Asp Gln Glu Glu Lys Asn Cys Asp Ile Asp Thr Pro Leu Gly
                565                 570                 575

Asn Leu Ser Lys Leu Met Glu Asn Thr Phe Val Ser Lys Lys Leu Arg
                580                 585                 590

Asp Leu Ile Ile Asp Phe Arg Glu Pro Gln Phe Ile Ser Tyr Leu Ser
                595                 600                 605

Ser Val Leu Pro His Asp Ala Lys Asp Thr Val Ala Cys Ile Leu Lys
                610                 615                 620

Gly Leu Asn Lys Pro Gln Arg Gln Ala Met Lys Lys Val Leu Leu Ser
625                 630                 635                 640

Lys Asp Tyr Thr Leu Ile Val Gly Met Pro Gly Thr Gly Lys Thr Thr
                645                 650                 655

Thr Ile Cys Thr Leu Val Arg Ile Leu Tyr Ala Cys Gly Phe Ser Val
                660                 665                 670

Leu Leu Thr Ser Tyr Thr His Ser Ala Val Asp Asn Ile Leu Leu Lys
                675                 680                 685

Leu Ala Lys Phe Lys Ile Gly Phe Leu Arg Leu Gly Gln Ile Gln Lys
                690                 695                 700

Val His Pro Ala Ile Gln Gln Phe Thr Glu Gln Glu Ile Cys Arg Ser
705                 710                 715                 720

Lys Ser Ile Lys Ser Leu Ala Leu Leu Glu Glu Leu Tyr Asn Ser Gln
                725                 730                 735

Leu Ile Val Ala Thr Thr Cys Met Gly Ile Asn His Pro Ile Phe Ser
                740                 745                 750

Arg Lys Ile Phe Asp Phe Cys Ile Val Asp Glu Ala Ser Gln Ile Ser
                755                 760                 765

Gln Pro Ile Cys Leu Gly Pro Leu Phe Phe Ser Arg Arg Phe Val Leu
                770                 775                 780

Val Gly Asp His Gln Gln Leu Pro Pro Leu Val Leu Asn Arg Glu Ala
785                 790                 795                 800
```

```
Arg Ala Leu Gly Met Ser Glu Ser Leu Phe Lys Arg Leu Glu Gln Asn
                805                 810                 815

Lys Ser Ala Val Val Gln Leu Thr Val Gln Tyr Arg Met Asn Ser Lys
                820                 825                 830

Ile Met Ser Leu Ser Asn Lys Leu Thr Tyr Glu Gly Lys Leu Glu Cys
                835                 840                 845

Gly Ser Asp Lys Val Ala Asn Ala Val Ile Asn Leu Arg His Phe Lys
        850                 855                 860

Asp Val Lys Leu Glu Leu Glu Phe Tyr Ala Asp Tyr Ser Asp Asn Pro
865                 870                 875                 880

Trp Leu Met Gly Val Phe Glu Pro Asn Asn Pro Val Cys Phe Leu Asn
                885                 890                 895

Thr Asp Lys Val Pro Ala Pro Glu Gln Val Glu Lys Gly Gly Val Ser
                900                 905                 910

Asn Val Thr Glu Ala Lys Leu Ile Val Phe Leu Thr Ser Ile Phe Val
                915                 920                 925

Lys Ala Gly Cys Ser Pro Ser Asp Ile Gly Ile Ile Ala Pro Tyr Arg
        930                 935                 940

Gln Gln Leu Lys Ile Ile Asn Asp Leu Leu Ala Arg Ser Ile Gly Met
945                 950                 955                 960

Val Glu Val Asn Thr Val Asp Lys Tyr Gln Gly Arg Asp Lys Ser Ile
                965                 970                 975

Val Leu Val Ser Phe Val Arg Ser Asn Lys Asp Gly Thr Val Gly Glu
                980                 985                 990

Leu Leu Lys Asp Trp Arg Arg Leu  Asn Val Ala Ile Thr  Arg Ala Lys
        995                 1000                 1005

His Lys  Leu Ile Leu Leu Gly  Cys Val Pro Ser Leu  Asn Cys Tyr
    1010                 1015                 1020

Pro Pro  Leu Glu Lys Leu Leu  Asn His Leu Asn Ser  Glu Lys Leu
    1025                 1030                 1035

Ile Ile  Asp Leu Pro Ser Arg  Glu His Glu Ser Leu  Cys His Ile
    1040                 1045                 1050

Leu Gly  Asp Phe Gln Arg Glu
    1055                 1060
```

```
<210> SEQ ID NO 15
<211> LENGTH: 2694
<212> TYPE: DNA
<213> ORGANISM: Homo sapiens

<400> SEQUENCE: 15
atgaacatct cgggaagcag ctgtggaagc cctaactctg cagatacatc tagtgacttt      60
aaggaccttt ggacaaaact aaaagaatgt catgatagag aagtacaagg tttacaagta     120
aaagtaacca agctaaaaca ggaacgaatc ttagatgcac aaagactaga agaattcttc     180
accaaaaatc aacagctgag ggaacagcag aaagtccttc atgaaaccat taaagtttta     240
gaagatcggt taagagcagg cttatgtgat cgctgtgcag taactgaaga acatatgcgg     300
aaaaaacagc aagagtttga aaatatccgg cagcagaatc ttaaacttat tacagaactt     360
atgaatgaaa ggaatactct acaggaagaa aataaaaagc tttctgaaca actccagcag     420
aaaattgaga atgatcaaca gcatcaagca gctgagcttg aatgtgagga agacgttatt     480
ccagattcac cgataacagc cttctcattt tctggcgtta accggctacg aagaaaggag     540
aacccccatg tccgatacat agaacaaaca catactaaat tggagcactc tgtgtgtgca     600
```

-continued

```
aatgaaatga gaaaagtttc caagtcttca actcatccac aacataatcc taatgaaaat       660
gaaattctag tagctgacac ttatgaccaa agtcaatctc caatggccaa agcacatgga       720
acaagcagct atacccctga taagtcatct tttaatttag ctacagttgt tgctgaaaca       780
cttggacttg gtgttcaaga agaatctgaa actcaaggtc ccatgagccc ccttggtgat       840
gagctctacc actgtctgga aggaaatcac aagaaacagc cttttgagga atctacaaga       900
aatactgaag atagtttaag attttcagat tctacttcaa agactcctcc tcaagaagaa       960
ttacctactc gagtgtcatc tcctgtattt ggagctacct ctagtatcaa aagtggttta      1020
gatttgaata caagtttgtc cccttctctt ttacagcctg ggaaaaaaaa acatctgaaa      1080
acactccctt ttagcaacac ttgtatatct agattagaaa aaactagatc aaaatctgaa      1140
gatagtgccc ttttcacaca tcacagtctt gggtctgaag tgaacaagat cattatccag      1200
tcatctaata aacagatact tataaataaa aatataagtg aatccctagg tgaacagaat      1260
aggactgagt acggtaaaga ttctaacact gataaacatt tggagcccct gaaatcattg      1320
ggaggccgaa catccaaaag gaagaaaact gaggaagaaa gtgaacatga agtaagctgc      1380
ccccaagctt cttttgataa agaaaatgct ttcccttttc caatggataa tcagttttcc      1440
atgaatggag actgtgtgat ggataaacct ctggatctgt ctgatcgatt ttcagctatt      1500
cagcgtcaag agaaaagcca aggaagtgag acttctaaaa acaaatttag gcaagtgact      1560
ctttatgagg cttttgaagac cattccaaag ggcttttcct caagccgtaa ggcctcagat      1620
ggcaactgca cgttgcccaa agattcccca ggggagccct gttcacagga atgcatcatc      1680
cttcagccct tgaataaatg ctctccagac aataaaccat cattacaaat aaaagaagaa      1740
aatgctgtct ttaaaattcc tctacgtcca cgtgaaagtt tggagactga gaatgtttta      1800
gatgacataa agagtgctgg ttctcatgag ccaataaaaa tacaaaccag gtcagaccat      1860
ggaggatgtg aacttgcatc agttcttcag ttaaatccat gtagaactgg taaaataaag      1920
tctctacaaa acaaccaaga tgtatccttt gaaaatatcc agtggagtat agatccggga      1980 gcagacccttt ctcagtataa aatggatgtt actgtaatag atacaaagga tggcagtcag      2040
tcaaaattag gaggagagac agtggacatg gactgtacat tggttagtga aaccgttctc      2100
ttaaaaatga gaagcaaga gcagaaggga gaaaaaagtt caaatgaaga aagaaaaatg      2160
aatgatagct tggaagatat gtttgatcgg acaacacatg aagagtatga atcctgtttg      2220
gcagacagtt tctcccaagc agcagatgaa gaggaggaat tgtctactgc cacaaagaaa      2280
ctacacactc atggtgataa acaagacaaa gtcaagcaga aagcgtttgt ggagccgtat      2340
tttaaaggtg atgaaagaga gactagcttg caaaattttc ctcatattga ggtggttcgg      2400
aaaaaagagg agagaagaaa actgcttggg cacacgtgta aggaatgtga aatttattat      2460
gcagatatgc cagcagaaga aagagaaaag aaattggctt cctgctcaag acaccgattc      2520
cgctacattc cacccaacac accagagaat ttttgggaag ttggtttttcc ttccactcag      2580 acttgtatgg aaagaggtta tattaaggaa gatcttgatc cttgtcctcg tccaaaaaga      2640
cgtcagcctt acaacgcaat attttctcca aaaggcaagg agcagaagac atag           2694
```

<210> SEQ ID NO 16
<211> LENGTH: 897
<212> TYPE: PRT
<213> ORGANISM: Homo sapiens

<400> SEQUENCE: 16

```
Met Asn Ile Ser Gly Ser Ser Cys Gly Ser Pro Asn Ser Ala Asp Thr
1               5                   10                  15

Ser Ser Asp Phe Lys Asp Leu Trp Thr Lys Leu Lys Glu Cys His Asp
            20                  25                  30

Arg Glu Val Gln Gly Leu Gln Val Lys Val Thr Lys Leu Lys Gln Glu
            35                  40                  45

Arg Ile Leu Asp Ala Gln Arg Leu Glu Glu Phe Phe Thr Lys Asn Gln
    50                  55                  60

Gln Leu Arg Glu Gln Gln Lys Val Leu His Glu Thr Ile Lys Val Leu
65                  70                  75                  80

Glu Asp Arg Leu Arg Ala Gly Leu Cys Asp Arg Cys Ala Val Thr Glu
            85                  90                  95

Glu His Met Arg Lys Lys Gln Gln Glu Phe Glu Asn Ile Arg Gln Gln
            100                 105                 110

Asn Leu Lys Leu Ile Thr Glu Leu Met Asn Glu Arg Asn Thr Leu Gln
        115                 120                 125

Glu Glu Asn Lys Lys Leu Ser Glu Gln Leu Gln Gln Lys Ile Glu Asn
    130                 135                 140

Asp Gln Gln His Gln Ala Ala Glu Leu Glu Cys Glu Glu Asp Val Ile
145                 150                 155                 160

Pro Asp Ser Pro Ile Thr Ala Phe Ser Phe Ser Gly Val Asn Arg Leu
            165                 170                 175

Arg Arg Lys Glu Asn Pro His Val Arg Tyr Ile Glu Gln Thr His Thr
            180                 185                 190

Lys Leu Glu His Ser Val Cys Ala Asn Glu Met Arg Lys Val Ser Lys
        195                 200                 205

Ser Ser Thr His Pro Gln His Asn Pro Asn Glu Asn Glu Ile Leu Val
    210                 215                 220

Ala Asp Thr Tyr Asp Gln Ser Gln Ser Pro Met Ala Lys Ala His Gly
225                 230                 235                 240

Thr Ser Ser Tyr Thr Pro Asp Lys Ser Ser Phe Asn Leu Ala Thr Val
            245                 250                 255

Val Ala Glu Thr Leu Gly Leu Gly Val Gln Glu Glu Ser Glu Thr Gln
            260                 265                 270

Gly Pro Met Ser Pro Leu Gly Asp Glu Leu Tyr His Cys Leu Glu Gly
            275                 280                 285

Asn His Lys Lys Gln Pro Phe Glu Glu Ser Thr Arg Asn Thr Glu Asp
    290                 295                 300

Ser Leu Arg Phe Ser Asp Ser Thr Ser Lys Thr Pro Pro Gln Glu Glu
305                 310                 315                 320

Leu Pro Thr Arg Val Ser Ser Pro Val Phe Gly Ala Thr Ser Ser Ile
            325                 330                 335

Lys Ser Gly Leu Asp Leu Asn Thr Ser Leu Ser Pro Ser Leu Leu Gln
        340                 345                 350

Pro Gly Lys Lys Lys His Leu Lys Thr Leu Pro Phe Ser Asn Thr Cys
        355                 360                 365

Ile Ser Arg Leu Glu Lys Thr Arg Ser Lys Ser Glu Asp Ser Ala Leu
    370                 375                 380

Phe Thr His His Ser Leu Gly Ser Glu Val Asn Lys Ile Ile Ile Gln
385                 390                 395                 400

Ser Ser Asn Lys Gln Ile Leu Ile Asn Lys Asn Ile Ser Glu Ser Leu
            405                 410                 415

Gly Glu Gln Asn Arg Thr Glu Tyr Gly Lys Asp Ser Asn Thr Asp Lys
```

```
              420             425             430
His Leu Glu Pro Leu Lys Ser Leu Gly Gly Arg Thr Ser Lys Arg Lys
         435             440             445

Lys Thr Glu Glu Glu Ser Glu His Glu Val Ser Cys Pro Gln Ala Ser
         450             455             460

Phe Asp Lys Glu Asn Ala Phe Pro Phe Pro Met Asp Asn Gln Phe Ser
465             470             475             480

Met Asn Gly Asp Cys Val Met Asp Lys Pro Leu Asp Leu Ser Asp Arg
             485             490             495

Phe Ser Ala Ile Gln Arg Gln Glu Lys Ser Gln Gly Ser Glu Thr Ser
             500             505             510

Lys Asn Lys Phe Arg Gln Val Thr Leu Tyr Glu Ala Leu Lys Thr Ile
         515             520             525

Pro Lys Gly Phe Ser Ser Ser Arg Lys Ala Ser Asp Gly Asn Cys Thr
         530             535             540

Leu Pro Lys Asp Ser Pro Gly Glu Pro Cys Ser Gln Glu Cys Ile Ile
545             550             555             560

Leu Gln Pro Leu Asn Lys Cys Ser Pro Asp Asn Lys Pro Ser Leu Gln
             565             570             575

Ile Lys Glu Glu Asn Ala Val Phe Lys Ile Pro Leu Arg Pro Arg Glu
             580             585             590

Ser Leu Glu Thr Glu Asn Val Leu Asp Asp Ile Lys Ser Ala Gly Ser
         595             600             605

His Glu Pro Ile Lys Ile Gln Thr Arg Ser Asp His Gly Gly Cys Glu
         610             615             620

Leu Ala Ser Val Leu Gln Leu Asn Pro Cys Arg Thr Gly Lys Ile Lys
625             630             635             640

Ser Leu Gln Asn Asn Gln Asp Val Ser Phe Glu Asn Ile Gln Trp Ser
             645             650             655

Ile Asp Pro Gly Ala Asp Leu Ser Gln Tyr Lys Met Asp Val Thr Val
             660             665             670

Ile Asp Thr Lys Asp Gly Ser Gln Ser Lys Leu Gly Gly Glu Thr Val
         675             680             685

Asp Met Asp Cys Thr Leu Val Ser Glu Thr Val Leu Leu Lys Met Lys
         690             695             700

Lys Gln Glu Gln Lys Gly Glu Lys Ser Ser Asn Glu Glu Arg Lys Met
705             710             715             720

Asn Asp Ser Leu Glu Asp Met Phe Asp Arg Thr Thr His Glu Glu Tyr
             725             730             735

Glu Ser Cys Leu Ala Asp Ser Phe Ser Gln Ala Ala Asp Glu Glu Glu
             740             745             750

Glu Leu Ser Thr Ala Thr Lys Lys Leu His Thr His Gly Asp Lys Gln
         755             760             765

Asp Lys Val Lys Gln Lys Ala Phe Val Glu Pro Tyr Phe Lys Gly Asp
         770             775             780

Glu Arg Glu Thr Ser Leu Gln Asn Phe Pro His Ile Glu Val Val Arg
785             790             795             800

Lys Lys Glu Glu Arg Arg Lys Leu Leu Gly His Thr Cys Lys Glu Cys
             805             810             815

Glu Ile Tyr Tyr Ala Asp Met Pro Ala Glu Glu Arg Glu Lys Lys Leu
             820             825             830

Ala Ser Cys Ser Arg His Arg Phe Arg Tyr Ile Pro Pro Asn Thr Pro
         835             840             845
```

-continued

```
Glu Asn Phe Trp Glu Val Gly Phe Pro Ser Thr Gln Thr Cys Met Glu
    850                 855                 860

Arg Gly Tyr Ile Lys Glu Asp Leu Asp Pro Cys Pro Arg Pro Lys Arg
865                 870                 875                 880

Arg Gln Pro Tyr Asn Ala Ile Phe Ser Pro Lys Gly Lys Glu Gln Lys
                885                 890                 895

Thr

<210> SEQ ID NO 17
<211> LENGTH: 2541
<212> TYPE: DNA
<213> ORGANISM: Homo sapiens

<400> SEQUENCE: 17
atggggatac agggattgct acaatttatc aaagaagctt cagaacccat ccatgtgagg      60
aagtataaag ggcaggtagt agctgtggat acatattgct ggcttcacaa aggagctatt     120
gcttgtgctg aaaaactagc caaaggtgaa cctactgata ggtatgtagg attttgtatg     180
aaatttgtaa atatgttact atctcatggg atcaagccta ttctcgtatt tgatggatgt     240
actttacctt ctaaaaagga agtagagaga tctagaagag aaagacgaca agccaatctt     300
cttaagggaa agcaacttct tcgtgagggg aaagtctcgg aagctcgaga gtgtttcacc     360
cggtctatca atatcacaca tgccatggcc cacaaagtaa ttaaagctgc ccggtctcag     420
ggggtagatt gcctcgtggc tccctatgaa gctgatgcgc agttggccta tcttaacaaa     480
gcgggaattg tgcaagccat aattacagag gactcggatc tcctagcttt tggctgtaaa     540
aaggtaattt taaagatgga ccagtttgga aatggacttg aaattgatca agctcggcta     600
ggaatgtgca gacagcttgg ggatgtattc acggaagaga gtttcgtta catgtgtatt     660 ctttcaggtt gtgactacct gtcatcactg cgtgggattg gattagcaaa ggcatgcaaa     720
gtcctaagac tagccaataa tccagatata gtaaaggtta tcaagaaaat tggacattat     780
ctcaagatga atatcacggt accagaggat tacatcaacg ggtttattcg ggccaacaat     840
accttcctct atcagctagt ttttgatccc atcaaaagga aacttattcc tctgaacgcc     900
tatgaagatg atgttgatcc tgaaacacta agctacgctg ggcaatatgt tgatgattcc     960
atagctcttc aaatagcact tggaaataaa gatataaata cttttgaaca gatcgatgac    1020
tacaatccag acactgctat gcctgcccat tcaagaagtc atagttggga tgacaaaaca    1080
tgtcaaaagt cagctaatgt tagcagcatt tggcatagga attactctcc cagaccagag    1140
tcgggtactg tttcagatgc cccacaattg aaggaaaatc caagtactgt gggagtggaa    1200
cgagtgatta gtactaaagg gttaaatctc ccaaggaaat catccattgt gaaaagacca    1260
agaagtgcag agctgtcaga agatgacctg ttgagtcagt attctctttc atttacgaag    1320
aagaccaaga aaaatagctc tgaaggcaat aaatcattga gcttttctga gtgtttgtg     1380 cctgacctgg taaatggacc tactaacaaa agagtgtaa gcactccacc taggacgaga    1440
aataaatttg caacattttt acaaaggaaa aatgaagaaa gtggtgcagt tgtggttcca    1500
gggaccagaa gcaggttttt ttgcagttca gattctactg actgtgtatc aaacaaagtg    1560
agcatccagc ctctggatga aactgctgtc acagataaag agaacaatct gcatgaatca    1620
gagtatggag accaagaagg caagagactg gttgacacag atgtagcacg taattcaagt    1680
gatgacattc gaataatca tattccaggt gatcatattc cagacaaggc aacagtgttt    1740
acagatgaag agtcctactc ttttgagagc agcaaattta caaggaccat ttcaccaccc    1800
```

-continued

```
actttgggaa cactaagaag ttgtttagt tggtctggag gtcttggaga tttttcaaga   1860
acgccgagcc cctctccaag cacagcattg cagcagttcc gaagaaagag cgattccccc   1920
acctctttgc ctgagaataa tatgtctgat gtgtcgcagt aaagagcga ggagtccagt   1980 gacgatgagt ctcatccctt acgagaagag gcatgttctt cacagtccca ggaaagtgga   2040
gaattctcac tgcagagttc aaatgcatca aagctttctc agtgctctag taaggactct   2100
gattcagagg aatctgattg caatattaag ttacttgaca gtcaaagtga ccagacctcc   2160
aagctacgtt tatctcattt ctcaaaaaaa gacacacctc taaggaacaa ggttcctggg   2220
ctatataagt ccagttctgc agactctctt tctacaacca agatcaaacc tctaggacct   2280
gccagagcca gtgggctgag caagaagccg gcaagcatcc agaagagaaa gcatcataat   2340
gccgagaaca agccggggtt acagatcaaa ctcaatgagc tctggaaaaa ctttggattt   2400
aaaaaagatt ctgaaaagct tcctccttgt aagaaacccc tgtccccagt cagagataac   2460
atccaactaa ctccagaagc ggaagaggat atatttaaca aacctgaatg tggccgtgtt   2520
caaagagcaa tattccagta a                                              2541
```

```
<210> SEQ ID NO 18
<211> LENGTH: 846
<212> TYPE: PRT
<213> ORGANISM: Homo sapiens

<400> SEQUENCE: 18

Met Gly Ile Gln Gly Leu Leu Gln Phe Ile Lys Glu Ala Ser Glu Pro
1               5                   10                  15

Ile His Val Arg Lys Tyr Lys Gly Gln Val Val Ala Val Asp Thr Tyr
                20                  25                  30

Cys Trp Leu His Lys Gly Ala Ile Ala Cys Ala Glu Lys Leu Ala Lys
            35                  40                  45

Gly Glu Pro Thr Asp Arg Tyr Val Gly Phe Cys Met Lys Phe Val Asn
        50                  55                  60

Met Leu Leu Ser His Gly Ile Lys Pro Ile Leu Val Phe Asp Gly Cys
65                  70                  75                  80

Thr Leu Pro Ser Lys Lys Glu Val Glu Arg Ser Arg Arg Glu Arg Arg
                85                  90                  95

Gln Ala Asn Leu Leu Lys Gly Lys Gln Leu Leu Arg Glu Gly Lys Val
            100                 105                 110

Ser Glu Ala Arg Glu Cys Phe Thr Arg Ser Ile Asn Ile Thr His Ala
        115                 120                 125

Met Ala His Lys Val Ile Lys Ala Ala Arg Ser Gln Gly Val Asp Cys
    130                 135                 140

Leu Val Ala Pro Tyr Glu Ala Asp Ala Gln Leu Ala Tyr Leu Asn Lys
145                 150                 155                 160

Ala Gly Ile Val Gln Ala Ile Ile Thr Glu Asp Ser Asp Leu Leu Ala
                165                 170                 175

Phe Gly Cys Lys Lys Val Ile Leu Lys Met Asp Gln Phe Gly Asn Gly
            180                 185                 190

Leu Glu Ile Asp Gln Ala Arg Leu Gly Met Cys Arg Gln Leu Gly Asp
        195                 200                 205

Val Phe Thr Glu Glu Lys Phe Arg Tyr Met Cys Ile Leu Ser Gly Cys
    210                 215                 220

Asp Tyr Leu Ser Ser Leu Arg Gly Ile Gly Leu Ala Lys Ala Cys Lys
225                 230                 235                 240
```

-continued

```
Val Leu Arg Leu Ala Asn Asn Pro Asp Ile Val Lys Val Ile Lys Lys
            245                 250                 255

Ile Gly His Tyr Leu Lys Met Asn Ile Thr Val Pro Glu Asp Tyr Ile
            260                 265                 270

Asn Gly Phe Ile Arg Ala Asn Asn Thr Phe Leu Tyr Gln Leu Val Phe
            275                 280                 285

Asp Pro Ile Lys Arg Lys Leu Ile Pro Leu Asn Ala Tyr Glu Asp Asp
        290                 295                 300

Val Asp Pro Glu Thr Leu Ser Tyr Ala Gly Gln Tyr Val Asp Asp Ser
305                 310                 315                 320

Ile Ala Leu Gln Ile Ala Leu Gly Asn Lys Asp Ile Asn Thr Phe Glu
            325                 330                 335

Gln Ile Asp Asp Tyr Asn Pro Asp Thr Ala Met Pro Ala His Ser Arg
            340                 345                 350

Ser His Ser Trp Asp Asp Lys Thr Cys Gln Lys Ser Ala Asn Val Ser
            355                 360                 365

Ser Ile Trp His Arg Asn Tyr Ser Pro Arg Pro Glu Ser Gly Thr Val
            370                 375                 380

Ser Asp Ala Pro Gln Leu Lys Glu Asn Pro Ser Thr Val Gly Val Glu
385                 390                 395                 400

Arg Val Ile Ser Thr Lys Gly Leu Asn Leu Pro Arg Lys Ser Ser Ile
            405                 410                 415

Val Lys Arg Pro Arg Ser Ala Glu Leu Ser Glu Asp Asp Leu Leu Ser
            420                 425                 430

Gln Tyr Ser Leu Ser Phe Thr Lys Lys Thr Lys Lys Asn Ser Ser Glu
            435                 440                 445

Gly Asn Lys Ser Leu Ser Phe Ser Glu Val Phe Val Pro Asp Leu Val
        450                 455                 460

Asn Gly Pro Thr Asn Lys Lys Ser Val Ser Thr Pro Pro Arg Thr Arg
465                 470                 475                 480

Asn Lys Phe Ala Thr Phe Leu Gln Arg Lys Asn Glu Glu Ser Gly Ala
            485                 490                 495

Val Val Val Pro Gly Thr Arg Ser Arg Phe Phe Cys Ser Ser Asp Ser
            500                 505                 510

Thr Asp Cys Val Ser Asn Lys Val Ser Ile Gln Pro Leu Asp Glu Thr
            515                 520                 525

Ala Val Thr Asp Lys Glu Asn Asn Leu His Glu Ser Glu Tyr Gly Asp
        530                 535                 540

Gln Glu Gly Lys Arg Leu Val Asp Thr Asp Val Ala Arg Asn Ser Ser
545                 550                 555                 560

Asp Asp Ile Pro Asn Asn His Ile Pro Gly Asp His Ile Pro Asp Lys
            565                 570                 575

Ala Thr Val Phe Thr Asp Glu Glu Ser Tyr Ser Phe Glu Ser Ser Lys
            580                 585                 590

Phe Thr Arg Thr Ile Ser Pro Pro Thr Leu Gly Thr Leu Arg Ser Cys
            595                 600                 605

Phe Ser Trp Ser Gly Gly Leu Gly Asp Phe Ser Arg Thr Pro Ser Pro
        610                 615                 620

Ser Pro Ser Thr Ala Leu Gln Gln Phe Arg Arg Lys Ser Asp Ser Pro
625                 630                 635                 640

Thr Ser Leu Pro Glu Asn Asn Met Ser Asp Val Ser Gln Leu Lys Ser
            645                 650                 655
```

-continued

```
Glu Glu Ser Ser Asp Asp Glu Ser His Pro Leu Arg Glu Glu Ala Cys
            660             665             670

Ser Ser Gln Ser Gln Glu Ser Gly Glu Phe Ser Leu Gln Ser Ser Asn
        675             680             685

Ala Ser Lys Leu Ser Gln Cys Ser Ser Lys Asp Ser Asp Ser Glu Glu
    690             695             700

Ser Asp Cys Asn Ile Lys Leu Leu Asp Ser Gln Ser Asp Gln Thr Ser
705             710             715             720

Lys Leu Arg Leu Ser His Phe Ser Lys Lys Asp Thr Pro Leu Arg Asn
            725             730             735

Lys Val Pro Gly Leu Tyr Lys Ser Ser Ser Ala Asp Ser Leu Ser Thr
        740             745             750

Thr Lys Ile Lys Pro Leu Gly Pro Ala Arg Ala Ser Gly Leu Ser Lys
        755             760             765

Lys Pro Ala Ser Ile Gln Lys Arg Lys His His Asn Ala Glu Asn Lys
    770             775             780

Pro Gly Leu Gln Ile Lys Leu Asn Glu Leu Trp Lys Asn Phe Gly Phe
785             790             795             800

Lys Lys Asp Ser Glu Lys Leu Pro Pro Cys Lys Lys Pro Leu Ser Pro
            805             810             815

Val Arg Asp Asn Ile Gln Leu Thr Pro Glu Ala Glu Glu Asp Ile Phe
            820             825             830

Asn Lys Pro Glu Cys Gly Arg Val Gln Arg Ala Ile Phe Gln
            835             840             845
```

```
<210> SEQ ID NO 19
<211> LENGTH: 1851
<212> TYPE: DNA
<213> ORGANISM: Homo sapiens

<400> SEQUENCE: 19
atggtcggcc aactgagcga ggggggccatt gcggccatca tgcagaaggg ggatacaaac      60
ataaagccca tcctccaagt catcaacatc cgtcccatta ctacggggaa tagtccgccg     120
cgttatcgac tgctcatgag tgatggattg aacactctat cctctttcat gttggcgaca     180
cagttgaacc ctctcgtgga ggaagaacaa ttgtccagca actgtgtatg ccagattcac     240
agatttattg tgaacactct gaaagacgga aggagagtag ttatcttgat ggaattagaa     300
gttttgaagt cagctgaagc agttggagtg aagattggca atccagtgcc ctataatgaa     360
ggactcgggc agccgcaagt agctcctcca gcgccagcag ccagcccagc agcaagcagc     420
aggccccagc cgcagaatgg aagctcggga atgggttcta ctgtttctaa ggcttatggt     480
gcttcaaaga catttggaaa agctgcaggt cccagcctgt cacacacttc tggggggaaca     540 cagtccaaag tggtgcccat tgccagcctc actccttacc agtccaagtg gaccatttgt     600
gctcgtgtta ccaacaaaag tcagatccgt acctggagca actcccgagg ggaagggaag     660
cttttctccc tagaactggt tgacgaaagt ggtgaaatcc gagctacagc tttcaatgag     720
caagtggaca agttctttcc tcttattgaa gtgaacaagg tgtattattt ctcgaaaggc     780
accctgaaga ttgctaacaa gcagttcaca gctgttaaaa atgactacga gatgaccttc     840
aataacgaga cttccgtcat gccctgtgag gacgaccatc atttacctac ggttcagttt     900
gatttcacgg ggattgatga cctcgagaac aagtcgaaag actcacttgt agacatcatc     960
gggatctgca gagctatga agacgccact aaaatcacag tgaggtctaa caacagagaa    1020
gttgccaaga ggaatatcta cttgatggac acatccggga aggtggtgac tgctacactg    1080
```

```
tggggggaag atgctgataa atttgatggt tctagacagc ccgtgttggc tatcaaagga    1140
gcccgagtct ctgatttcgg tggacggagc ctctccgtgc tgtcttcaag cactatcatt    1200
gcgaatcctg acatcccaga ggcctataag cttcgtggat ggtttgacgc agaaggacaa    1260
gccttagatg gtgtttccat ctctgatcta aagagcggcg gagtcggagg gagtaacacc    1320
aactggaaaa ccttgtatga ggtcaaatcc gagaacctgg gccaaggcga caagccggac    1380
tactttagtt ctgtggccac agtggtgtat cttcgcaaag agaactgcat gtaccaagcc    1440
tgcccgactc aggactgcaa taagaaagtg attgatcaac agaatggatt gtaccgctgt    1500
gagaagtgcg acaccgaatt ccccaatttc aagtaccgca tgatcctgtc agtaaatatt    1560
gcagattttc aagagaatca gtgggtgact tgtttccagg agtctgctga agctatcctt    1620
ggacaaaatg ctgcttatct tggggaatta aaagacaaga atgaacaggc atttgaagaa    1680
gttttccaga atgccaactt ccgatctttc atattcagag tcagggtcaa agtggagacc    1740
tacaacgacg agtctcgaat taaggccact gtgatggacg tgaagcccgt ggactacaga    1800
gagtatggcc gaaggctggt catgagcatc aggagaagtg cattgatgtg a             1851
```

<210> SEQ ID NO 20
<211> LENGTH: 616
<212> TYPE: PRT
<213> ORGANISM: Homo sapiens

<400> SEQUENCE: 20

```
Met Val Gly Gln Leu Ser Glu Gly Ala Ile Ala Ala Ile Met Gln Lys
1               5                   10                  15

Gly Asp Thr Asn Ile Lys Pro Ile Leu Gln Val Ile Asn Ile Arg Pro
                20                  25                  30

Ile Thr Thr Gly Asn Ser Pro Pro Arg Tyr Arg Leu Leu Met Ser Asp
            35                  40                  45

Gly Leu Asn Thr Leu Ser Ser Phe Met Leu Ala Thr Gln Leu Asn Pro
        50                  55                  60

Leu Val Glu Glu Glu Gln Leu Ser Ser Asn Cys Val Cys Gln Ile His
65                  70                  75                  80

Arg Phe Ile Val Asn Thr Leu Lys Asp Gly Arg Arg Val Val Ile Leu
                85                  90                  95

Met Glu Leu Glu Val Leu Lys Ser Ala Glu Ala Val Gly Val Lys Ile
            100                 105                 110

Gly Asn Pro Val Pro Tyr Asn Glu Gly Leu Gly Gln Pro Gln Val Ala
            115                 120                 125

Pro Pro Ala Pro Ala Ala Ser Pro Ala Ala Ser Ser Arg Pro Gln Pro
        130                 135                 140

Gln Asn Gly Ser Ser Gly Met Gly Ser Thr Val Ser Lys Ala Tyr Gly
145                 150                 155                 160

Ala Ser Lys Thr Phe Gly Lys Ala Ala Gly Pro Ser Leu Ser His Thr
                165                 170                 175

Ser Gly Gly Thr Gln Ser Lys Val Val Pro Ile Ala Ser Leu Thr Pro
            180                 185                 190

Tyr Gln Ser Lys Trp Thr Ile Cys Ala Arg Val Thr Asn Lys Ser Gln
            195                 200                 205

Ile Arg Thr Trp Ser Asn Ser Arg Gly Glu Gly Lys Leu Phe Ser Leu
        210                 215                 220

Glu Leu Val Asp Glu Ser Gly Glu Ile Arg Ala Thr Ala Phe Asn Glu
225                 230                 235                 240
```

Gln Val Asp Lys Phe Phe Pro Leu Ile Glu Val Asn Lys Val Tyr Tyr
            245                 250                 255

Phe Ser Lys Gly Thr Leu Lys Ile Ala Asn Lys Gln Phe Thr Ala Val
            260                 265                 270

Lys Asn Asp Tyr Glu Met Thr Phe Asn Asn Glu Thr Ser Val Met Pro
            275                 280                 285

Cys Glu Asp Asp His His Leu Pro Thr Val Gln Phe Asp Phe Thr Gly
            290                 295                 300

Ile Asp Asp Leu Glu Asn Lys Ser Lys Asp Ser Leu Val Asp Ile Ile
305                 310                 315                 320

Gly Ile Cys Lys Ser Tyr Glu Asp Ala Thr Lys Ile Thr Val Arg Ser
            325                 330                 335

Asn Asn Arg Glu Val Ala Lys Arg Asn Ile Tyr Leu Met Asp Thr Ser
            340                 345                 350

Gly Lys Val Val Thr Ala Thr Leu Trp Gly Glu Asp Ala Asp Lys Phe
            355                 360                 365

Asp Gly Ser Arg Gln Pro Val Leu Ala Ile Lys Gly Ala Arg Val Ser
            370                 375                 380

Asp Phe Gly Gly Arg Ser Leu Ser Val Leu Ser Ser Ser Thr Ile Ile
385                 390                 395                 400

Ala Asn Pro Asp Ile Pro Glu Ala Tyr Lys Leu Arg Gly Trp Phe Asp
            405                 410                 415

Ala Glu Gly Gln Ala Leu Asp Gly Val Ser Ile Ser Asp Leu Lys Ser
            420                 425                 430

Gly Gly Val Gly Gly Ser Asn Thr Asn Trp Lys Thr Leu Tyr Glu Val
            435                 440                 445

Lys Ser Glu Asn Leu Gly Gln Gly Asp Lys Pro Asp Tyr Phe Ser Ser
            450                 455                 460

Val Ala Thr Val Val Tyr Leu Arg Lys Glu Asn Cys Met Tyr Gln Ala
465                 470                 475                 480

Cys Pro Thr Gln Asp Cys Asn Lys Lys Val Ile Asp Gln Gln Asn Gly
            485                 490                 495

Leu Tyr Arg Cys Glu Lys Cys Asp Thr Glu Phe Pro Asn Phe Lys Tyr
            500                 505                 510

Arg Met Ile Leu Ser Val Asn Ile Ala Asp Phe Gln Glu Asn Gln Trp
            515                 520                 525

Val Thr Cys Phe Gln Glu Ser Ala Glu Ala Ile Leu Gly Gln Asn Ala
            530                 535                 540

Ala Tyr Leu Gly Glu Leu Lys Asp Lys Asn Glu Gln Ala Phe Glu Glu
545                 550                 555                 560

Val Phe Gln Asn Ala Asn Phe Arg Ser Phe Ile Phe Arg Val Arg Val
            565                 570                 575

Lys Val Glu Thr Tyr Asn Asp Glu Ser Arg Ile Lys Ala Thr Val Met
            580                 585                 590

Asp Val Lys Pro Val Asp Tyr Arg Glu Tyr Gly Arg Arg Leu Val Met
            595                 600                 605

Ser Ile Arg Arg Ser Ala Leu Met
    610                 615

<210> SEQ ID NO 21
<211> LENGTH: 837
<212> TYPE: DNA
<213> ORGANISM: Homo sapiens

```
<400> SEQUENCE: 21
atgggcagag gagacaggaa caagcgtagc atccgtggat tcgaaagcta tggcagctcc      60
tcatacgggg gagccggcgg ctacacgcag tccccggggg gctttggatc gcccgcacct     120
tctcaagccg aaaagaaatc aagagcccga gcccagcaca ttgtgccctg tactatatct     180
cagctgcttt ctgccacttt ggttgatgaa gtgttcagaa ttgggaatgt tgagatttca     240
caggtcacta ttgtggggat catcagacat gcagagaagg ctccaaccaa cattgtttac     300
aaaatagatg acatgacagc tgcacccatg gacgttcgcc agtgggttga cacagatgac     360
accagcagtg aaaacactgt ggttcctcca gaaacatatg tgaaagtggc aggccacctg     420
agatcttttc agaacaaaaa gagcctggta gcctttaaga tcatgcccct ggaggatatg     480
aatgagttca ccacacatat tctggaagtg atcaatgcac acatggtact aagcaaagcc     540
aacagccagc cctcagcagg gagagcacct atcagcaatc caggaatgag tgaagcaggg     600
aactttggtg ggaatagctt catgccagca aatggcctca ctgtggccca aaaccaggtg     660
ttgaatttga ttaaggcttg tccaagacct gaagggttga actttcagga tctcaagaac     720
cagctgaaac acatgtctgt atcctcaatc aagcaagctg tggattttct gagcaatgag     780
gggcacatct attctactgt ggatgatgac cattttaaat ccacagatgc agaataa       837

<210> SEQ ID NO 22
<211> LENGTH: 278
<212> TYPE: PRT
<213> ORGANISM: Homo sapiens

<400> SEQUENCE: 22

Met Gly Arg Gly Asp Arg Asn Lys Arg Ser Ile Arg Gly Phe Glu Ser
1               5                   10                  15

Tyr Gly Ser Ser Ser Tyr Gly Gly Ala Gly Gly Tyr Thr Gln Ser Pro
                20                  25                  30

Gly Gly Phe Gly Ser Pro Ala Pro Ser Gln Ala Glu Lys Lys Ser Arg
            35                  40                  45

Ala Arg Ala Gln His Ile Val Pro Cys Thr Ile Ser Gln Leu Leu Ser
        50                  55                  60

Ala Thr Leu Val Asp Glu Val Phe Arg Ile Gly Asn Val Glu Ile Ser
65                  70                  75                  80

Gln Val Thr Ile Val Gly Ile Ile Arg His Ala Glu Lys Ala Pro Thr
                85                  90                  95

Asn Ile Val Tyr Lys Ile Asp Asp Met Thr Ala Ala Pro Met Asp Val
                100                 105                 110

Arg Gln Trp Val Asp Thr Asp Asp Thr Ser Ser Glu Asn Thr Val Val
            115                 120                 125

Pro Pro Glu Thr Tyr Val Lys Val Ala Gly His Leu Arg Ser Phe Gln
        130                 135                 140

Asn Lys Lys Ser Leu Val Ala Phe Lys Ile Met Pro Leu Glu Asp Met
145                 150                 155                 160

Asn Glu Phe Thr Thr His Ile Leu Glu Val Ile Asn Ala His Met Val
                165                 170                 175

Leu Ser Lys Ala Asn Ser Gln Pro Ser Ala Gly Arg Ala Pro Ile Ser
            180                 185                 190

Asn Pro Gly Met Ser Glu Ala Gly Asn Phe Gly Gly Asn Ser Phe Met
            195                 200                 205

Pro Ala Asn Gly Leu Thr Val Ala Gln Asn Gln Val Leu Asn Leu Ile
        210                 215                 220
```

-continued

```
Lys Ala Cys Pro Arg Pro Glu Gly Leu Asn Phe Gln Asp Leu Lys Asn
225                 230                 235                 240

Gln Leu Lys His Met Ser Val Ser Ser Ile Lys Gln Ala Val Asp Phe
                245                 250                 255

Leu Ser Asn Glu Gly His Ile Tyr Ser Thr Val Asp Asp Asp His Phe
            260                 265                 270

Lys Ser Thr Asp Ala Glu
        275

<210> SEQ ID NO 23
<211> LENGTH: 366
<212> TYPE: DNA
<213> ORGANISM: Homo sapiens

<400> SEQUENCE: 23
atggtggaca tgatggactt gcccaggtcg cgcatcaacg ccggcatgct agctcaattc      60
atcgacaagc tgtctgctt cgtagggagg ctggaaaaga ttcatcccac cggaaaaatg      120
tttattcttt cagatggaga aggaaaaaat ggaaccatcg agttgatgga acccctttgat      180 gaagaaatct ctggaattgt ggaagtggtt ggaagagtaa ccgccaaggc caccatcttg      240
tgtacatctt atgtccagtt taaagaagat agccatcctt ttgatcttgg actttacaat      300
gaagctgtga aaattatcca tgacttccct cagttttatc ctttagggat tgtgcaacat      360
gattga                                                                 366

<210> SEQ ID NO 24
<211> LENGTH: 121
<212> TYPE: PRT
<213> ORGANISM: Homo sapiens

<400> SEQUENCE: 24

Met Val Asp Met Met Asp Leu Pro Arg Ser Arg Ile Asn Ala Gly Met
1               5                   10                  15

Leu Ala Gln Phe Ile Asp Lys Pro Val Cys Phe Val Gly Arg Leu Glu
            20                  25                  30

Lys Ile His Pro Thr Gly Lys Met Phe Ile Leu Ser Asp Gly Glu Gly
        35                  40                  45

Lys Asn Gly Thr Ile Glu Leu Met Glu Pro Leu Asp Glu Glu Ile Ser
    50                  55                  60

Gly Ile Val Glu Val Val Gly Arg Val Thr Ala Lys Ala Thr Ile Leu
65                  70                  75                  80

Cys Thr Ser Tyr Val Gln Phe Lys Glu Asp Ser His Pro Phe Asp Leu
                85                  90                  95

Gly Leu Tyr Asn Glu Ala Val Lys Ile Ile His Asp Phe Pro Gln Phe
            100                 105                 110

Tyr Pro Leu Gly Ile Val Gln His Asp
        115                 120

<210> SEQ ID NO 25
<211> LENGTH: 19
<212> TYPE: RNA
<213> ORGANISM: Artificial Sequence
<220> FEATURE:
<223> OTHER INFORMATION: WRN siRNA1

<400> SEQUENCE: 25
gcaccaaaga gcauuguua                                                    19
```

-continued

```
<210> SEQ ID NO 26
<211> LENGTH: 19
<212> TYPE: RNA
<213> ORGANISM: Artificial Sequence
<220> FEATURE:
<223> OTHER INFORMATION: non-target siRNA1

<400> SEQUENCE: 26
ugguuuacau gucgacuaa                                                    19

<210> SEQ ID NO 27
<211> LENGTH: 19
<212> TYPE: RNA
<213> ORGANISM: Artificial Sequence
<220> FEATURE:
<223> OTHER INFORMATION: non-target siRNA2

<400> SEQUENCE: 27
ugguuuacau guuuucuga                                                    19

<210> SEQ ID NO 28
<211> LENGTH: 19
<212> TYPE: RNA
<213> ORGANISM: Artificial Sequence
<220> FEATURE:
<223> OTHER INFORMATION: WRN siRNA2

<400> SEQUENCE: 28
auacguaacu ccagaauac                                                    19

<210> SEQ ID NO 29
<211> LENGTH: 4299
<212> TYPE: DNA
<213> ORGANISM: Homo sapiens

<400> SEQUENCE: 29
atgagtgaaa aaaaattgga aacaactgca cagcagcgga aatgtcctga atggatgaat       60
gtgcagaata aaagatgtgc tgtagaagaa agaaaggcat gtgttcggaa gagtgttttt      120
gaagatgacc tccccttctt agaattcact ggatccattg tgtatagtta cgatgctagt      180
gattgctctt tcctgtcaga agatattagc atgagtctat cagatgggga tgtggtggga      240
tttgacatgg agtggccacc attatacaat agagggaaac ttggcaaagt tgcactaatt      300
cagttgtgtg tttctgagag caaatgttac ttgttccacg tttcttccat gtcagtttttt     360 ccccagggat taaaaatgtt gcttgaaaat aaagcagtta aaaaggcagg tgtaggaatt      420
gaaggagatc agtggaaact tctacgtgac tttgatatca aattgaagaa ttttgtggag      480
ttgacagatg ttgccaataa aaagctgaaa tgcacagaga cctggagcct taacagtctg      540
gttaaacacc tcttaggtaa acagctcctg aaagacaagt ctatccgctg tagcaattgg      600
agtaaatttc ctctcactga ggaccagaaa ctgtatgcag ccactgatgc ttatgctggt      660
tttattattt accgaaattt agagattttg gatgatactg tgcaaaggtt tgctataaat      720
aaagaggaag aaatcctact tagcgacatg aacaaacagt tgacttcaat ctctgaggaa      780
gtgatggatc tggctaagca tcttcctcat gctttcagta aattggaaaa cccacgggag      840
gtttctatct tactaaagga tatttcagaa aatctatatt cactgaggag gatgataatt      900
gggtctacta acattgagac tgaactgagg cccagcaata atttaaactt attatccttt      960
gaagattcaa ctactggggg agtacaacag aaacaaatta gagaacatga gtttttaatt     1020
cacgttgaag atgaaacatg ggaccccaaca cttgatcatt tagctaaaca tgatggagaa     1080
```

-continued

```
gatgtacttg gaaataaagt ggaacgaaaa gaagatggat ttgaagatgg agtagaagac     1140
aacaaattga aagagaatat ggaaagagct tgtttgatgt cgttagatat tacagaacat     1200
gaactccaaa ttttggaaca gcagtctcag gaagaatatc ttagtgatat tgcttataaa     1260
tctactgagc atttatctcc caatgataat gaaaacgata cgtcctatgt aattgagagt     1320
gatgaagatt tagaaatgga gatgcttaag catttatctc ccaatgataa tgaaaacgat     1380
acgtcctatg taattgagag tgatgaagat ttagaaatgg agatgcttaa gtctttagaa     1440
aacctcaata gtggcacggt agaaccaact cattctaaat gcttaaaaat ggaaagaaat     1500
ctgggtcttc ctactaaaga agaagaagaa gatgatgaaa atgaagctaa tgaaggggaa     1560
gaagatgatg ataaggactt tttgtggcca gcacccaatg aagagcaagt tacttgcctc     1620
aagatgtact ttggccattc cagttttaaa ccagttcagt ggaaagtgat tcattcagta     1680
ttagaagaaa gaagagataa tgttgctgtc atggcaactg gatatggaaa gagtttgtgc     1740
ttccagtatc cacctgttta tgtaggcaag attggccttg ttatctctcc ccttatttct     1800
ctgatggaag accaagtgct acagcttaaa atgtccaaca tcccagcttg cttccttgga     1860
tcagcacagt cagaaaatgt tctaacagat attaaattag gtaaataccg gattgtgtac     1920 gtgaccccg agtattgttc aggtaacatg ggcctgctcc agcaacttga ggctgatatt     1980
ggtatcacgc tcattgctgt ggatgaggct cactgtattt ctgagtgggg gcatgatttt     2040
agggattcat tcaggaagtt gggctcccta aagacagcac tgccaatggt tccaatcgtt     2100
gcacttactg ctactgcaag ttcttcaatc cgggaagaca ttgtacgttg cttaaatctg     2160
agaaatcctc agatcacctg tactggtttt gatcgaccaa acctgtattt agaagttagg     2220
cgaaaaacag ggaatatcct tcaggatctg cagccatttc ttgtcaaaac aagttcccac     2280
tgggaatttg aaggtccaac aatcatctac tgtccttcta gaaaaatgac acaacaagtt     2340
acaggtgaac ttaggaaact gaatctatcc tgtggaacat accatgcggg catgagtttt     2400
agcacaagga aagacattca tcataggtttt gtaagagatg aaattcagtg tgtcatagct     2460
accatagctt ttggaatggg cattaataaa gctgacattc gccaagtcat tcattacggt     2520
gctcctaagg acatggaatc atattatcag gagattggta gagctggtcg tgatggactt     2580
caaagttctt gtcacgtcct ctgggctcct gcagacatta acttaaatag gcaccttctt     2640
actgagatac gtaatgagaa gtttcgatta tacaaattaa agatgatggc aaagatggaa     2700
aaatatcttc attctagcag atgtaggaga caaatcatct tgtctcattt tgaggacaaa     2760
caagtacaaa aagcctcctt gggaattatg ggaactgaaa aatgctgtga taattgcagg     2820
tccagattgg atcattgcta ttccatggat gactcagagg atacatcctg ggactttggt     2880
ccacaagcat ttaagctttt gtctgctgtg gacatcttag gcgaaaaatt tggaattggg     2940
cttccaattt tatttctccg aggatctaat tctcagcgtc ttgccgatca atatcgcagg     3000
cacagtttat ttggcactgg caaggatcaa acagagagtg ggtggaaggc ttttttcccgt     3060 cagctgatca ctgagggatt cttggtagaa gtttctcggt ataacaaatt tatgaagatt     3120 tgcgcccta cgaaaaaggg tagaaattgg cttcataaag ctaatacaga atctcagagc     3180
ctcatccttc aagctaatga agaattgtgt ccaaagaagt tgcttctgcc tagttcgaaa     3240
actgtatctt cgggcaccaa agagcattgt tataatcaag taccagttga attaagtaca     3300
gagaagaagt ctaacttgga gaagttatat tcttataaac catgtgataa gatttcttct     3360
gggagtaaca tttctaaaaa aagtatcatg gtacagtcac cagaaaaagc ttacagttcc     3420
```

```
tcacagcctg ttatttcggc acaagagcag gagactcaga ttgtgttata tggcaaattg      3480
gtagaagcta ggcagaaaca tgccaataaa atggatgttc ccccagctat tctggcaaca      3540
aacaagatac tggtggatat ggccaaaatg agaccaacta cggttgaaaa cgtaaaaagg      3600
attgatggtg tttctgaagg caaagctgcc atgttggccc ctctgttgga agtcatcaaa      3660
catttctgcc aaacaaatag tgttcagaca gacctctttt caagtacaaa acctcaagaa      3720
gaacagaaga cgagtctggt agcaaaaaat aaaatatgca cactttcaca gtctatggcc      3780
atcacatact ctttattcca agaaaagaag atgcctttga gagcatagc tgagagcagg      3840 attctgcctc tcatgacaat tggcatgcac ttatcccaag cggtgaaagc tggctgcccc      3900
cttgatttgg agcgagcagg cctgactcca gaggttcaga agattattgc tgatgttatc      3960
cgaaaccctc ccgtcaactc agatatgagt aaaattagcc taatcagaat gttagttcct      4020
gaaaacattg acacgtacct tatccacatg gcaattgaga tccttaaaca tggtcctgac      4080
agcggacttc aaccttcatg tgatgtcaac aaaaggagat gttttcccgg ttctgaagag      4140
atctgttcaa gttctaagag aagcaaggaa gaagtaggca tcaatactga gacttcatct      4200
gcagagagaa agagacgatt acctgtgtgg tttgccaaag gaagtgatac cagcaagaaa      4260
ttaatggaca aaacgaaaag gggaggtctt tttagttaa                              4299
```

<210> SEQ ID NO 30
<211> LENGTH: 4299
<212> TYPE: DNA
<213> ORGANISM: Artificial Sequence
<220> FEATURE:
<223> OTHER INFORMATION: K577MWRN

<400> SEQUENCE: 30

```
atgagtgaaa aaaaattgga aacaactgca cagcagcgga aatgtcctga atggatgaat        60
gtgcagaata aagatgtgc tgtagaagaa agaaaggcat gtgttcggaa gagtgttttt       120
gaagatgacc tccccttctt agaattcact ggatccattg tgtatagtta cgatgctagt       180
gattgctctt tcctgtcaga agatattagc atgagtctat cagatgggga tgtggtggga       240
tttgacatgg agtggccacc attatacaat agagggaaac ttggcaaagt tgcactaatt       300
cagttgtgtg tttctgagag caaatgttac ttgttccacg tttcttccat gtcagttttt       360
ccccagggat taaaaatgtt gcttgaaaat aaagcagtta aaaaggcagg tgtaggaatt       420
gaaggagatc agtggaaact tctacgtgac tttgatatca aattgaagaa ttttgtggag       480
ttgacagatg ttgccaataa aaagctgaaa tgcacagaga cctggagcct taacagtctg      540
gttaaacacc tcttaggtaa acagctcctg aaagacaagt ctatccgctg tagcaattgg      600
agtaaatttc ctctcactga ggaccagaaa ctgtatgcag ccactgatgc ttatgctggt       660
tttattattt accgaaattt agagattttg gatgatactg tgcaaaggtt tgctataaat       720
aaagaggaag aaatcctact tagcgacatg aacaaacagt tgacttcaat ctctgaggaa       780
gtgatggatc tggctaagca tcttcctcat gctttcagta aattggaaaa cccacggagg      840
gtttctatct tactaaagga tatttcagaa aatctatatt cactgaggag gatgataatt       900
gggtctacta acattgagac tgaactgagg cccagcaata atttaaactt attatccttt       960
gaagattcaa ctactggggg agtacaacag aaacaaatta gagaacatga gtttttaatt     1020
cacgttgaag atgaaacatg ggacccaaca cttgatcatt tagctaaaca tgatggagaa     1080
gatgtacttg gaaataaagt ggaacgaaaa gaagatggat ttgaagatgg agtagaagac     1140
aacaaattga aagagaatat ggaaagagct tgtttgatgt cgttagatat tacagaacat     1200
```

```
gaactccaaa ttttggaaca gcagtctcag gaagaatatc ttagtgatat tgcttataaa      1260
tctactgagc atttatctcc caatgataat gaaaacgata cgtcctatgt aattgagagt      1320
gatgaagatt tagaaatgga gatgcttaag catttatctc ccaatgataa tgaaaacgat      1380
acgtcctatg taattgagag tgatgaagat ttagaaatgg agatgcttaa gtctttagaa      1440
aacctcaata gtggcacggt agaaccaact cattctaaat gcttaaaaat ggaaagaaat      1500
ctgggtcttc ctactaaaga agaagaagaa gatgatgaaa atgaagctaa tgaaggggaa      1560
gaagatgatg ataaggactt tttgtggcca gcacccaatg aagagcaagt tacttgcctc      1620
aagatgtact ttggccattc cagttttaaa ccagttcagt ggaaagtgat tcattcagta      1680
ttagaagaaa gaagagataa tgttgctgtc atggcaactg gatatggaat gagtttgtgc      1740
ttccagtatc cacctgttta tgtaggcaag attggccttg ttatctctcc ccttatttct      1800
ctgatggaag accaagtgct acagcttaaa atgtccaaca tcccagcttg cttccttgga      1860
tcagcacagt cagaaaatgt tctaacagat attaaaattag gtaaataccg gattgtgtac      1920
gtgacccccg agtattgttc aggtaacatg ggcctgctcc agcaacttga ggctgatatt      1980
ggtatcacgc tcattgctgt ggatgaggct cactgtattt ctgagtgggg gcatgatttt      2040
agggattcat tcaggaagtt gggctcccta aagacagcac tgccaatggt tccaatcgtt      2100
gcacttactg ctactgcaag ttcttcaatc cgggaagaca ttgtacgttg cttaaatctg      2160
agaaatcctc agatcacctg tactggtttt gatcgaccaa acctgtattt agaagttagg      2220
cgaaaaacag ggaatatcct tcaggatctg cagccatttc ttgtcaaaac aagttcccac      2280
tgggaatttg aaggtccaac aatcatctac tgtccttcta gaaaaatgac acaacaagtt      2340
acaggtgaac ttaggaaact gaatctatcc tgtggaacat accatgcggg catgagtttt      2400
agcacaagga aagacattca tcataggttt gtaagagatg aaattcagtg tgtcatagct      2460
accatagctt ttggaatggg cattaataaa gctgacattc gccaagtcat tcattacggt      2520
gctcctaagg acatggaatc atattatcag gagattggta gagctggtcg tgatggactt      2580
caaagttctt gtcacgtcct ctgggctcct gcagacatta acttaaatag gcaccttctt      2640
actgagatac gtaatgagaa gtttcgatta tacaaattaa agatgatggc aaagatggaa      2700
aaatatcttc attctagcag atgtaggaga caaatcatct tgtctcattt tgaggacaaa      2760
caagtacaaa aagcctcctt gggaattatg ggaactgaaa atgctgtga taattgcagg       2820 tccagattgg atcattgcta ttccatggat gactcagagg atacatcctg ggactttggt      2880
ccacaagcat ttaagctttt gtctgctgtg gacatcttag gcgaaaaatt tggaattggg      2940
cttccaattt tatttctccg aggatctaat tctcagcgtc ttgccgatca atatcgcagg      3000
cacagtttat ttggcactgg caaggatcaa acagagagtt ggtggaaggc tttttcccgt      3060
cagctgatca ctgagggatt cttggtagaa gtttctcggt ataacaaatt tatgaagatt      3120
tgcgccctta cgaaaaaggg tagaaattgg cttcataaag ctaatacaga atctcagagc      3180
ctcatccttc aagctaatga agaattgtgt ccaaagaagt tgcttctgcc tagttcgaaa      3240
actgtatctt cgggcaccaa agagcattgt tataatcaag taccagttga attaagtaca      3300
gagaagaagt ctaacttgga gaagttatat tcttataaac catgtgataa gatttcttct      3360
gggagtaaca tttctaaaaa aagtatcatg gtacagtcac cagaaaaagc ttacagttcc      3420
tcacagcctg ttatttcggc acaagagcag gagactcaga ttgtgttata tggcaaattg      3480
gtagaagcta ggcagaaaca tgccaataaa atggatgttc ccccagctat tctggcaaca      3540
```

-continued

```
aacaagatac tggtggatat ggccaaaatg agaccaacta cggttgaaaa cgtaaaaagg    3600
attgatggtg tttctgaagg caaagctgcc atgttggccc ctctgttgga agtcatcaaa    3660
catttctgcc aaacaaatag tgttcagaca gacctctttt caagtacaaa acctcaagaa    3720
gaacagaaga cgagtctggt agcaaaaaat aaaatatgca cactttcaca gtctatggcc    3780
atcacatact ctttattcca agaaaagaag atgcctttga agagcatagc tgagagcagg    3840
attctgcctc tcatgacaat tggcatgcac ttatcccaag cggtgaaagc tggctgcccc    3900
cttgatttgg agcgagcagg cctgactcca gaggttcaga agattattgc tgatgttatc    3960
cgaaaccctc ccgtcaactc agatatgagt aaaattagcc taatcagaat gttagttcct    4020
gaaaacattg acacgtacct tatccacatg gcaattgaga tccttaaaca tggtcctgac    4080
agcggacttc aaccttcatg tgatgtcaac aaaaggagat gttttcccgg ttctgaagag    4140
atctgttcaa gttctaagag aagcaaggaa gaagtaggca tcaatactga gacttcatct    4200
gcagagagaa agagacgatt acctgtgtgg tttgccaaag gaagtgatac cagcaagaaa    4260
ttaatggaca aaacgaaaag gggaggtctt tttagttaa                           4299
```

METHOD FOR PREDICTING SENSITIVITY OF CANCER CELL TO HELICASE INHIBITOR

CROSS-REFERENCE TO RELATED APPLICATIONS

This application is the National Stage of International Application No. PCT/JP2020/043487, filed Nov. 20, 2020, which claims the benefit of Japanese Application No. JP2019-210304, filed Nov. 21, 2019, the contents of which are incorporated herein by reference in their entireties.

SEQUENCE LISTING

This application contains a Sequence Listing that has been submitted electronically as an ASCII text file named SequenceListing.txt. The ASCII text file, created on May 12, 2022, is 132 kilobytes in size. The material in the ASCII text file is hereby incorporated by reference in its entirety.

TECHNICAL FIELD

The present invention relates to a method for predicting sensitivity of a cancer cell to a helicase inhibitor. The present invention also relates to a method for predicting sensitivity of a cancer patient to treatment with a helicase inhibitor, a method for selecting a cancer patient for cancer treatment with a helicase inhibitor, a method for treating cancer, a method for screening compounds to be used for cancer treatment, and a cancer therapeutic drug.

BACKGROUND ART

In recent years, due to rapid advancement of genome sequence techniques, it has been possible to decode genome information including unique gene mutations in cancer cells. Under such circumstances, for development of anticancer drugs, inhibitors have been discovered which inhibit the functions specifically of a cancer cell having a gain-of-function gene mutation typified by EGFR gene mutation, BRAF gene mutation, an ALK fusion gene or the like (Non Patent Literatures 1 to 3). Treatment methods which target a cancer cell having such a gene mutation and are specific to the cancer cell are treatment methods with high cancer selectivity and a high effect.

For example, the survival of a cancer cell having MSI-H (microsatellite instability-high) has been reported to depend on WRN (Werner syndrome protein) (Non Patent Literatures 4 to 7), and it is considered that treatment for inhibiting WRN can specifically target such a cancer cell having MSI-H.

On the other hand, gene mutations found in human cancer cells include not only the gain-of-function gene mutations but also the opposite gene mutations which are loss-of-function gene mutations. For a loss-of-function gene mutation, it is difficult to discover a drug specific to the gene mutation, and a treatment strategy different from treatment targeting a cancer cell having a gain-of-function gene mutation is required.

The few successful cases of specifically targeting a cancer cell having a loss-of-function mutation include PARP inhibitors against a BRCA1/2-deficient tumor (Non Patent Literature 8). However, to date, any other treatment strategy specifically targeting a cancer cell having a loss-of-function mutation has not been developed yet.

CITATION LIST

Non Patent Literature

[Non Patent Literature 1] Makoto Maemondo et al., NEJM 2010 Jun. 24; 362 (25), p. 2380-2388
[Non Patent Literature 2] Paul B. Chapman et al., NEJM 2011 Jun. 30; 364 (26), p. 2507-2516
[Non Patent Literature 3] D. Ross Camidge et al., J Thorac Oncol. 2019 July; 14 (7), p. 1233-1243
[Non Patent Literature 4] Lorn Kategaya et al., iScience 13, Mar. 29, 2019, p. 488-497
[Non Patent Literature 5] Simone Lieb et al., eLife 2019, 8: e43333, DOI: https://doi.org/10.7554/eLife. 43333
[Non Patent Literature 6] Edmond M. Chan et al., Nature. 2019 April, 568 (7753), p. 551-556
[Non Patent Literature 7] Fiona M Behan et al., Nature. 2019 April, 568 (7753), p. 511-516
[Non Patent Literature 8] K. Moore et al., NEJM 2018 Dec. 27; 379 (26), p. 2495-2505

SUMMARY OF INVENTION

Technical Problem

The present invention has been made in view of the circumstances described above. An object of the present invention is to develop a treatment strategy capable of specifically targeting even a cancer cell having a loss-of-function mutation. More specifically, the object of the present invention is to develop a treatment strategy specifically targeting a cancer cell having at least one mutation detected selected from the first group consisting of TTK mutation and RAD 50 mutation and/or at least one mutation detected selected from the second group consisting of RAD 50 mutation, MRE 11 mutation, NBN mutation, DNA 2 mutation and RBBP 8 mutation.

Solution to Problem

The present inventors extensively conducted studies for solving the above-described problems. First, for all of about 70 cancer cell lines, expression of WRN was suppressed by siRNA, and mutations common to cell lines in which suppression of growth was confirmed. As a result, it was found that when expression of helicase such as WRN was suppressed or the function of the helicase was inhibited, growth of cancer cells was markedly suppressed for all of cancer cells having at least one mutation (preferably loss-of-function mutation) selected from the first group consisting of TTK mutation and RAD 50 mutation, and such suppression of growth did not occur for cells which did not have any of TTK mutation and RAD 50 mutation.

Further, the present inventors added target cancer cell lines, and analyzed all of about 200 cancer cell lines including about 70 cancer cell lines described above. As a result, it was found that when expression of helicase was suppressed or the function of the helicase was inhibited, growth of cancer cells was suppressed for all of cancer cells having at least one mutation (preferably loss-of-function mutation) selected from the second group consisting of RAD 50 mutation, MRE 11 mutation, NBN mutation, DNA 2 mutation and RBBP 8 mutation in addition to the mutations selected from the first group.

The mutations are some of mutations observed with high frequency in, for example, cancer cells having MSI-H. It is considered that MSI-H can be used as an indicator for selecting a cancer cell targeted by treatment for inhibiting WRN which is helicase as described above (e.g. Non Patent Literatures 4 to 7). However, the present inventors found that the suppression of growth did not occur in a cancer cell which had MSI-H but did not have any of the above-described mutations, particularly the mutations selected from the second group. Accordingly, the newly discovered mutations described above can be used as an indicator for selecting a cancer cell targeted by treatment for inhibiting helicase regardless of whether the mutations have MSI-H or not, and such mutations can be used as a more specific indicator for selecting the cancer cell than MSI-H.

Thus, the present inventors found that treatment for inhibiting helicase would be a promising approach for treatment targeting a cancer cell having at least one mutation selected from the first group consisting of TTK mutation and RAD 50 mutation and/or at least one mutation selected from the second group consisting of RAD 50 mutation, MRE 11 mutation, NBN mutation, DNA 2 mutation and RBBP 8 mutation. It was also revealed that in this treatment strategy, it was possible to select a cancer patient using the mutations as an indicator, followed by administering a helicase inhibitor, so that efficient treatment based on companion diagnosis was possible.

Further, the present inventors also found that screening of drugs useful for treatment of cancer having any of the above-described mutations was able to be performed using on the basis of whether helicase was inhibited or not, leading to completion of the present invention.

Accordingly, the present invention relates to a treatment method specifically targeting a cancer cell having at least one mutation selected from the first group consisting of TTK mutation and RAD 50 mutation and/or at least one mutation selected from the second group consisting of RAD 50 mutation, MRE 11 mutation, NBN mutation, DNA 2 mutation and RBBP 8 mutation, and companion diagnosis for the treatment method. More specifically, the present invention provides the following.

[1]

A method for predicting sensitivity of a cancer cell to a helicase inhibitor, the method comprising the step of:

predicting a cancer cell having at least one mutation detected selected from the first group consisting of TTK mutation and RAD 50 mutation, as having sensitivity to a helicase inhibitor.

[2]

A method for predicting sensitivity of a cancer cell to a helicase inhibitor, the method comprising the steps of:

(a) detecting the presence or absence of at least one mutation selected from the first group consisting of TTK mutation and RAD 50 mutation in a cancer cell; and (b) predicting a cancer cell having the mutation detected, as having sensitivity to a helicase inhibitor.

[3]

A method for predicting sensitivity of a cancer patient to treatment with a helicase inhibitor, the method comprising the step of:

predicting a cancer patient having at least one mutation selected from the first group consisting of TTK mutation and RAD 50 mutation detected in a cancer cell contained in a cancer patient-derived sample, as having sensitivity to treatment with a helicase inhibitor.

[4]

A method for predicting sensitivity of a cancer patient to treatment with a helicase inhibitor, the method comprising the steps of:

(a) detecting the presence or absence of at least one mutation selected from the first group consisting of TTK mutation and RAD 50 mutation in a cancer cell contained in a cancer patient-derived sample; and (b) predicting a cancer patient having the mutation detected in the cancer cell, as having sensitivity to treatment with a helicase inhibitor.

[5]

A method for selecting a cancer patient for cancer treatment with a helicase inhibitor, the method comprising the step of:

selecting a cancer patient having at least one mutation selected from the first group consisting of TTK mutation and RAD 50 mutation detected in a cancer cell contained in a cancer patient-derived sample, for cancer treatment with a helicase inhibitor.

[6]

A method for selecting a cancer patient for cancer treatment with a helicase inhibitor, the method comprising the steps of:

(a) detecting the presence or absence of at least one mutation selected from the first group consisting of TTK mutation and RAD 50 mutation in a cancer cell contained in a cancer patient-derived sample; and (b) selecting a cancer patient having the mutation detected in the cancer cell, for cancer treatment with a helicase inhibitor.

[7]

A method for treating cancer, the method comprising the step of:

administering a helicase inhibitor to a cancer patient having at least one mutation selected from the first group consisting of TTK mutation and RAD 50 mutation in a cancer cell contained in a cancer patient-derived sample.

[8]

A method for treating cancer, the method comprising the step of:

(a) detecting the presence or absence of at least one mutation selected from the first group consisting of TTK mutation and RAD 50 mutation in a cancer cell contained in a cancer patient-derived sample; and (b) administering a helicase inhibitor to a cancer patient having the mutation detected in the cancer cell.

[9]

The method according to any one of [1] to [8], wherein the helicase inhibitor is a WRN inhibitor.

[10]

The method according to any one of [1] to [9], wherein the cancer cell is a cancer cell having MSH 3 mutation further detected.

[11]

A method for screening compounds to be used for treatment of cancer containing a cancer cell having at least one mutation detected selected from the first group consisting of TTK mutation and RAD 50 mutation, the method comprising the step of:

selecting a compound on the basis of whether helicase is inhibited or not.

[12]

A cancer therapeutic drug comprising a compound, which inhibits helicase, as an active ingredient, the cancer therapeutic drug being a therapeutic drug for cancer containing a cancer cell having at least one mutation detected selected from the group consisting of TTK mutation and RAD 50 mutation.

[13]

The method according to [11], wherein the helicase is WRN.

[14]

The cancer therapeutic drug according to [12], wherein the helicase is WRN.

[15]

A method for predicting sensitivity of a cancer cell to a helicase inhibitor, the method comprising the step of:

predicting a cancer cell having at least one mutation detected selected from the second group consisting of RAD 50 mutation, MRE 11 mutation, NBN mutation, DNA 2 mutation and RBBP 8 mutation, as having sensitivity to a helicase inhibitor.

[16]

A method for predicting sensitivity of a cancer cell to a helicase inhibitor, the method comprising the steps of:

(a) detecting the presence or absence of at least one mutation selected from the second group consisting of RAD 50 mutation, MRE 11 mutation, NBN mutation, DNA 2 mutation and RBBP 8 mutation in a cancer cell; and (b) predicting a cancer cell having the mutation detected, as having sensitivity to a helicase inhibitor.

[17]

A method for predicting sensitivity of a cancer patient to treatment with a helicase inhibitor, the method comprising the step of:

predicting a cancer patient having at least one mutation selected from the second group consisting of RAD 50 mutation, MRE 11 mutation, NBN mutation, DNA 2 mutation and RBBP 8 mutation detected in a cancer cell contained in a cancer patient-derived sample, as having sensitivity to treatment with a helicase inhibitor.

[18]

A method for predicting sensitivity of a cancer patient to treatment with a helicase inhibitor, the method comprising the steps of:

(a) detecting the presence or absence of at least one mutation selected from the second group consisting of RAD 50 mutation, MRE 11 mutation, NBN mutation, DNA 2 mutation and RBBP 8 mutation in a cancer cell contained in a cancer patient-derived sample; and (b) predicting a cancer patient having the mutation detected in the cancer cell, as having sensitivity to treatment with a helicase inhibitor.

[19]

A method for selecting a cancer patient for cancer treatment with a helicase inhibitor, the method comprising the step of:

selecting a cancer patient having at least one mutation selected from the second group consisting of RAD 50 mutation, MRE 11 mutation, NBN mutation, DNA 2 mutation and RBBP 8 mutation detected in a cancer cell contained in a cancer patient-derived sample, for cancer treatment with a helicase inhibitor.

[20]

A method for selecting a cancer patient for cancer treatment with a helicase inhibitor, the method comprising the steps of:

(a) detecting the presence or absence of at least one mutation selected from the second group consisting of RAD 50 mutation, MRE 11 mutation, NBN mutation, DNA 2 mutation and RBBP 8 mutation in a cancer cell contained in a cancer patient-derived sample; and (b) selecting a cancer patient having the mutation detected in the cancer cell, for cancer treatment with a helicase inhibitor.

[21]

A method for treating cancer, the method comprising the step of:

administering a helicase inhibitor to a cancer patient having at least one mutation selected from the second group consisting of RAD 50 mutation, MRE 11 mutation, NBN mutation, DNA 2 mutation and RBBP 8 mutation detected in a cancer cell contained in a cancer patient-derived sample.

[22]

A method for treating cancer, the method comprising the steps of:

(a) detecting the presence or absence of at least one mutation selected from the second group consisting of RAD 50 mutation, MRE 11 mutation, NBN mutation, DNA 2 mutation and RBBP 8 mutation in a cancer cell contained in a cancer patient-derived sample; and (b) administering a helicase inhibitor to a cancer patient having the mutation detected in the cancer cell.

[23]

The method according to any one of [15] to [22], wherein the helicase inhibitor is a WRN inhibitor.

[24]

The method according to any one of [15] to [23], wherein the cancer cell is a cancer cell having at least one mutation detected selected from the third group consisting of EXO 1 mutation, RPA 1 mutation, RPA 2 mutation and RPA 3 mutation.

[25]

A method for screening compounds to be used for treatment of cancer containing a cancer cell in which at least one mutation selected from the second group consisting of RAD 50 mutation, MRE 11 mutation, NBN mutation, DNA 2 mutation and RBBP 8 mutation, the method comprising the step of:

selecting a compound on the basis of whether helicase is inhibited or not.

[26]

A cancer therapeutic drug comprising a compound, which inhibits helicase, as an active ingredient, the cancer therapeutic drug being a therapeutic drug for cancer containing a cancer cell having at least one mutation detected selected from the second group consisting of RAD 50 mutation, MRE 11 mutation, NBN mutation, DNA 2 mutation and RBBP 8 mutation.

[27]

The method according to [25], wherein the helicase is WRN.

[28]

The cancer therapeutic drug according to [26], wherein the helicase is WRN.

Advantageous Effects of Invention

According to the present invention, it is possible to efficiently predict sensitivity to cancer treatment with a helicase inhibitor using at least one mutation selected from the first group consisting of TTK mutation and RAD 50 mutation and/or at least one mutation selected from the second group consisting of RAD 50 mutation, MRE 11 mutation, NBN mutation, DNA 2 mutation and RBBP 8 mutation as an indicator. In addition, according to the present invention, it is possible to detect the presence or absence of the mutation in a cancer patient-derived sample and select a patient having the mutation detected, followed by subjecting the patient to treatment of cancer with a helicase inhibitor. This enables significant improvement of cancer treatment outcomes. In addition, it is possible to efficiently perform companion diagnosis by detection of the presence or absence of the mutation by using an oligonucleotide probe or primer against at least one gene selected from the first group consisting of TTK and RAD 50 and/or at least one gene selected from the second group consisting of RAD 50, MRE 11, NBN (gene encoding NBS 1), DNA 2 and RBBP 8 (gene encoding CtIP), and an antibody against at least one protein selected from the first group consisting of TTK protein and RAD 50 protein and/or at least one protein selected from the second group consisting of RAD 50 protein, MRE 11 protein, NBS 1 protein, DNA 2 protein and CtIP protein.

DESCRIPTION OF EMBODIMENTS

Figure 1:
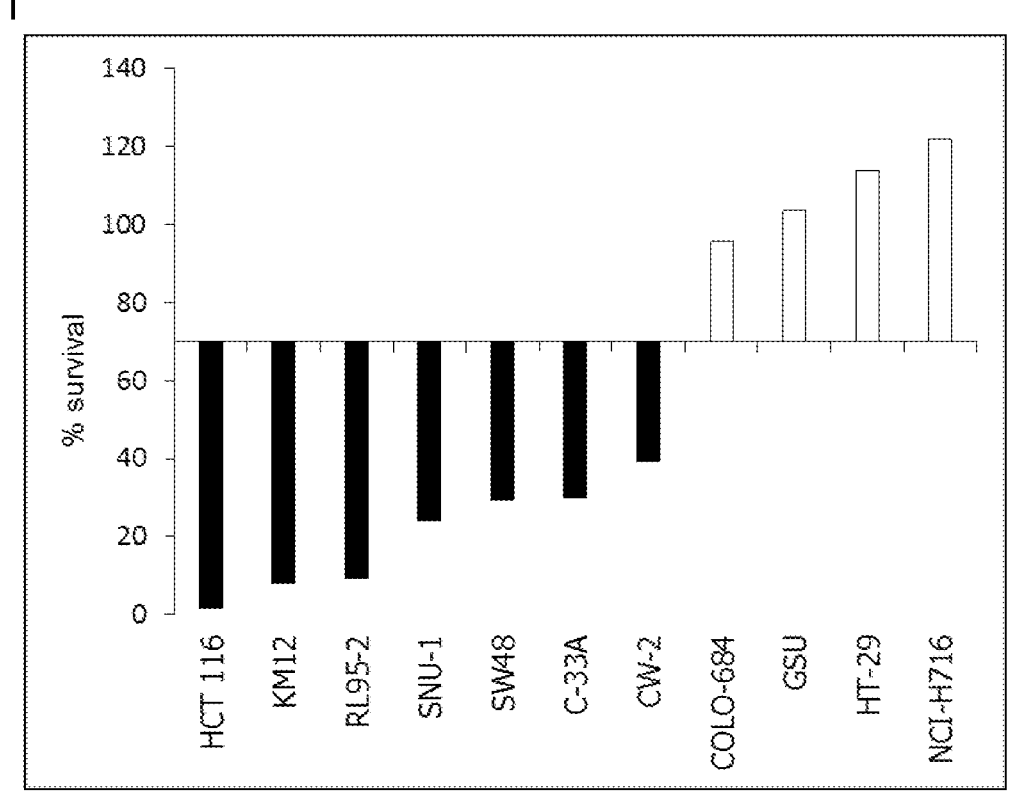
FIG. 1 is a graph showing cell survival rate under suppression of expression of WRN in a cancer cell line in Test Example 1.

Hereinafter, the present invention will be described in detail along preferred embodiments thereof <Method for Predicting Sensitivity of Cancer Cell to Helicase Inhibitor, Method for Predicting Sensitivity of Patient to Treatment with Helicase Inhibitor, and Method for Selecting a Cancer Patient for Cancer Treatment with Helicase Inhibitor>

In the present invention, it has been found that when helicase is inhibited in a cancer cell having at least one mutation selected from the first group consisting of TTK mutation and RAD 50 mutation (herein, sometimes referred to as "TTK mutation and/or RAD 50 mutation" or "first group mutation"), preferably a loss-of-function mutation, growth of the cancer cell can be suppressed. In addition, it has been found that when helicase is inhibited in a cancer cell having at least one mutation selected from the second group consisting of RAD 50 mutation, MRE 11 mutation, NBN mutation, DNA 2 mutation and RBBP 8 mutation (herein, sometimes referred to as "second group mutation"), preferably a loss-of-function mutation, growth of the cancer cell can be suppressed.

According to these findings, sensitivity of a cancer cell to a helicase inhibitor can be predicted using the first group mutation and/or the second group mutation as an indicator. Accordingly, the present invention provides:

a method for predicting sensitivity of a cancer cell to a helicase inhibitor, the method comprising the steps of:
(a) detecting the presence or absence of at least one mutation selected from the first group consisting of TTK mutation and RAD 50 mutation in a cancer cell; and
(b) predicting a cancer cell having the mutation detected, as having sensitivity to a helicase inhibitor; and
a method for predicting sensitivity of a cancer cell to a helicase inhibitor, the method comprising the steps of:

(a) detecting the presence or absence of at least one mutation selected from the second group consisting of RAD 50 mutation, MRE 11 mutation, NBN mutation, DNA 2 mutation and RBBP 8 mutation; and
(b) predicting a cancer cell having the mutation detected, as having sensitivity to a helicase inhibitor.
(Hereinafter, these methods are sometimes referred to collectively as a "cancer cell sensitivity prediction method".)

According to the above-described findings, sensitivity to cancer treatment with a helicase inhibitor can be predicted using the first group mutation and/or the second group mutation as an indicator. Accordingly, the present invention provides:

a method for predicting sensitivity of a cancer patient to treatment with a helicase inhibitor, the method comprising the steps of:
(a) detecting the presence or absence of at least one mutation selected from the first group consisting of TTK mutation and RAD 50 mutation in a cancer cell contained in a cancer patient-derived cell; and
(b) predicting a cancer patient having the mutation detected in the cancer cell, as having sensitivity to treatment with a helicase inhibitor; and
a method for predicting sensitivity of a cancer patient to treatment with a helicase inhibitor, the method comprising the steps of:
(a) detecting the presence or absence of at least one mutation selected from the second group consisting of RAD 50 mutation, MRE 11 mutation, NBN mutation, DNA 2 mutation and RBBP 8 mutation in a cancer cell contained in a cancer patient-derived sample; and
(b) predicting a cancer patient having the mutation detected in the cancer cell, as having sensitivity to treatment with a helicase inhibitor.
(Hereinafter, these methods are sometimes referred to collectively as a "cancer patient sensitivity prediction method".)

Further, a patient having the first group mutation and/or the second group mutation detected in this way can be suitable for cancer treatment with a helicase inhibitor, and therefore using the first group mutation and/or the second group mutation as an indicator, a patient who benefits from cancer treatment with a helicase inhibitor and a patient who does not benefit from the cancer treatment can be discriminated from each other to perform efficient treatment. Accordingly, the present invention provides:

a method for selecting a cancer patient for cancer treatment with a helicase inhibitor, the method comprising the step of:
(a) detecting the presence or absence of at least one mutation selected from the first group consisting of TTK mutation and RAD 50 mutation in a cancer cell contained in a cancer patient-derived sample; and
(b) selecting a cancer patient having the mutation detected in the cancer cell, for cancer treatment with a helicase inhibitor; and
a method for selecting a cancer patient for cancer treatment with a helicase inhibitor, the method comprising the steps of:
(a) detecting the presence or absence of at least one mutation selected from the second group consisting of RAD 50 mutation, MRE 11 mutation, NBN mutation, DNA 2 mutation and RBBP 8 mutation in a cancer cell contained in a cancer patient-derived sample; and (b) selecting a cancer patient having the mutation detected in the cancer cell, for cancer treatment with a helicase inhibitor.

(Hereinafter, these methods are sometimes referred to collectively as a "cancer patient selection method".)

(Samples)

In the present invention, malignant neoplasms such as carcinomas (epithelial tumors), leukemia, malignant lymphomas, myelomas, sarcomas and carcinosarcomas, etc. are referred to collectively as "cancer", and a cell forming the cancer is referred to as a "cancer cell". Examples of the cancer containing a cancer cell in which the presence or absence of the first group mutation and/or the second group mutation can be detected include, but are not limited to, bowel cancer, stomach cancer, uterine cervix cancer, uterine body cancer, prostate cancer, esophagus cancer, breast cancer, lung cancer, bladder cancer, head and neck cancer, kidney cancer, ovary cancer, lymphoma, adenoid cystic cancer and pancreas cancer. In the present invention, the cancer cell may be a cancer cell further having MSH 3 mutation described later, or a cancer cell further having at least one mutation selected from the third group consisting of EXO 1 mutation, RPA 1 mutation, RPA 2 mutation and RPA 3 mutation. A cancer cell further having MSH 3 mutation is preferable when the first group mutation is detected, and a cancer cell further having the third group mutation is preferable when the second group mutation is detected.

In the present invention, the "cancer patient" may be not only a human affected with the cancer, but also a human possibly affected with the cancer. In the method of the present invention, the cancer patient to be subjected to detection of the first group mutation and/or the second group mutation is not particularly limited, and may include all cancer patients.

The "cancer patient-derived sample" for use in the present invention is not particularly limited as long as it is a biological sample allowing the presence or absence of the first group mutation and/or the second group mutation to be detected, and a specimen material such as a cancer biopsy specimen material, blood, urine, body cavity fluid or tumor cell-derived circulating DNA (ctDNA). The cancer patient-derived sample may be a protein extract or a nucleic acid extract obtained from the specimen material (e.g. a mRNA extract, or a cDNA preparation or a cRNA preparation prepared from a mRNA extract). In the present description, the "biological sample" includes cancer patient-derived samples and cancer cell culture-derived samples.

(Helicase Inhibitor)

The "helicase inhibitor" in the present invention means a composition containing at least one compound which inhibits helicase. The helicase inhibitor may be one including only the compounds or a combination thereof, or one further containing additive ingredients described below. The "compound which inhibits helicase" in the present invention includes compounds which inhibit at least one of the activity of helicase and the expression of helicase.

The "helicase" targeted by a helicase inhibitor in the present invention is not particularly limited, and examples thereof include RecQ helicase (RecQ L1, BLM, WRN, RecQ L4/RTS and RecQ L5). RecQ helicase is preferable, and WRN (Werner syndrome protein) is more preferable. A typical nucleotide sequence of genome DNA encoding human-derived natural WRN is set forth as SEQ ID NO: 1, and a typical amino acid sequence of human-derived natural WRN is set forth as SEQ ID NO: 2. Even among WRN genes (genes encoding WRN) which do not have mutations associated with substitution, deletion, insertion, addition and the like of amino acid sequences, there may be an interindividual difference in sequence due to polymorphism or the like.

Inhibition of the activity of the helicase by the compound can be confirmed by, for example, adding the test compound to a system which includes double-stranded DNA labeled at each strand with quencher molecules and fluorescent molecules, and the helicase and which generates fluorescence due to separation of the fluorescent molecules from the quencher molecules when dissociated into single-stranded DNA; and detecting suppression of the generation of the fluorescence (Sommers J A et al., A high-throughput screen to identify novel small molecule inhibitors of the Werner Syndrome Helicase-Nuclease (WRN), PLoS One. 2019 Jan. 9; 14(1): e0210525).

Inhibition of the expression of the helicase by the compound can be confirmed by, for example, detecting a decrease in expression of helicase (preferably WRN) in a cell treated with the test compound. Examples of the method for detecting a decrease in expression of helicase include a method in which normally, the expression level of helicase is detected at a transcriptional level or a translational level, and compared to a control (e.g. expression level of a cell which is not treated with the test compound) to confirm that the expression level is lower than the control.

In the method for detecting the expression level of the helicase at a transcriptional level, first, RNA or cDNA is prepared from a cell treated with the test compound. The method for extracting RNA from the cell is not particularly limited, and a known method can be appropriately selected and used. Examples thereof include extraction methods using phenol and a chaotropic salt (more specifically, extraction methods using a commercially available kit such as TRIzol (manufactured by Invitrogen Corporation) or ISO-GEN (manufactured by Wako Pure Chemical Industries, Ltd.)), and methods using another commercially available kit (e.g. RNAPrep Total RNA Extraction Kit (manufactured by Beckman Coulter Inc.), RNeasy Mini (manufactured by QIAGEN N.V.) or RNA Extraction Kit (Pharmacia Biotech, Inc.)). Further, the reverse transcriptase used for preparation of cDNA from extracted RNA is not particularly limited, and examples thereof include reverse transcriptases derived from retroviruses such as RAV (Rous associated virus) and AMV (Avian myeloblastosis virus), and reverse transcriptases derived from mouse retroviruses such as MMLV (Moloney murine leukemia virus).

Subsequently, an oligonucleotide primer or an oligonucleotide probe is used for an amplification reaction or a hybridization reaction, and an amplified product or a hybrid product thereof is detected. As such a method, for example, a RT-PCR method, a Northern blot method, a dot blot method, a DNA assay method, an in situ hybridization method, a RNase protection assay method, mRNA-seq or the like can be used. Those skilled in the art can design an oligonucleotide primer or an oligonucleotide probe suitable for each method in a conventional manner on the basis of a nucleotide sequence of cDNA encoding the helicase.

In the method for detecting the expression level of the helicase at a translational level, first, a protein sample is prepared from a cell treated with the test compound. Subsequently, using an antibody specific to the helicase, an antigen-antibody reaction is carried out, and the helicase is detected. In such a method for detecting protein using an antibody, for example, an antibody specific to helicase is added to the protein sample to carry out an antigen-antibody reaction, and binding of the antibody to the helicase is detected. When the sample is labeled with antibody specific to helicase, helicase can be directly detected, and when the sample is not labeled, a labeled molecule which recognizes the antibody (e.g. secondary antibody or protein A) can be further applied to indirectly detect helicase using the label of the molecule. As such a method, for example, an immunohistochemistry (immunostaining) method, a Western blotting method, an ELISA method, flow cytometry, imaging cytometry, radioimmunoassay, an immunoprecipitation method, or an analysis method using an antibody array can be used.

The type, the origin and the like of an antibody used are not particularly limited, and a monoclonal antibody is preferable. An oligoclonal antibody (mixture of several antibodies or dozens of antibodies) or a polyclonal antibody can also be used as long as it is possible to detect helicase with sufficient specificity. Functional fractions of antibodies such as Fab, Fab', F(ab')2, Fv, scFv, sc(Fv)$_2$, dsFv and diabodies, and multimers (e.g. dimers, trimers, tetramers and polymers) thereof can also be used. The helicase antibody may be a marketed product.

The helicase can also be detected by mass spectrometry (MS). In particular, analysis by a mass spectrometer coupled with liquid chromatography (LC/MS) is sensitive, and therefore advantageous. Detection by mass spectrometry can be performed by, for example, labeling the protein sample with the protein, fractionating the labeled protein, subjecting the fractionated protein to mass analysis, and identifying helicase from the mass analysis value. As the label, an isotopic labeling reagent known in the art can be used, and an appropriate labeling reagent can be obtained as a marketed product. The fractionation can be performed by a method known in the art, and for example, a commercially available strong cation column or the like can be used.

The "compound which inhibits helicase" in the present invention is not particularly limited, may be a known compound, or a compound identified by screening described later, and is preferably at least one selected from the group consisting of a compound, a polypeptide and a polynucleotide.

Examples of the compound include low-molecular compounds (molecular weight: less than 900) and middle-molecular compounds (molecular weight: 900 to 2000). The polypeptide includes full-length polypeptides encoded by a gene, fractions thereof, synthesized polypeptides, cyclic polypeptides, glycopeptides, and non-natural polypeptides. The polypeptide includes antibodies and antigen peptides, and the antibody may be a polyclonal antibody or a monoclonal antibody. The antibody includes complete antibodies, antibody fractions (e.g. Fab, Fab', F(ab')2, Fv, scFv, sc(Fv)$_2$, dsFv and diabodies), multimers thereof, and low-molecular antibodies in which variable regions of antibodies are bound. Examples of the polynucleotide include DNA, RNA and SiRNA, including full-length polynucleotides, fractions thereof and synthesized polynucleotides.

The "helicase inhibitor" in the present invention can be used as various dosage forms such as tablets, pills, powders, granules, capsules and solutions depending on the properties thereof, may further contain pharmacologically acceptable additive ingredients such as sterilized water, physiological saline, vegetable oil, solvents, bases, emulsifiers, suspension agents, surfactants, stabilizers, flavoring agents, fragrances, excipients, vehicles, preservatives, binders, diluents, tonicity agents, soothing agents, extenders, disintegrants, buffering agents, coating agents, lubricants, colorants, sweeteners, viscous agents, taste and odor improvers and solubilizers depending on the dosage form, and can be produced by a known pharmaceutical method using these components.

In the helicase inhibitor according to the present invention, the content of the compound which inhibits the helicase (the total content of the compounds if there are the two or more compounds) can be appropriately adjusted according to the dosage form or the use purpose of the helicase inhibitor.

(First Group Mutation and Second Group Mutation)

[TTK]

The "TTK" in the present invention is a gene encoding serine-threonine kinase involved in centrosome duplication and mitotic checkpoint response (herein, sometimes referred to as "TTK protein"). A typical nucleotide sequence of human-derived natural TTK genome DNA is set forth as SEQ ID NO: 3, and a typical amino acid sequence of human-derived natural TTK protein is set forth as SEQ ID NO: 4. Even among TTKs which do not have mutations associated with substitution, deletion, insertion, addition and the like of amino acid sequences, there may be an interindividual difference in sequence due to polymorphism or the like.

Examples of the "TTK mutation" in the present invention include substitution, deletion, insertion and addition of amino acids in the amino acid sequence of TTK protein. The TTK mutation is not particularly limited as long as it is a mutation in which the intrinsic activity of TTK protein changes, and the TTK mutation is preferably a mutation which causes a decrease in activity of TTK protein (including complete loss of activity (deactivation) of TTK protein), i.e. a loss-of-function mutation. A decrease in activity of TTK protein can be caused by, for example, a change in gene structure such as a missense mutation in TTK, a nonsense mutation over the entire region, or total or partial deletion of TTK, or a change in gene expression level, but is not limited thereto.

Whether the intrinsic gene structure or gene expression level of TTK changes or not can be confirmed and determined by, for example, the following method: acquisition of the nucleotide sequence of TTK by a sequence of genome DNA; detection of fluorescence by a oligonucleotide probe binding specifically to the nucleotide sequence of TTK; detection by a PCR method using an oligonucleotide primer binding specifically to the nucleotide of TTK; or the like, and on the basis of whether the gene structure or gene expression level changes or not in comparison with a control (e.g. a healthy subject or a non-cancer tissue in the same patient) (preferably whether a loss-of-function mutation occurs or not, or the expression level of mRNA decreases or not).

Whether the intrinsic activity (functional activity) of TTK protein changes or not can be confirmed and determined by, for example, the following method: an immunostaining method or a Western blotting method using an antibody binding specifically to TTK protein; a method in which whether intracellular TTK protein purified by an immunoprecipitation method or the like phosphorylates a substrate peptide is determined by a Western blotting method etc.; or the like, and on the basis of whether the activity changes or not in comparison with a control (e.g. a healthy subject or a non-cancer tissue in the same patient) (preferably whether the activity decreases or not, i.e. whether the expression level of protein detected by the immunostaining method or the Western blotting method decreases or not as compared to the control, whether the molecular weight of protein detected by the Western blotting method changes or not as compared to the control, or whether the phosphorylation activity decreases or not as compared to the control).

Specific examples of the TTK mutation which causes such a change in activity of TTK protein include p.L84* (COSMIC Legacy Mutation ID: COSM1643150), p.S162Vfs*9 (COSMIC Legacy Mutation ID: COSM3176137), p.K192Sfs*18 (COSMIC Legacy Mutation ID: COSM1446079), p.Q193Afs*33 (COSMIC Legacy Mutation ID: COSM3176143), p.R232Sfs*26 (COSMIC Legacy Mutation ID: COSM5895418), p.Q480Hfs*30 (COSMIC Legacy Mutation ID: COSM150902), p.N606Kfs*3 (COSMIC Legacy Mutation ID: COSM7741406), p.S618Ifs*3 (COSMIC Legacy Mutation ID: COSM6811382), p.E851Kfs*42 (COSMIC Legacy Mutation ID: COSM3176214), p.R854Gfs*10 (COSMIC Legacy Mutation ID: COSM1446097), p.R854Gfs*10 (COSMIC Legacy Mutation ID: COSM3176218), p.R854Gfs*39 (COSMIC Legacy Mutation ID: COSM252896), p.R854Kfs*11 (COSMIC Legacy Mutation ID: COSM253159), and p.K857Nfs*36 (COSMIC Legacy Mutation ID: COSM273397).

[RAD 50]

The "RAD 50" in the present invention is a gene encoding a protein involved in a DNA repair mechanism (in particular, a double-stranded DNA homologous end repair mechanism) (herein, sometimes referred to as "RAD 50 protein") by forming a complex together with the following MRE 11 protein and NBS 1 protein (MRN complex). A typical nucleotide sequence of human-derived natural RAD 50 genome DNA is set forth as SEQ ID NO: 5, and a typical amino acid sequence of human-derived natural RAD 50 protein is set forth as SEQ ID NO: 6. Even among RAD 50s which do not have mutations associated with substitution, deletion, insertion, addition and the like of amino acid sequences, there may be an interindividual difference in sequence due to polymorphism or the like.

Examples of the "RAD 50 mutation" in the present invention include substitution, deletion, insertion and addition of amino acids in the amino acid sequence of RAD 50 protein. The RAD 50 mutation is not particularly limited as long as it is a mutation in which the intrinsic activity of RAD 50 protein changes, and the RAD 50 mutation is preferably a mutation which causes a decrease in activity of RAD 50 protein (including complete loss of activity (deactivation) of RAD 50 protein), i.e. a loss-of-function mutation. A decrease in activity of RAD 50 protein can be caused by, for example, a change in gene structure such as a missense mutation in RAD 50, a nonsense mutation over the entire region, or total or partial deletion of RAD 50, or a change in gene expression level, but is not limited thereto.

Whether the intrinsic gene structure or gene expression level of RAD 50 changes or not can be confirmed and determined by, for example, the following method: acquisition of the nucleotide sequence of RAD 50 by a sequence of genome DNA; detection of fluorescence by a oligonucleotide probe binding specifically to the nucleotide sequence of RAD 50; detection by a PCR method using an oligonucleotide primer binding specifically to the nucleotide of RAD 50; or the like, and on the basis of whether the gene structure or gene expression level changes or not in comparison with a control (e.g. a healthy subject or a non-cancer tissue in the same patient) (preferably whether a loss-of-function mutation occurs or not, or the expression level of mRNA decreases or not).

Whether the intrinsic activity (functional activity) of RAD 50 protein changes or not can be confirmed and determined by, for example, the following method: an immunostaining method or a Western blotting method using an antibody binding specifically to RAD 50 protein; a method in which whether intracellular RAD 50 protein purified by an immunoprecipitation method or the like is bound to MRE 11 protein or NBS 1 protein that is constituent protein of the MRN complex is determined by a Western blotting method etc.; a method in which whether intracellular RAD 50 protein purified by an immunoprecipitation method or the like has ATPase activity is determined by an ATPase activity measurement method; or the like, and on the basis of whether the activity changes or not in comparison with a control (e.g. a healthy subject or a non-cancer tissue in the same patient) (preferably whether the activity decreases or not, i.e. whether the expression level of RAD 50 protein detected by the immunostaining method or the Western blotting method decreases or not as compared to the control, whether the molecular weight of protein detected by the Western blotting method changes or not as compared to the control, whether the amount of MRE 11 protein or NBS 1 protein that is constituent protein of the MRN complex bound to RAD 50 protein detected by the Western blotting method decreases or not as compared to the control, or whether the ATPase activity decreases or not as compared to the control).

Specific examples of the RAD 50 mutation which causes such a change in activity of RAD 50 protein include p.A149Gfs*10 (COSMIC Legacy Mutation ID: COSM7087398), p.C157Lfs*7 (COSMIC Legacy Mutation ID: COSM9001198), p.S181Ffs*7 (COSMIC Legacy Mutation ID: COSM9008445), p.K279Efs*7 (COSMIC Legacy Mutation ID: COSM5016099), p.T410Lfs*5 (COSMIC Legacy Mutation ID: COSM6941414), p.K425Tfs*4 (COSMIC Legacy Mutation ID: COSM9494174), p.L439Kfs*4 (COSMIC Legacy Mutation ID: COSM1158978), p.N459Mfs*2 (COSMIC Legacy Mutation ID: COSM8515312), p.L541Afs*7 (COSMIC Legacy Mutation ID: COSM6971853), p.R617Efs*26 (COSMIC Legacy Mutation ID: COSM4747889), p.D675Tfs*45 (COSMIC Legacy Mutation ID: COSM5016101), p.Q689Rfs*31 (COSMIC Legacy Mutation ID: COSM6761894), p.K722Gfs*5 (COSMIC Legacy Mutation ID: COSM6048265), p.K722Rfs*14 (COSMIC Legacy Mutation ID: COSM1433045), p.E723Gfs*5 (COSMIC Legacy Mutation ID: COSM4611459), p.K722Nfs*6, p.L929Sfs*10 (COSMIC Legacy Mutation ID: COSM1740881), p.N934Ifs*6 (COSMIC Legacy Mutation ID: COSM1433049), p.N934Kfs*10 (COSMIC Legacy Mutation ID: COSM1287518), p.E995Rfs*2 (COSMIC Legacy Mutation ID: COSM6962279), p.L1042Ffs*15 (COSMIC Legacy Mutation ID: COSM5617248), and p.Y1182Lfs*2 (COSMIC Legacy Mutation ID: COSM1633926).

[MRE 11 and NBN]

The "MRE 11 (also known as "MRE 11A")" in the present invention is a gene encoding a protein which forms a complex (MRN complex) together with the RAD 50 protein (herein, sometimes referred to as "MRE 11 protein"). The MRE 11 protein is a nuclease capable of degrading DNA as an exonuclease at an end and as an endonuclease at an internal site of DNA. The "NBN" in the present invention is a gene encoding NBS 1 being a protein which forms a complex (MRN complex) together with the RAD 50 protein (herein, sometimes referred to as "NBS 1 protein"). These proteins are linked to each other and involved in a DNA repair mechanism (in particular, a double-stranded DNA homologous end repair mechanism) (e.g. Lei Bian et al., Molecular Cancer, (2019) 18:169, DOI: https://doi.org/10.1186/s12943-019-1100-5; and Kwi H Koh et al., Laboratory Investigation, (2005) 85, p. 1130-1138). If the function of one of these proteins is deleted, the function of the MRN complex itself decreases, so that the DNA repair mechanism does not normally function. Therefore, particularly for RAD 50, MRE 11 and NBN encoding a protein forming such a MRN complex, among the second group mutations, it is preferable to detect at least one of these mutations, and it is more preferable to detect at least one of RAD 50 mutation and NBN mutation.

A typical nucleotide sequence of human-derived natural MRE 11 genome DNA is set forth as SEQ ID NO: 9, and a typical amino acid sequence of human-derived natural MRE 11 protein is set forth as SEQ ID NO: 10. A typical nucleotide sequence of human-derived natural NBN genome DNA (genome DNA encoding NBS 1) is set forth as SEQ ID NO: 11, and a typical amino acid sequence of human-derived natural NBS 1 protein is set forth as SEQ ID NO: 12. Even among MRE 11s and NBNs which do not have mutations associated with substitution, deletion, insertion, addition and the like of amino acid sequences, there may be an interindividual difference in sequence due to polymorphism or the like.

Examples of the "MRE 11 mutation" and the "NBN mutation" in the present invention include substitution, deletion, insertion and addition of amino acids in the amino acid sequences of MRE 11 protein and NBS 1 protein, respectively. The MRE 11 mutation and the NBN mutation are not particularly limited as long as they are mutations in which the intrinsic activities of MRE 11 protein and NBS 1 protein change, respectively, and the MRE 11 mutation and the NBN mutation are preferably mutations which cause, respectively, a decrease in activity of MRE 11 protein (including complete loss of activity (deactivation) of MRE 11 protein) and a decrease in activity of NBS 1 protein (including complete loss of activity (deactivation) of NBS 1 protein), i.e. loss-of-function mutations. A decrease in activity of MRE 11 protein can be caused by, for example, a change in gene structure such as a missense mutation in MRE 11, a nonsense mutation over the entire region, or total or partial deletion of MRE 11, or a change in gene expression level, but is not limited thereto. A decrease in activity of NBS 1 protein can be caused by, for example, a change in gene structure such as a missense mutation in NBN, a nonsense mutation over the entire region, or total or partial deletion of NBN, or a change in gene expression level, but is not limited thereto.

Whether the intrinsic gene structure or gene expression level of MRE 11 and the intrinsic gene structure or gene expression level of NBN each change or not and whether the intrinsic activity (functional activity) of MRE 11 protein and the intrinsic activity (functional activity) of NBS 1 protein each change or not can be confirmed and determined by, for example, methods similar to the above-mentioned method for confirming and determining whether the intrinsic gene structure or gene expression level of RAD 50 changes or not and the above-mentioned method for confirming and determining whether the intrinsic activity (functional activity) of RAD 50 protein changes or not, respectively. For MRE 11 protein, it is also possible to perform the confirmation and determination by, for example, a method for measuring and determining whether intracellular MRE 11 protein purified by an immunoprecipitation method or the like cleaves substrate DNA, and on the basis of whether the change occurs or not in comparison with a control (e.g. a healthy subject or a non-cancer tissue in the same patient) (preferably whether a decrease occurs or not, i.e. whether activity decreases or not as compared to the control).

Specific examples of the MRE 11 mutation which causes a change in activity of MRE 11 protein include p.I93Ffs*17 (COSMIC Legacy Mutation ID: COSM6975993), p.R188Kfs*9 (COSMIC Legacy Mutation ID: COSM8923701), p.V198* (COSMIC Legacy Mutation ID: COSM6938551), p.F321Lfs*8 (COSMIC Legacy Mutation ID: COSM6927045), p.N322* (COSMIC Legacy Mutation ID: COSM5176176), p.F399Sfs*29 (COSMIC Legacy Mutation ID: COSM2061331), p.T481Hfs*43 (COSMIC Legacy Mutation ID: COSM2061313), p.Q482Afs*4 (COSMIC Legacy Mutation ID: COSM6909136), p.N511Ifs*13 (COSMIC Legacy Mutation ID: COSM1357925), p.A526Gfs*16 (COSMIC Legacy Mutation ID: COSM7513337), p.Q629Afs*9 (COSMIC Legacy Mutation ID: COSM6920246), and p.D647Yfs*28 (COSMIC Legacy Mutation ID: COSM6962317).

Specific examples of the NBN mutation which causes a change in activity of NBS 1 protein include p.N30Tfs*5 (COSMIC Legacy Mutation ID: COSM6978819), p.D61* (COSMIC Legacy Mutation ID: COSM7449862), p.S72Lfs*20 (COSMIC Legacy Mutation ID: COSM8559558), p.M83Cfs*9 (COSMIC Legacy Mutation ID: COSM6722467), p.G103Efs*6 (COSMIC Legacy Mutation ID: COSM391695), p.K125Rfs*34 (COSMIC Legacy Mutation ID: COSM28402), p.V153Kfs*17 (COSMIC Legacy Mutation ID: COSM6959155), p.G206Lfs*26 (COSMIC Legacy Mutation ID: COSM6981006), p.K219Nfs*16 (COSMIC Legacy Mutation ID: COSM1740923), p.K233Sfs*5 (COSMIC Legacy Mutation ID: COSM9494223), p.S240Cfs*8 (COSMIC Legacy Mutation ID: COSM6924583), p.F316Sfs*2 (COSMIC Legacy Mutation ID: COSM7450031), p.N440Kfs*2 (COSMIC Legacy Mutation ID: COSM7513565), p.R466Gfs*18 (COSMIC Legacy Mutation ID: COSM1458550), p.R466Kfs*5 (COSMIC Legacy Mutation ID: COSM8498945), p.L490* (COSMIC Legacy Mutation ID: COSM2790257), p.N503Kfs*2 (COSMIC Legacy Mutation ID: COSM9061551), p.E505Gfs*6 (COSMIC Legacy Mutation ID: COSM7513880), p.R551Gfs*8 (COSMIC Legacy Mutation ID: COSM1458549), p.R551Kfs*5 (COSMIC Legacy Mutation ID: COSM6918499), p.M553Wfs*6 (COSMIC Legacy Mutation ID: COSM6955358), p.L654Afs*5 (COSMIC Legacy Mutation ID: COSM1458548), p.A713Gfs*29 (COSMIC Legacy Mutation ID: COSM6983893), and p.N731Ifs*20 (COSMIC Legacy Mutation ID: COSM30401).

[DNA 2]

The "DNA 2" in the present invention is a gene encoding a protein involved in a DNA repair mechanism (in particular, a double-stranded DNA homologous end repair mechanism) (herein, sometimes referred to as "DNA 2 protein") together with a MRN complex. The DNA 2 protein is a nuclease capable of degrading DNA as an exonuclease at an end and as an endonuclease at an internal site of DNA, which is also helicase capable of dissociating double-stranded DNA into single-stranded DNA. A typical nucleotide sequence of human-derived natural DNA 2 genome DNA is set forth as SEQ ID NO: 13, and a typical amino acid sequence of human-derived natural DNA 2 protein is set forth as SEQ ID NO: 14. Even among DNA 2s which do not have mutations associated with substitution, deletion, insertion, addition and the like of amino acid sequences, there may be an interindividual difference in sequence due to polymorphism or the like.

Examples of the "DNA 2 mutation" in the present invention include substitution, deletion, insertion and addition of amino acids in the amino acid sequence of DNA 2 protein. The DNA 2 mutation is not particularly limited as long as it is a mutation in which the intrinsic activity of DNA 2 protein changes, and the DNA 2 mutation is preferably a mutation which causes a decrease in activity of DNA 2 protein (including complete loss of activity (deactivation) of DNA 2 protein), i.e. a loss-of-function mutation. A decrease in activity of DNA 2 protein can be caused by, for example, a change in gene structure such as a missense mutation in DNA 2, a nonsense mutation over the entire region, or total or partial deletion of DNA 2, or a change in gene expression level, but is not limited thereto.

Whether the intrinsic gene structure or gene expression level of DNA 2 changes or not and whether the intrinsic activity (functional activity) of DNA 2 protein changes or not can be confirmed and determined by, for example, methods similar to the above-mentioned method for confirming and determining whether the intrinsic gene structure or gene expression level of RAD 50 changes or not and the above-mentioned method for confirming and determining whether the intrinsic activity (functional activity) of RAD 50 protein changes or not, respectively.

Specific examples of the DNA 2 mutation which causes such a change in activity of DNA 2 protein include p.K590Nfs*5 (COSMIC Legacy Mutation ID: COSM8485077), p.L697Ffs*28 (COSMIC Legacy Mutation ID: COSM1348694), p.L776Ffs*9 (COSMIC Legacy Mutation ID: COSM5081629), p.L776Pfs*24 (COSMIC Legacy Mutation ID: COSM7631030), p.S779Tfs*20 (COSMIC Legacy Mutation ID: COSM4747435), p.S779Ffs*7 (COSMIC Legacy Mutation ID: COSM5092627), p.S779Hfs*6 (COSMIC Legacy Mutation ID: COSM295321), p.S779Ffs*21 (COSMIC Legacy Mutation ID: COSM2159320), p.V825Cfs*5 (COSMIC Legacy Mutation ID: COSM6645872), p.I940Lfs*8 (COSMIC Legacy Mutation ID: COSM5423531), and p.S975Vfs*4 (COSMIC Legacy Mutation ID: COSM1727571).

[RBBP 8]

The "RBBP 8" in the present invention is a gene encoding CtIP being a protein involved in a DNA repair mechanism (in particular, a double-stranded DNA homologous end repair mechanism) (herein, sometimes referred to as "CtIP protein") together with a MRN complex. The CtIP protein is a nuclease capable of degrading DNA as an exonuclease at an internal site of DNA. A typical nucleotide sequence of human-derived natural RBBP 8 genome DNA (genome DNA encoding CtIP) is set forth as SEQ ID NO: 15, and a typical amino acid sequence of human-derived natural CtIP protein is set forth as SEQ ID NO: 16. Even among RBBP 8s which do not have mutations associated with substitution, deletion, insertion, addition and the like of amino acid sequences, there may be an interindividual difference in sequence due to polymorphism or the like.

Examples of the "RBBP 8 mutation" in the present invention include substitution, deletion, insertion and addition of amino acids in the amino acid sequence of CtIP protein. The RBBP 8 mutation is not particularly limited as long as it is a mutation in which the intrinsic activity of CtIP protein changes, and the RBBP 8 mutation is preferably a mutation which causes a decrease in activity of CtIP protein (including complete loss of activity (deactivation) of CtIP protein), i.e. a loss-of-function mutation. A decrease in activity of CtIP protein can be caused by, for example, a change in gene structure such as a missense mutation in RBBP 8, a nonsense mutation over the entire region, or total or partial deletion of RBBP 8, or a change in gene expression level, but is not limited thereto.

Whether the intrinsic gene structure or gene expression level of RBBP 8 changes or not and whether the intrinsic activity (functional activity) of CtIP protein changes or not can be confirmed and determined by, for example, methods similar to the above-mentioned method for confirming and determining whether the intrinsic gene structure or gene expression level of RAD 50 changes or not and the above-mentioned method for confirming and determining whether the intrinsic activity (functional activity) of RAD 50 protein changes or not, respectively.

Specific examples of the RBBP 8 mutation which causes such a change in activity of CtIP protein include p.R100Pfs*8 (COSMIC Legacy Mutation ID: COSM1744943), p.H183Pfs*11 (COSMIC Legacy Mutation ID: COSM9138797), p.S231 M235del (COSMIC Legacy Mutation ID: COSM7203765), p.L286Tfs*24 (COSMIC Legacy Mutation ID: COSM1745525), p.K357Nfs*3 (COSMIC Legacy Mutation ID: COSM8188329), p.H358Tfs*8 (COSMIC Legacy Mutation ID: COSM1744941), p.T375Nfs*2 (COSMIC Legacy Mutation ID: COSM8188329), p.E455Tfs*2 (COSMIC Legacy Mutation ID: COSM4720593), p.F479Efs*4 (COSMIC Legacy Mutation ID: COSM1263883), p.F650Kfs*16 (COSMIC Legacy Mutation ID: COSM4189100), p.V672Efs*2 (COSMIC Legacy Mutation ID: COSM1190926), p.K801Efs*14 (COSMIC Legacy Mutation ID: COSM7088614), p.E803Rfs*12 (COSMIC Legacy Mutation ID: COSM2885323), and p.L808Tfs*7 (COSMIC Legacy Mutation ID: COSM7513270).

[Detection of Mutation]

Any of the methods for "detection of TTK mutation", "detection of RAD 50 mutation", "detection of MRE 11 mutation", "detection of NBN mutation", "detection of DNA 2 mutation" and "detection of RBBP 8 mutation" is not particularly limited, and the methods each independently include the following method.

In the present invention, the "detection of mutation" means that the mutation of each gene on genome DNA is detected, and when the mutation on genome DNA is reflected in a change of a base in a transcription product or a change of an amino acid in a translation product, the detection of mutation of the gene also includes detection of the change of the transcription product or the translation product (i.e. indirect detection).

The preferred aspect of the method of the present invention is a method in which a mutation is detected by directly determining the nucleotide sequences of gene regions in which the mutations of cancer cells are detected (a gene region in which the first group mutation is detected: at least one selected from a TTK gene region and a RAD 50 gene region (herein, sometimes referred to as a "first group gene region"); and (a gene region in which the second group mutation is detected: at least one selected from a RAD 50 gene region, a MRE 11 gene region, a NBN gene region, a DNA 2 gene region and a RBBP 8 gene region (herein, sometimes referred to as a "second group gene region")). In the present invention, the "TTK gene region", the "RAD 50 gene region", the "MRE 11 gene region", the "NBN gene region", the "DNA 2 gene region" and the "RBBP 8 gene region" mean a certain region on genome DNA which contains TTK, a certain region on genome DNA which contains RAD 50, a certain region on genome DNA which contains MRE 11, a certain region on genome DNA which contains NBN, a certain region on genome DNA which contains DNA 2, and a certain region on genome DNA which contains RBBP 8. The regions also each independently include an expression control region for the relevant gene (e.g. promotor region or enhancer region), a 3'-end untranslated region for the relevant gene, and the like.

In this method, first, a DNA sample is prepared from a biological sample. Examples of the DNA sample include genome DNA samples, and cDNA samples prepared by reverse transcription from RNA.

The method for extracting genome DNA or RNA from a biological sample is not particularly limited, and a known method can be appropriately selected and used. Examples of the method for extracting genome DNA include a SDS phenol method (a method in which protein of a tissue stored in a urea-containing solution or ethanol is denatured with a proteinase (proteinase K), a surfactant (SDS) and phenol, and DNA is precipitated and extracted from the tissue with ethanol), and DNA extraction methods using Clean Columns (registered trademark, manufactured by NexTec Co., Ltd.), AquaPure (registered trademark, manufactured by Bio-Rad Laboratories, Inc.), ZR Plant/Seed DNA Kit (manufactured by Zymo Research), AquaGenomicSolution (registered trademark, manufactured by Mo Bi Tec GmbH), prepGEM (registered trademark, manufactured by ZyGEM LLC) and BuccalQuick (registered trademark, manufactured by Trim-Gen Corporation).

Examples of the method for extracting RNA from a biological sample and the method for preparing cDNA from the extracted RNA include methods similar to the above-mentioned method for detecting the expression level of helicase at a transcriptional level.

In this aspect, subsequently, DNA containing the first group gene region or the second group gene region is isolated, and the nucleotide sequence of the isolated DNA is determined. The isolation of DNA can be performed by PCR with genome DNA or RNA as a template, or the like using a pair of oligonucleotide primers designed to sandwich all or part of the first group gene region or the second group gene region. The determination of the nucleotide sequence of the isolated DNA can be performed by a method known to those skilled in the art, such as a Maxam-Gilbert method or a Sanger method.

By comparing the determined nucleotide sequence of DNA or cDNA (for example, when the biological sample is a cancer patient-derived sample, the nucleotide sequence of DNA or cDNA derived from a non-cancer tissue in the same patient), the presence or absence of a mutation in the first group gene region or the second group gene region in a cancer cell of the biological sample can be determined.

As the method for detecting a mutation in the first group gene region or the second group gene region, various methods capable of detecting a mutation can be used in addition to methods for directly determining the nucleotide sequence of DNA or cDNA.

For example, the detection of a mutation in the present invention can also be performed by the following method. First, a DNA or cDNA sample is prepared from a biological sample. Subsequently, an oligonucleotide probe is prepared which has a nucleotide sequence complementary to a nucleotide sequence containing a mutation site of the first group gene region or the second group gene region and is labeled with a reporter fluorescent dye and a quencher fluorescent dye. The oligonucleotide probe is hybridized to the DNA or cDNA sample, and the nucleotide sequence containing the mutation site of the first group gene region or the second group gene region is amplified using as a template the DNA or cDNA sample to which the oligonucleotide probe is hybridized. Fluorescence generated by the reporter fluorescent dye due to degradation of the oligonucleotide probe which is caused by the amplification is detected, and the detected fluorescence is then compared to a control. Examples of such a method include a double-dye probe method, so called a TaqMan (registered trademark) probe method.

In still another method, a DNA or cDNA sample is prepared from a biological sample. Subsequently, in a reaction system containing an intercalator which generated fluorescence when inserted between DNA double strands, a nucleotide sequence containing a mutation site of the first group gene region or the second group gene region is amplified using the DNA or cDNA sample as a template. The temperature of the reaction system is changed, a variation in intensity of fluorescence generated by the intercalator is detected, and the variation in intensity of the fluorescence with the detected change in temperature is compared to a control. Examples of such a method include a HRM (high resolution melting) analysis method.

In still another method, first, a DNA or cDNA sample is prepared from a biological sample. Subsequently, DNA containing all or part of the first group gene region or the second group gene region is amplified. Further, the amplified DNA is cleaved by a restriction enzyme. Subsequently, DNA fragments are separated according to the sizes thereof. Subsequently, the size of the detected DNA fragment is compared to a control. Examples of such a method include methods utilizing restriction fragment length polymorphism (RFLP), and a PCR-RFLP method.

In still another method, first, a DNA or cDNA sample is prepared from a biological sample. Subsequently, DNA containing all or part of the first group gene region or the second group gene region is amplified. Further, the amplified DNA is dissociated into single-stranded DNA. Subsequently, the dissociated single-stranded DNA is separated on a non-denaturing gel. The mobility of the separated single-stranded DNA on the gel is compared to a control. Examples of such a method include a PCR-SSCP (single-strand conformation polymorphism) method.

In still another method, first, a DNA or cDNA sample is prepared from a biological sample. Subsequently, DNA containing all or part of the first group gene region or the second group gene region is amplified. Further, the amplified DNA is separated on a gel in which the concentration of a DNA denaturant increases in steps. Subsequently, the mobility of the separated DNA on the gel is compared to a control. Examples of such a method include a denaturant gradient gel electrophoresis (DGGE) method.

As still another method, there is a method using DNA prepared from a biological sample and containing a mutation site of the first group gene region or the second group gene region, and a substrate on which an oligonucleotide probe hybridized to the DNA is fixed. Examples of such a method include a DNA array method.

In still another method, first, a DNA or cDNA sample is prepared from a biological sample. An "oligonucleotide primer having a nucleotide sequence complementary to bases on the 3' side of the bases of all or part of the first group gene region or the second group gene region by one base and a nucleotide sequence on the 3' side thereof" is prepared. Subsequently, with the DNA as a template, a fluorescent label ddNTP primer elongation reaction is carried out using the primer. Subsequently, the primer elongation reaction product is applied to a DNA sequencer, and the nucleotide sequence is determined on the basis of the length of the elongation reaction product and the fluorescence. Subsequently, the gene type is determined from the result from the DNA sequencer. Subsequently, the determined gene type is compared to a control. Examples of such a method include a Sanger method.

In still another method, first, a DNA or cDNA sample is prepared from a biological sample. Subsequently, an oligonucleotide probe consisting of 5'-"nucleotide sequence complementary to the bases of all or part of the first group gene region or the second group gene region and a nucleotide sequence on the 5' side thereof"-"nucleotide sequence which is not hybridized to bases on the 3' side of all or part of the first group gene region or the second group gene region by one base and a nucleotide sequence on the 3' side thereof"-3' (flap) is prepared. An "oligonucleotide probe having a nucleotide sequence complementary to the bases of all or part of the first group gene region or the second group gene region and a nucleotide sequence on the 3' side thereof" is prepared. Subsequently, the two oligonucleotide probes are hybridized to the prepared DNA or cDNA sample. Subsequently, the hybridized DNA is cleaved by a single-stranded DNA cleavage enzyme to liberate the flap. The single-stranded DNA cleavage enzyme is not particularly limited, and examples thereof include cleavases. In this method, subsequently, an oligonucleotide probe which has a sequence complementary to the flap and is labeled with reporter fluorescence and quencher fluorescence is hybridized to the flap. Subsequently, the intensity of generated fluorescence is measured. Subsequently, the measured fluorescence intensity is compared to a control. Examples of such a method include an Invader method.

In still another method, first, a DNA or cDNA sample is prepared from a biological sample. Subsequently, DNA containing all or part of the first group gene region or the second group gene region is amplified. The amplified DNA is dissociated into single-stranded DNA, and only one strand is separated from the dissociated single-stranded DNA. Subsequently, an elongation reaction is carried out base by base from near the bases of all or part of the first group gene region or the second group gene region, pyrophosphoric acid generated at this time is enzymatically caused to emit light, and the intensity of emission is measured. The measured fluorescence intensity is compared to a control. Examples of such a method include a Pyrosequencing method.

In still another method, first, a DNA or cDNA sample is prepared from a biological sample. Subsequently, DNA containing all or part of the first group gene region or the second group gene region is amplified. Subsequently, an "oligonucleotide primer having a nucleotide sequence complementary to bases on the 3' side of the bases of all or part of the first group gene region or the second group gene region by one base and a nucleotide sequence on the 3' side thereof" is prepared. Subsequently, with the amplified DNA as a template, a single-base elongation reaction is carried out using the prepared primer in the presence of a nucleotide labeled with a fluorescence polarization dye. The polarization degree of fluorescence is measured. Subsequently, the measured polarization degree of fluorescence is compared to a control. Examples of such a method include an Acy-cloPrime method.

In still another method, first, a DNA or cDNA sample is prepared from a biological sample. Subsequently, DNA containing all or part of the first group gene region or the second group gene region is amplified. Subsequently, an "oligonucleotide primer having a nucleotide sequence complementary to bases on the 3' side of the bases of all or part of the first group gene region or the second group gene region by one base and a nucleotide sequence on the 3' side thereof" is prepared. Subsequently, with the amplified DNA as a template, a single-base elongation reaction is carried out using the prepared primer in the presence of a fluorescently labeled nucleotide. Subsequently, the type of base used for the single-base elongation reaction is determined. Subsequently, the determined type of base is compared to a control. Examples of such a method include a SNuPE method.

The sample prepared from the biological sample may be protein as long as the mutation involves a change of amino acids (e.g. substitution, deletion, insertion or addition) in each protein (when the first group mutation is detected: at least one selected from TTK protein and RAD 50 protein (herein, sometimes referred to as "first group protein"); and when the second group mutation is detected: at least one selected from RAD 50 protein, MRE 11 protein, NBS 1 protein, DNA 2 protein and CtIP protein (herein, sometimes referred to as "second group protein"). Here, for detecting a mutation, a method using a molecule binding specifically to a site at which a change of amino acids occurs due to the mutation, etc. can be used.

For example, in a method for detecting protein using an antibody, first, a protein sample is prepared from a biological sample. Subsequently, an antigen-antibody reaction is carried out using an antibody specific to the first group protein or the second group protein, and the first group protein or the second group protein is detected. As such a method for detecting protein using an antibody, a method similar to the above-mentioned method for detecting protein using an antibody in the method for detecting the expression level of helicase at a translational level can be adjusted to the first group protein or the second group protein, and adopted as appropriate. From an immunohistochemical point of view, this method has an advantage that additional information such as a form or a distribution state of cancer cells in a tissue can also be obtained.

The type, the origin and the like of an antibody used are not particularly limited, and a monoclonal antibody is preferable. An oligoclonal antibody (mixture of several antibodies or dozens of antibodies) or a polyclonal antibody can also be used as long as it is possible to detect the first group protein or the second group protein with sufficient specificity. Functional fractions of antibodies such as Fab, Fab', F(ab')2, Fv, scFv, sc(Fv)$_2$, dsFv and diabodies, and multimers (e.g. dimers, trimers, tetramers and polymers) thereof can also be used. Each of the anti-TTK protein antibody, the anti-RAD 50 protein antibody, the anti-MRE 11 protein antibody, the anti-NBS 1 protein antibody, the anti-DNA 2 protein antibody and the anti-CtIP protein antibody may be a marketed product.

The first group protein or the second group protein can also be detected by mass spectrometry (MS). In particular, analysis by a mass spectrometer coupled with liquid chromatography (LC/MS) is sensitive, and therefore advantageous. As a method for detection by mass spectrometry, a method similar to the above-mentioned method for detection by mass spectrometry in the method for detecting the expression level of helicase at a translational level can be adjusted to the first group protein or the second group protein, and adopted as appropriate.

It is also possible to detect the first group protein or the second group protein by measuring the activity of each protein. For such activity, a known method or a similar method can be adopted as appropriate, and for example, the phosphorylation activity of TTK protein can be measured by detecting a phosphate group with a fluorescent material or the like. The ATPase activity of RAD 50 protein can be measured by using a luminescence ADP assay. For example, use of ADP-Glo (manufactured by Promega Corporation)

enables measurement of ATPase activity. Further, the nucle-ase activity of MRE 11 protein can be measured by a HeLa S3 assay method, an active gel method, a plasmid assay method or the like.

[Prediction of Sensitivity and Selection of Cancer Patient]

Thus, if the first group mutation is detected and/or the second group mutation is detected from a biological sample, and the biological sample is determined to be a cancer cell, the cell can be predicted to have sensitivity to a helicase inhibitor, and if the biological sample is a cancer cell contained in a cancer patient-derived sample, a cancer patient having the mutation detected in the cancer cell can be predicted to have sensitivity to treatment with a helicase inhibitor, and the cancer patient can be selected for cancer treatment with a helicase inhibitor.

Here, the "sensitivity to a helicase inhibitor" and the "sensitivity to treatment with a helicase inhibitor" is an indicator of whether or not the helicase inhibitor can exhibit a therapeutic effect on a cancer cell. The sensitivity includes acceleration of death of cancer cells and suppression of growth of cancer cells by the helicase inhibitor. The predic-tion of sensitivity may include not only determination of the presence or absence of sensitivity, but also evaluation of whether sensitivity can be evaluated or not, etc., and evalu-ation of the degree of sensitivity when the sensitivity is present (e.g. evaluation of whether high sensitivity can be expected, moderate sensitivity can be expected, or the like). Therefore, a patient for cancer treatment may be selected in line with, for example, a level at which moderate sensitivity can be expected depending on the type and the degree of the first group mutation and/or the second group mutation.

On the other hand, if the first group mutation and/or the second group mutation are not observed in a cancer patient-derived sample, the patient can be excluded from subjects for cancer treatment with a helicase inhibitor. This enables improvement of the success ratio of the treatment.

(MSH3)

In the present invention, it has been found that when the cancer cell targeted by a helicase inhibitor is a cancer cell having the first group mutation and/or the second group mutation, more preferably the first group mutation (TTK mutation and/or RAD 50 mutation), and further having MSH 3 mutation, the helicase inhibitor can suppress growth of the cancer cell at an equivalent or greater level. Therefore, in each of the cancer cell sensitivity prediction method, the cancer patient sensitivity prediction method and the cancer patient selection method, whether MSH 3 mutation is detected or not can be an additional indicator, and the present invention also provides a method for predicting sensitivity of a cancer cell to a helicase inhibitor (cancer cell sensitivity prediction method), the method comprising the steps of:

(a) detecting the presence or absence of at least one mutation selected from the first group consisting of TTK mutation and RAD 50 mutation in a cancer cell; and (c) detecting the presence or absence of MSH 3 mutation in the cancer cell; and (d) predicting a cancer cell having MSH 3 mutation detected in addition to TTK mutation and/or RAD 50 mutation, as having sensitivity to a helicase inhibitor;

a method for predicting sensitivity of a cancer patient to treatment with a helicase inhibitor (cancer patient sen-sitivity prediction method), the method comprising the steps of:

(a) detecting the presence or absence of at least one mutation selected from the first group consisting of TTK mutation and RAD 50 mutation in a cancer cell contained in a cancer patient-derived sample;

(c) detecting the presence or absence of MSH 3 mutation in the cancer cell contained in the cancer patient-derived sample; and (d) predicting a cancer patient having MSH 3 mutation detected in addition to TTK mutation and/or RAD 50 mutation in the cancer cell, as having sensitivity to treatment with a helicase inhibitor; and a method for selecting a cancer patient for cancer treat-ment with a helicase inhibitor (cancer patient selection method), the method comprising the steps of:

(a) detecting the presence or absence of at least one mutation selected from the first group consisting of TTK mutation and RAD 50 mutation in a cancer cell contained in a cancer patient-derived sample;

(c) detecting the presence or absence of MSH 3 mutation in the cancer cell contained in the cancer patient-derived sample; and (d) selecting a cancer patient having MSH 3 mutation detected in addition to TTK mutation and/or RAD 50 mutation in the cancer cell, for cancer treatment with a helicase inhibitor.

The "MSH 3" in the present invention is a gene encoding a mismatch repair protein (herein, sometimes referred to as "MSH 3 protein"). A typical nucleotide sequence of human-derived natural MSH 3 genome DNA is set forth as SEQ ID NO: 7, and a typical amino acid sequence of human-derived natural MSH 3 protein is set forth as SEQ ID NO: 8. Even among MSH 3s which do not have mutations associated with substitution, deletion, insertion, addition and the like of amino acid sequences, there may be an interindividual difference in sequence due to polymorphism or the like.

Examples of the "MSH 3 mutation" in the present inven-tion include substitution, deletion, insertion and addition of amino acids in the amino acid sequence of MSH 3 protein. The MSH 3 mutation is not particularly limited as long as it is a mutation in which the intrinsic activity of MSH 3 protein changes, and the MSH 3 mutation is preferably a mutation which causes a decrease in activity of MSH 3 protein (including complete loss of activity (deactivation) of MSH 3 protein), i.e. a loss-of-function mutation. A decrease in activity of MSH 3 protein can be caused by, for example, a change in gene structure such as a missense mutation in MSH 3, a nonsense mutation over the entire region, or total or partial deletion of MSH 3, or a change in gene expression level, but is not limited thereto.

Whether the intrinsic gene structure or gene expression level of MSH 3 changes or not can be confirmed and determined by, for example, the following method: acqui-sition of the nucleotide sequence of MSH 3 by a sequence of genome DNA; detection of fluorescence by a oligonucle-otide probe binding specifically to the nucleotide sequence of MSH 3; detection by a PCR method using an oligonucle-otide primer binding specifically to the nucleotide of MSH 3; or the like, and on the basis of whether the gene structure or gene expression level changes or not in comparison with a control (e.g. a healthy subject or a non-cancer tissue in the same patient) (preferably whether a loss-of-function muta-tion occurs or not, or the expression level of mRNA decreases or not).

Whether the intrinsic activity (functional activity) of MSH 3 protein changes or not can be confirmed and determined by, for example, the following method: an immunostaining method or a Western blotting method using an antibody binding specifically to MSH 3 protein; a method in which whether intracellular MSH 3 protein purified by an immunoprecipitation method or the like is bound to MSH 2 that is constituent protein of the MutS β complex is determined by a Western blotting method etc.; a method in which whether intracellular MSH 3 protein purified by an immunoprecipitation method or the like has ATPase activity is determined by an ATPase activity measurement method; or the like, and on the basis of whether the activity changes or not in comparison with a control (e.g. a healthy subject or a non-cancer tissue in the same patient) (preferably whether the activity decreases or not, i.e. whether the expression level of MSH 3 protein detected by the immunostaining method or the Western blotting method decreases or not as compared to the control, whether the molecular weight of protein detected by the Western blotting method changes or not as compared to the control, whether the amount of MSH 2 that is constituent protein of the MutS β complex bound to MSH 3 protein detected by the Western blotting method decreases or not as compared to the control, or whether the ATPase activity decreases or not as compared to the control).

Specific examples of the MSH 3 mutation which causes a change in activity of MSH 3 protein include p.A22Rfs*3 (COSMIC Legacy Mutation ID: COSM7212418), p.P67Qfs*13 (COSMIC Legacy Mutation ID: COSM5989630), p.P67Qfs*13 (COSMIC Legacy Mutation ID: COSM5356342), p.V292Mfs*15 (COSMIC Legacy Mutation ID: COSM9494178), p.K383Gfs*20 (COSMIC Legacy Mutation ID: COSM1568178), p.K383Rfs*32 (COSMIC Legacy Mutation ID: COSM1438888), p.L503Wfs*5 (COSMIC Legacy Mutation ID: COSM5835081), p.P783Ffs*19 (COSMIC Legacy Mutation ID: COSM4188468), p.E797Sfs*3 (COSMIC Legacy Mutation ID: COSM8468896), p.N861Mfs*6 (COSMIC Legacy Mutation ID: COSM1438891), p.L1006Vfs*10 (COSMIC Legacy Mutation ID: COSM3139259), p.N1020IMfs*40 (COSMIC Legacy Mutation ID: COSM1438892), p.G1062Nfs*12 (COSMIC Legacy Mutation ID: COSM9358418), p.N212Sfs*2 (COSMIC Legacy Mutation ID: COSM9178646), p.E261Gfs*43 (COSMIC Legacy Mutation ID: COSM5868883), p.N385Qfs*19 (COSMIC Legacy Mutation ID: COSM1735453), p.Q406Pfs*42 (COSMIC Legacy Mutation ID: COSM9494259), p.P740Afs*28 (COSMIC Legacy Mutation ID: COSM5701238), p.I785Yfs*18 (COSMIC Legacy Mutation ID: COSM7513821), p.L821Ffs*3 (COSMIC Legacy Mutation ID: COSM4603915), p.N861Kfs*8 (COSMIC Legacy Mutation ID: COSM8183447), p.N1020Kfs*17 (COSMIC Legacy Mutation ID: COSM8565481), and p.E1092Rfs*24 (COSMIC Legacy Mutation ID: COSM8851685).

As a method for detecting MSH 3 mutation, a method similar to the above-mentioned method for "detecting TTK" etc. in [Detection of mutation] above can be adjusted to MSH 3 mutation, and adopted as appropriate.

(Third Group Mutation)

Further, in the present invention, it has been found that when the cancer cell targeted by a helicase inhibitor is a cancer cell having the first group mutation and/or the second group mutation, more preferably the second group mutation, and further having at least one mutation selected from the third group consisting of EXO 1 mutation, RPA 1 mutation, RPA 2 mutation and RPA 3 mutation (herein, sometimes referred to as "third group mutation", the helicase inhibitor can suppress growth of the cancer cell at an equivalent or greater level. Therefore, in each of the cancer cell sensitivity prediction method, the cancer patient sensitivity prediction method and the cancer patient selection method, whether the third group mutation is detected or not can also be taken as an indicator, and the present invention also provides a method for predicting sensitivity of a cancer cell to a helicase inhibitor (cancer cell sensitivity prediction method), the method comprising the steps of:

(a) detecting the presence or absence of at least one mutation selected from the second group consisting of RAD 50 mutation, MRE 11 mutation, NBN mutation, DNA 2 mutation and RBBP 8 mutation in a cancer cell;

(c) detecting the presence or absence of the third group consisting of EXO 1 mutation, RPA 1 mutation, RPA 2 mutation and RPA 3 mutation in a cancer cell; and (d) predicting a cancer cell having the third group mutation detected in addition to the second group mutation, as having sensitivity to a helicase inhibitor;

a method for predicting sensitivity of a cancer patient to treatment with a helicase inhibitor (cancer patient sensitivity prediction method), the method comprising the steps of:

(a) detecting the presence or absence of at least one mutation selected from the second group consisting of RAD 50 mutation, MRE 11 mutation, NBN mutation, DNA 2 mutation and RBBP 8 mutation in a cancer cell contained in a cancer patient-derived sample;

(c) detecting the presence or absence of the mutation of the third group consisting of EXO 1 mutation, RPA 1 mutation, RPA 2 mutation and RPA 3 mutation in a cancer cell contained in a cancer patient-derived sample; and (d) predicting a cancer patient having the third group mutation detected in addition to the second group mutation in the cancer cell, as having sensitivity to treatment with a helicase inhibitor; and a method for selecting a cancer patient for cancer treatment with a helicase inhibitor, the method comprising the step of:

(a) detecting the presence or absence of at least one mutation selected from the second group consisting of RAD 50 mutation, MRE 11 mutation, NBN mutation, DNA 2 mutation and RBBP 8 mutation in a cancer cell contained in a cancer patient-derived sample;

(c) detecting the presence or absence of the mutation of the third group consisting of EXO 1 mutation, RPA 1 mutation, RPA 2 mutation and RPA 3 mutation in a cancer cell contained in a cancer patient-derived sample; and (d) selecting a cancer patient having the third group mutation detected in addition to the second group mutation in the cancer cell, for cancer treatment with a helicase inhibitor.

[EXO 1]

The "EXO 1" in the present invention is a gene encoding a protein that is 3'→5' exonuclease which liberates 5'-mononucleotide from the 3'-OH end of single-stranded DNA by catalyzing hydrolysis of a phosphorylated ester of DNA, the protein having RNase activity (herein, sometimes referred to as "EXO 1 protein"). The exonuclease activity of EXO 1 protein has been reported to be involved in a DNA repair mechanism (in particular, double-stranded homologous end repair mechanism) in cooperation with the endonuclease activity of MRE 11 protein. A typical nucleotide sequence of human-derived natural EXO 1 genome DNA is set forth as SEQ ID NO: 17, and a typical amino acid sequence of human-derived natural EXO 1 protein is set forth as SEQ ID NO: 18. Even among EXO 1s which do not have mutations associated with substitution, deletion, insertion, addition and the like of amino acid sequences, there may be an interindividual difference in sequence due to polymorphism or the like.

Examples of the "EXO 1 mutation" in the present invention include substitution, deletion, insertion and addition of amino acids in the amino acid sequence of EXO 1 protein. The EXO 1 mutation is not particularly limited as long as it is a mutation in which the intrinsic activity of EXO 1 protein changes, and the EXO 1 mutation is preferably a mutation which causes a decrease in activity of EXO 1 protein (including complete loss of activity (deactivation) of EXO 1 protein), i.e. a loss-of-function mutation. A decrease in activity of EXO 1 protein can be caused by, for example, a change in gene structure such as a missense mutation in EXO 1, a nonsense mutation over the entire region, or total or partial deletion of EXO 1, or a change in gene expression level, but is not limited thereto.

Whether the intrinsic gene structure or gene expression level of EXO 1 changes or not can be confirmed and determined by, for example, the following method: acquisition of the nucleotide sequence of EXO 1 by a sequence of genome DNA; detection of fluorescence by a oligonucleotide probe binding specifically to the nucleotide sequence of EXO 1; detection by a PCR method using an oligonucleotide primer binding specifically to the nucleotide of EXO 1; or the like, and on the basis of whether the gene structure or gene expression level changes or not in comparison with a control (e.g. a healthy subject or a non-cancer tissue in the same patient) (preferably whether a loss-of-function mutation occurs or not, or the expression level of mRNA decreases or not).

Whether the intrinsic activity (functional activity) of EXO 1 protein changes or not can be confirmed and determined by, for example, the following method: an immunostaining method or a Western blotting method using an antibody binding specifically to EXO 1 protein; a method in which whether intracellular EXO 1 protein purified by an immunoprecipitation method or the like cleaves the 3'-end of substrate single-stranded DNA; or the like, and on the basis of whether the activity changes or not in comparison with a control (e.g. a healthy subject or a non-cancer tissue in the same patient) (preferably whether the activity decreases or not, i.e. whether the expression level of protein detected by the immunostaining method or the Western blotting method decreases or not as compared to the control, whether the molecular weight of protein detected by the Western blotting method changes or not as compared to the control, or whether the exonuclease activity decreases or not as compared to the control).

Specific examples of the EXO 1 mutation which causes such a change in activity of EXO 1 protein include p.E89Dfs*44 (COSMIC Legacy Mutation ID: COSM5832542), p.V142* (COSMIC Legacy Mutation ID: COSM6657048), p.N159Tfs*9 (COSMIC Legacy Mutation ID: COSM5661778), p.G190Wfs*5 (COSMIC Legacy Mutation ID: COSM392303), p.F215Lfs*9 (COSMIC Legacy Mutation ID: COSM166045), p.C508Afs*13 (COSMIC Legacy Mutation ID: COSM1340675), p.C508Lfs*7 (COSMIC Legacy Mutation ID: COSM5207739), p.R723Ffs*20 (COSMIC Legacy Mutation ID: COSM9226806), and p.D731Tfs*4 (COSMIC Legacy Mutation ID: COSM6657053).

As a method for detecting EXO 1 mutation, a method similar to the above-mentioned method for "detecting TTK mutation" etc. in [Detection of mutation] above can be adjusted to EXO 1 mutation, and adopted as appropriate.

[RPA 1, RPA 2 and RPA 3]

Each of "RPA 1", "RPA 2" and "RPA 3" in the present invention has been reported to be a gene encoding proteins which mutually interact to form a replication protein (RPA) and interact with a MRN complex (e.g. Greg Oakley, et al., Biochemistry., 2009 August 11, 48 (31), p. 7473-7481; and Ting Liu et al., Acta Biochim Biophys Sin, 2016, 48 (7), p. 665-670) (herein, sometimes referred, respectively, to as "RPA 1 protein", "RPA 2 protein" and "RPA 3 protein", which are sometimes referred to collectively as "RPA 1 to 3 protein". If the function of one of these proteins is deleted, the function of the complex itself decreases, so that the DNA repair mechanism does not normally function. Therefore, particularly for RPA 1, RPA 2 and RPA 3 (hereinafter, sometimes referred to collectively as "RPA 1 to 3" encoding a protein forming such a complex, among the third group mutations, it is preferable to detect at least one of these mutations.

Typical nucleotide sequences of human-derived natural RPA 1 to 3 genome DNAs are set forth as SEQ ID NOS: 19, 21 and 23, respectively, and typical amino acid sequences of human-derived natural RPA 1 to 3 proteins are set forth as SEQ ID NOS: 20, 22 and 24, respectively. Even among RPA 1s, RPA 2s or RPA 3s which do not have mutations associated with substitution, deletion, insertion, addition and the like of amino acid sequences, there may be an interindividual difference in sequence due to polymorphism or the like.

Examples of the "RPA 1 mutation", the "RPA 2 mutation" and the "RPA 3 mutation" (hereinafter, referred to as "RPA 1 to 3 mutation") in the present invention include substitution, deletion, insertion and addition of amino acids in the amino acid sequences of RPA 1 to 3 protein, respectively. The RPA 1 to 3 mutation is not particularly limited as long as it is a mutation in which the intrinsic activity, respectively, of RPA 1 to 3 protein changes, and the RPA 1 to 3 mutation is preferably a mutation which causes a decrease in activity of RPA 1 to 3 protein (including complete loss of activity (deactivation) of RPA 1 to 3 protein), i.e. a loss-of-function mutation. A decrease in activity of RPA 1 to 3 protein can be caused by, for example, a change in gene structure such as a missense mutation, respectively, in RPA 1 to 3, a nonsense mutation over the entire region, or total or partial deletion of RPA 1 to 3, or a change in gene expression level, but is not limited thereto.

Whether the intrinsic gene structure or gene expression level of RPA 1 to 3 changes or not can be confirmed and determined by, for example, the following method: acquisition of the nucleotide sequence of RPA 1 to 3 by a sequence of genome DNA; detection of fluorescence by a oligonucleotide probe binding specifically to the nucleotide sequence of RPA 1 to 3; detection by a PCR method using an oligonucleotide primer binding specifically to the nucleotide of RPA 1 to 3; or the like, and on the basis of whether the gene structure or gene expression level changes or not in comparison with a control (e.g. a healthy subject or a non-cancer tissue in the same patient) (preferably whether a loss-of-function mutation occurs or not, or the expression level of mRNA decreases or not).

Whether the intrinsic activity (functional activity) of RPA 1 to 3 protein changes or not can be confirmed and determined by, for example, the following method: an immunostaining method or a Western blotting method using an antibody binding specifically to RPA 1 to 3 protein; a method in which whether intracellular RPA 1 to 3 protein purified by an immunoprecipitation method or the like is bound to other RPA 1 to 3 protein that is constituent protein of the complex is determined by a Western blotting method etc.; or the like, and on the basis of whether the activity changes or not in comparison with a control (e.g. a healthy subject or a non-cancer tissue in the same patient) (preferably whether the activity decreases or not, i.e. whether the expression level of RPA 1 to 3 protein detected by the immunostaining method or the Western blotting method decreases or not as compared to the control, whether the molecular weight of protein detected by the Western blotting method changes or not as compared to the control, or whether the amount of other RPA 1 to 3 protein that is constituent protein of the complex detected by the Western blotting method decreases or not as compared to the control).

Specific examples of the RPA 1 mutation which causes such a change in activity of RPA 1 to 3 protein include p.N274Mfs*5 (COSMIC Legacy Mutation ID: COSM4722502), p.N338Kfs*28 (COSMIC Legacy Mutation ID: COSM1745322), p.E363Gfs*4 (COSMIC Legacy Mutation ID: COSM6048715), p.E418Kfs*5 (COSMIC Legacy Mutation ID: COSM111541), p.E601Vfs*53 (COSMIC Legacy Mutation ID: COSM8515054), and p.S609Rfs*46 (COSMIC Legacy Mutation ID: COSM112025). Examples of the RPA 2 mutation include p.G34Afs*69 (COSMIC Legacy Mutation ID: COSM8537429), p.V127Gfs*26 (COSMIC Legacy Mutation ID: COSM907939), and p.E158Gfs*5 (COSMIC Legacy Mutation ID: COSM8220461). Examples of the RPA 3 mutation include p.N50Mfs*6 (COSMIC Legacy Mutation ID: COSM3029082), and p.S64Nfs*26 (COSMIC Legacy Mutation ID: COSM6848181).

As a method for detecting RPA 1 to 3 mutation, a method similar to the above-mentioned method for "detecting TTK mutation" etc. in [Detection of mutation] above can be adjusted, respectively, to RPA 1 to 3 mutation, and adopted as appropriate.

(Helicase)

Further, if helicase which is a targeted by a helicase inhibitor according to the present invention is not normally expressed and/or does not normally function, it may be impossible to effectively perform cancer treatment with a helicase inhibitor. Therefore, in the cancer cell sensitivity prediction method, the cancer patient sensitivity prediction method and the cancer patient selection method, detection of a mutation of a gene encoding helicase and decrease in expression of helicase can also be taken as an indicator.

As a method for detecting a mutation of a gene encoding helicase, a method similar to the above-mentioned method for "detecting TTK mutation" etc. in [Detection of mutation] above can be adjusted to the mutation of the gene encoding helicase (e.g. WRN gene), and adopted as appropriate. The method for detecting a decrease in expression of helicase is as described above.

<Method for Treating Cancer>

The present invention provides:

a method for treating cancer, the method comprising the steps of:

(a) detecting the presence or absence of at least one mutation selected from the first group consisting of TTK mutation and RAD 50 mutation in a cancer cell contained in a cancer patient-derived cell; and (b) administering a helicase inhibitor to a cancer patient having the mutation detected in the cancer cell; and a method for treating cancer, the method comprising the steps of:

(a) detecting the presence or absence of at least one mutation selected from the second group consisting of RAD 50 mutation, MRE 11 mutation, NBN mutation, DNA 2 mutation and RBBP 8 mutation in a cancer cell contained in a cancer patient-derived sample; and (b) administering a helicase inhibitor to a cancer patient having the mutation detected in the cancer cell.

(Herein, these methods are sometimes referred to collectively as a "cancer treatment method".)

In the cancer treatment method of the present invention, the detection of the first group mutation, the detection of the second group mutation and the helicase inhibitor are as described above.

The administration of the helicase inhibitor to a cancer patient may be oral administration or parenteral administration (e.g. intravenous administration, arterial administration or topical administration).

The dosage of the helicase inhibitor administered to a cancer patient may be an amount effective for treating cancer by inhibiting helicase, and cannot be determined definitely because it is appropriately selected according to the properties of a compound inhibiting helicase, the age, the body weight, the symptom and the physical condition of a cancer patient, the advancement state of cancer, and the like. For example, when the helicase inhibitor is administered to a human, the daily dosage thereof is 0.001 to 100,000 mg, preferably 0.01 to 5,000 mg, in terms of the amount of the compound inhibiting helicase. The frequency of administration of the helicase inhibitor to a cancer patient also cannot be determined definitely, and it is preferable that for example, the helicase inhibitor be administered once or in two to four divided doses daily, with the administration being repeated at appropriate intervals. The dosage and the frequency of administration can be appropriately increased or decreased if necessary at a physician's discretion.

In this way, helicase is further inhibited in cancer cells having the first group mutation and/or the second group mutation in a cancer patient, so that the cancer can be treated by acceleration of death and/or suppression of growth of the cancer cells.

Examples of the cancer to be treated include, but are not limited to, bowel cancer, stomach cancer, uterine cervix cancer, uterine body cancer, prostate cancer, breast cancer, lung cancer, bladder cancer, esophagus cancer, head and neck cancer, kidney cancer, ovary cancer, lymphoma, adenoid cystic cancer and pancreas cancer.

<Reagent for Detecting Presence or Absence of Mutation>

The present invention also provides a reagent for detecting the presence or absence of the first group mutation and/or the second group mutation in the above-described method, the reagent comprising the molecule of at least one of:

(i) an oligonucleotide primer binding specifically to one gene selected from the first group consisting of TTK and RAD 50;

(ii) an oligonucleotide probe binding specifically to one gene selected from the first group consisting of TTK and RAD 50;

(iii) an antibody binding specifically to one protein selected from the first group consisting of TTK protein and RAD 50 protein, as an active ingredient, or the molecule of at least one of:

(i) an oligonucleotide primer binding specifically to one gene selected from the second group consisting of RAD 50, MRE 11, NBN, DNA 2 and RBBP 8;

(ii) an oligonucleotide probe binding specifically to one gene selected from the second group consisting of RAD 50, MRE 11, NBN, DNA 2 and RBBP 8; and (iii) an antibody binding specifically to one protein selected from the second group consisting of RAD 50 protein, MRE 11 protein, NBS 1 protein, DNA 2 protein and CtIP protein, as an active ingredient.

The oligonucleotide primer may be designed on the basis of nucleotide sequence information of genome DNA and cDNA of each gene (e.g. SEQ ID NOS: 3, 5, 9, 11, 13 and 15) so as to ensure that the primer is consistent with the above-mentioned method and an amplification region, and production of amplified products of genes other than desired genes is avoided as much as possible. Those skilled in the art can design such an oligonucleotide primer by a conventional method. The oligonucleotide primer has a length of typically 15 to 50 bases, preferably 15 to 30 bases, and may have a larger length depending on a method and a purpose.

The oligonucleotide probe may be designed on the basis of nucleotide sequence information of genome DNA and cDNA of each gene (e.g. SEQ ID NOS: 3, 5, 9, 11, 13 and 15) so as to ensure that the primer is consistent with the above-mentioned method and a hybridization region, and occurrence of hybridization to genes other than desired genes is avoided as much as possible. Those skilled in the art can design such an oligonucleotide probe by a conventional method. The oligonucleotide probe has a length of typically 15 to 200 bases, preferably 15 to 100 bases, still more preferably 15 to 50 bases, and may have a larger length depending on a method and a purpose.

It is preferable that the oligonucleotide probe be appropriately labeled and used. Examples of the method for performing labeling include a method in which using T4 polynucleotidekinase, the 5'-end of the oligonucleotide is phosphorylated with 32P to perform labeling; and a method in which using a DNA polymerase such as Klenow enzyme, a substrate base labeled with an isotope such as 32P, a fluorescent dye, biotin or the like with a random hexamer oligonucleotide or the like as a primer is incorporated (random priming method).

The oligonucleotide primer and the oligonucleotide probe can be prepared by, for example, a commercially available oligonucleotide synthesizing machine. It is also possible to prepare the oligonucleotide probe as a double-stranded DNA fragment obtained by restriction enzyme treatment or the like. The oligonucleotide primer and the oligonucleotide probe according to the present invention are not required to be composed only of a natural nucleotide (deoxyribonucleotide (DNA) or ribonucleotide (RNA)), and all or part thereof may be composed of a non-natural nucleotide. Examples of the non-natural nucleotide include PNA (polyamide nucleic acid), LNA (registered trademark, locked nucleic acid), ENA (registered trademark, 2'-0,4'-C-ethylene-bridged nucleic acids), and complexes thereof.

When the antibody binding specifically to the first group protein or the second group protein, the antibody can be obtained by immunizing an immune animal with an antigen (any of the proteins (e.g. TTK protein), a partial peptide thereof, or cells which express the protein or the peptide), and purifying antiserum of the animal by conventional means (e.g. salting-out, centrifugation, dialysis or column chromatography). The monoclonal antibody can be prepared by a hybridoma method or a recombinant DNA method.

Typical examples of the hybridoma method include a Kohler & Milstein method (Kohler & Milstein, Nature 1975; 256: 495). The antibody-producing cell used in a cell fusion step in this method is a spleen cell, a lymph node cell, a peripheral blood leukocyte or the like of an animal (e.g. mouse, rat, hamster, rabbit, monkey or goat) immunized with an antigen (any of the proteins (e.g. TTK protein), a partial peptide thereof, or cells which express the protein or the peptide). It is also possible to use antibody-producing cells obtained by applying an antigen in a culture medium to the cells or lymphocytes isolated in advance from animals which are not immunized. As a myeloma cell, any of various known cell lines can be used. The antibody-producing cell and the myeloma cell may be derived from different animal species as long as these cells can be fused with each other, and cells derived from the same animal species are preferable. The hybridoma is produced by, for example, cell fusion between a spleen cell obtained from a mouse immunized with an antigen and a mouse myeloma cell, and by subsequent screening, a hybridoma which produces a monoclonal antibody specific to the first group protein or the second group protein can be obtained. The monoclonal antibody to the first group protein or the second group protein can be obtained by culturing the hybridoma or from ascites fluid of a mammal given the hybridoma.

The recombinant DNA method is a method in which DNA encoding the antibody is cloned from a hybridoma, a B cell or the like, and incorporated into an appropriate vector, and the vector is introduced into a host cell (e.g. mammal cell line, *Bacillus coli*, yeast cell, insect cell or plant cell) to produce an antibody according to the present invention as a recombinant antibody (e.g. P. J. Delves, Antibody Production: Essential Techniques, 1997 WILEY, P. Shepherd and C. Dean Monoclonal Antibodies, 2000 OXFORD UNIVERSITY PRESS, Vandamme A M et al., Eur. J. Biochem. 1990; 192: 767-775). In expression of DNA encoding an antibody, DNAs encoding a heavy chain or a light chain may be incorporated into different expression vectors to transform the host cell, or DNAs encoding a heavy chain and a light chain may be incorporated into a single expression vector to transform the host cell (e.g. WO 94/11523). The antibody can be obtained in a substantially pure and homogeneous form by culturing the host cell, separating the antibody from the inside of the host cell or the culture solution and purifying the antibody. For the separation and purification of the antibody, a common method which is used for purification of a polypeptide can be used. When a transgenic animal (e.g. bovine, goat, sheep or pig) into which an antibody gene is incorporated is prepared using a transgenic animal preparation technique, a large amount of a monoclonal antibody derived from the antibody gene can be obtained from milk from the transgenic animal.

On the basis of the thus-obtained antibodies or genes thereof, functional fractions of antibodies such as Fab, Fab', F(ab')2, Fv, scFv, sc(Fv)$_2$, dsFv and diabodies, and multimers (e.g. dimers, trimers, tetramers and polymers) thereof can be prepared.

When the amount of an antibody bound to the first group protein or the second group protein is directly detected, the resulting anti-TTK protein antibody, anti-RAD 50 protein antibody, anti-MRE 11 protein antibody, anti-NBS 1 protein antibody, anti-DNA 2 protein antibody, anti-CtIP protein antibody and the like are directly labeled with an enzyme, a radioisotope, a fluorescent dye, an avidin-biotin system or the like and used. On the other hand, when an indirect detection method is carried out in which the amount of an antibody bound to the first group protein or the second group protein is detected using a secondary antibody etc., the resulting anti-protein antibody (e.g. anti-TTK protein antibody) (primary antibody) is not required to be labeled, and for the detection, a labeled molecule which recognizes the antibody (e.g. secondary antibody or protein A) may be used.

The reagent according to the present invention may comprise other ingredients acceptable for reagents, such as sterilized water, physiological saline, a buffering agent and a preservative if necessary in addition to the above-described molecule as an active ingredient. Further, the reagent may further comprise the molecule of at least one of oligonucleotide primers, oligonucleotide probes and antibodies for detection of MSH 3 mutation or the third group mutation, or may be combined with a reagent comprising such a molecule.

<Method for Screening Compounds to be Used for Treatment of Cancer and Cancer Therapeutic Drug>

The present invention provides:

a method for screening compounds to be used for treatment of cancer containing a cancer cell having at least one mutation detected selected from the first group consisting of TTK mutation and RAD 50 mutation, the method comprising the step of selecting a compound on the basis of whether helicase is inhibited or not; and a method for screening compounds to be used for treatment of cancer containing a cancer cell in which at least one mutation selected from the second group consisting of RAD 50 mutation, MRE 11 mutation, NBN mutation, DNA 2 mutation and RBBP 8 mutation, the method comprising the step of selecting a compound on the basis of whether helicase is inhibited or not.

(Hereinafter, these methods are sometimes referred to collectively as a "method for screening compounds".)

By using each of compounds which inhibit helicase and are screened by the method for screening compounds, there can be provided:

a cancer therapeutic drug comprising a compound, which inhibits helicase, as an active ingredient, the cancer therapeutic drug being a therapeutic drug for cancer containing a cancer cell having at least one mutation detected selected from the first group consisting of TTK mutation and RAD 50 mutation is detected; and a cancer therapeutic drug comprising a compound, which inhibits helicase, as an active ingredient, the cancer therapeutic drug being a therapeutic drug for cancer containing a cancer cell having at least one mutation detected selected from the second group consisting of RAD 50 mutation, MRE 11 mutation, NBN mutation, DNA 2 mutation and RBBP 8 mutation.

(Hereinafter, these drugs are sometimes referred to collectively as a "cancer therapeutic drug".)

The test compound applied to the method for screening compounds according to the present invention is not particularly limited, and examples thereof include at least one selected from the group consisting of the above-described compounds listed as examples of compounds which inhibit helicase, polypeptides and polynucleotides (whether they inhibit helicase or not is not required to be known). More specific examples of the test compound include synthetic low-molecular compound libraries, expressed products of gene libraries, peptide libraries, siRNA, antibodies, bacteria releasing substances, extracts and culture supernatants of cells (microorganisms, plant cells and animal cells), purified or partially purified polypeptides, marine organisms, plant or animal-derived extracts, and random phage peptide display libraries. The test compound may be a derivative of a known helicase inhibitor.

In the method for selecting a compound on the basis of whether helicase is inhibited or not (screening), a test compound may be applied to the system for confirmation of inhibition of activity or expression of helicase, followed by detecting subsequent helicase activity or expression. When the result of detection shows that the activity or expression decreases as compared to helicase activity or expression in a control (e.g. a case where the test compound is not added), it can be evaluated that helicase is inhibited.

The "helicase" which is evaluated as being inhibited or not by the compound is not particularly limited in the screening, and examples thereof include RecQ helicase (RecQ L1, BLM, WRN, RecQ L4/RTS and RecQ L5). RecQ helicase is preferable, and WRN (Werner syndrome protein) is more preferable.

The compound identified by the method for screening compounds according to the present invention can be formed into a cancer therapeutic drug as a medicament by appropriately mixing the compound with any of the pharmacologically acceptable additive ingredients mentioned for the helicase inhibitor above, etc. and subjecting the resulting mixture to formulation by a known pharmaceutical method.

EXAMPLES

Hereinafter, the present invention will be described in more detail on the basis of Test Examples, but the present invention is not limited to Examples below.

Test Example 1

1. Experimental Material and Method (1) Cell Line

First, for about 70 cancer cell lines, expression of WRN was suppressed by siRNA, and cell lines in which suppression of growth was confirmed and cell lines in which growth was not suppressed were selected. In the following test, an example is shown in which as some of the selected cell lines, HCT 116, KM 12, SW 48, CW-2, HT-29 and NCI-H 716 (bowel cancer), RL 95-2, C-33A and COLD-684 (uterus cancer), and SNU-1 and GSU (stomach cancer) were used as cancer cell lines to be tested.

HCT 116 is a cancer cell line having mutations in all of TTK, RAD 50 and MSH 3. KM 12, RI, 95-2 and C-33A are cancer cell lines having mutations in at least TTK and RAD 50. SNU-1 is a cancer cell line having mutations in at least TTK and MSH 3. SW 48 is a cancer cell line having a mutation in at least TTK. CW-2 is a cancer cell line having a mutation in at least RAD 50. COLO-684, GSU, HT-29 and NCI-H 716 are cancer cell lines which have no mutation in any of TTK and RAD 50 and which have not been reported to have MSH 3 mutation. Table 1 below shows these cancer cell lines, origin tissues thereof, and information of TTK, RAD 50 and MSH 3 mutations in the cancer cell lines (information of gene mutations causing loss-of-function mutations).

TABLE 1

| Cell line | Tissue | TTK | RAD50 | MSH3 |
|---|---|---|---|---|
| HCT 116 | Colorectal | Truncating mutation[*1] | Truncating mutation[*1] | Truncating mutation[*2] |
| KM12 | Colorectal | Truncating mutation[*1] | Truncating mutation[*1] | N.I. |
| RL95-2 | Uterus | Truncating mutation[*1] | Truncating mutation[*1] | N.I. |
| SNU-1 | Stomach | Truncating mutation[*1] | Wild type | Truncating mutation[*3] |
| SW48 | Colorectal | Truncating mutation[*1] | Wild type | N.I. |
| C-33A | Uterus | Truncating mutation[*1] | Truncating mutation[*1] | N.I. |
| CW-2 | Colorectal | Wild type | Truncating mutation[*1] | N.I. |
| COLO-684 | Uterus | Wild type | Wild type | N.I. |
| GSU | Stomach | Wild type | Wild type | N.I. |

TABLE 1-continued

| Cell line | Tissue | TTK | RAD50 | MSH3 |
|---|---|---|---|---|
| HT-29 | Colorectal | Wild type | Wild type | N.I. |
| NCI-H716 | Colorectal | Wild type | Wild type | N.I. |

In Table 1,
"*1" represents mutations disclosed in the cancer cell line database: "Cancer Cell Line Encyclopedia (CCLE)" prepared by Broad Institute,
"*2" represents mutations disclosed in Mol Cell. 2018 Jul. 19: 17 (2), p.319-331. e3,
"*3" represents mutations disclosed in Eur J Cancer. 2000 May; 36 (7), p. 925-931, and
"N.I." mean that information about mutations is not known.

(2) Small Interfering (si)RNA

For suppression of expression of WRN, ON-TARGET plus Individual siRNA (manufactured by Dharmacon, Inc.) was used. For transfection, Lipofectamine RNAiMAX (manufactured by Invitrogen Corporation) was used. WRN siRNA (WRN siRNA 1, Dharmacon, Inc. product code: J-010378-06, SEQ ID NO: 25) was used as a test substance, and non-target siRNA (non-target siRNA 1, Dharmacon, Inc. product code: D-001810-01, SEQ ID NO: 26) was used as a negative control. Each siRNA was dissolved using a 1×siRNA buffer obtained by diluting a 5×siRNA buffer (manufactured by Dharmacon: B-002000-UB-100) by 5 times with nuclease free water (AM 9932 manufactured by Ambion, Inc.).

(3) Test for Suppression of Expression of WRN

In each cancer cell line, cytotoxic activity under suppression of expression of WRN was evaluated. The cell lines were cultured in a cell culture flask (430641U manufactured by Corning Incorporated) using the culture solutions shown in Table 2 below, the cell surfaces were washed with PBS (14249-24 manufactured by nacalai tesque), trypsin (35554-64 manufactured by nacalai tesque) was then added, and the cells were incubated at 37° C. for 5 minutes, and suspended with the culture solutions. The number of cells was measured using an automatic cell counter (NC-200 manufactured by Chemometec) and Via 1-Casette (941-0011 manufactured by Chemometec), and the cell line solutions were then adjusted with the culture solutions so as to obtain the cell densities shown in Table 3 below. Each cell line solution was seeded at 100 μL/well on a 96-well plate (manufactured by Greiner Bio-One GmbH) in such a manner that the number of cells coincided with the seeding density shown in Table 3.

Subsequently, Lipofectamine RNAiMAX (13778150 manufactured by Thermo Fischer Scientific) was diluted by 50 times with Opti-Mem (31985-062 manufactured by Thermo Fischer Scientific), and then mixed with the equivalent amount of a 120 nM test substance (WRN siRNA 1) or non-target siRNA (non-target siRNA 1). The mixed solution was added at 20 μL/well to the plate on which the cells were seeded, the plate was then shaken, and the cells were each transfected with siRNA at a final concentration of 10 nM.

The cells were cultured in an incubator at 37° C. for 7 days, Cell Titer-Glo 2.0 Cell Viability Assay (G 9243 manufactured by Promega Corporation) was then added at 50 μL/well, the cells were incubated at room temperature for 5 minutes, and luminescence was then measured with EnVision (manufactured by PerkinElmer) to determine the intracellular ATP level which is a marker for cell survival. The cell survival rate under suppression of expression of WRN was calculated, where the intracellular ATP level in each cancer cell line transfected with the negative control and cultured for 7 days was defined as 100%. FIG. 1 shows the cell survival rate (% survival) under suppression of expression of WRN in each cancer cell line.

TABLE 2

| Cell line | Composition | Name of vendor (product code) |
|---|---|---|
| | | Culture solution |
| HCT 116 | McCoy's 5A | SIGMA (R8403-500 mL) |
| | 10% FBS | SIGMA (172012-500 mL) |
| KM12 | RPMI-1640 | SIGMA (R8758-500 mL) |
| | 10% FBS | SIGMA (172012-500 mL) |
| RL95-2 | DMEM:Ham's F-12 = 1:1 | Thermo Fischer Scientific (11330-032) |
| | 10% FBS | SIGMA (172012-500 mL) |
| | 5 μg/mL Insulin | Thermo Fischer Scientific (12585-014) |
| SNU-1 | RPMI-1640 | SIGMA (R8758-500 mL) |
| | 10% FBS | SIGMA (172012-500 mL) |
| SW48 | Leibovitz's (1×) L-15 medium | Thermo Fisher Scientific (11415-064) |
| | 10% FBS | SIGMA (172012-500 mL) |
| C-33A | E-MEM | SIGMA (M4655-500 mL) |
| | 10% FBS | SIGMA (172012-500 mL) |
| | 1 mM Sodium Pyruvate | Thermo Fischer Scientific (11360-070) |
| | 0.1 mM MEM NEAA | Thermo Fischer Scientific (11140-050) |
| CW-2 | RPMI-1640 | SIGMA (R8758-500 mL) |
| | 10% FBS | SIGMA (172012-500 mL) |
| COLO-684 | RPMI-1640 | SIGMA (R8758-500 mL) |
| | 10% FBS | SIGMA (172012-500 mL) |
| GSU | RPMI-1640 | SIGMA (R8758-500 mL) |
| | 10% FBS | SIGMA (172012-500 mL) |
| HT-29 | McCoy's 5A | SIGMA (R8403-500 mL) |
| | 10% FBS | SIGMA (172012-500 mL) |
| NCI-H716 | RPMI-1640 | SIGMA (R8758-500 mL) |
| | 10% FBS | SIGMA (172012-500 mL) |
| | 1 mM Sodium Pyruvate | Thermo Fischer Scientific (11360-070) |
| | 10 mM HEPES | SIGMA (H0887-100 mL) |
| | 0.45% D-Glucose | SIGMA (G8769-500 mL) |

TABLE 3

| Cell line | Cell density (cells/mL) | Seeding density (cells/well) |
|---|---|---|
| HCT 116 | 15000 | 1500 |
| KM12 | 20000 | 2000 |
| RL95-2 | 50000 | 5000 |
| SNU-1 | 20000 | 2000 |
| SW48 | 50000 | 5000 |
| C-33A | 20000 | 2000 |
| CW-2 | 50000 | 5000 |
| COLO-684 | 30000 | 3000 |
| GSU | 30000 | 3000 |
| HT-29 | 15000 | 1500 |
| NCI-H716 | 50000 | 5000 |

2. Results

As shown in FIG. 1, all of the seven cancer cell lines having at least one of TTK mutation and RAD 50 mutation had a markedly low cell survival rate of 70% or less (in particular, 40% or less in FIG. 1) in the test for suppression of expression of WRN. For other cancer cell lines subjected to the test, similarly the cancer cell lines having at least one of TTK mutation and RAD 50 mutation had a markedly low cell survival rate. These results showed that the survival of a cancer cell line having at least one mutation selected from the group (first group) consisting of TTK mutation and RAD 50 mutation highly depended on the function of helicase, and it was revealed that in these cancer cells, suppression of expression of helicase resulted in marked suppression of growth of the cancer cells.

Test Example 2

1. Experimental Material and Method
(1) Cell Line

Further, for about 200 cancer cell lines including the about 70 cancer cell lines described above, expression of WRN was suppressed by siRNA, and cell lines in which suppression of growth was confirmed and cell lines in which growth was not suppressed were selected. In the following test, an example is shown in which as some of the selected cell lines, HCT 116, KM 12, LS 411N, SNU-407, SNU-C 5, RKO, CW-2, CCK-81 and HT-29 (bowel cancer), RL 95-2, AN 3, CA, C-33A, SIHA and JHUEM-3 (uterus cancer), IM 95 and MKN 1 (stomach cancer) and TOV-21G and PA-1 (ovary cancer) were used as the following cancer cell lines to be tested.

HCT 116 is a cancer cell line having mutations (truncating mutations) in at least DNA 2 in addition to the TTK, RAD

38 cancer cell lines having no mutation in any of TTK, RAD 50, MRE 11, NBN, DNA 2, RBBP 8, EXO 1, RPA 1, RPA 2 and RPA 3. Table 4 below shows these cancer cell lines, origin tissues thereof, and information of the presence or absence of truncating mutations in RAD 50, MRE 11, NBN, DNA 2, RBBP 8, EXO 1, RPA 1 and RPA 3.

The mutations shown in Table 4 are mutations each disclosed in the cancer cell line database: "Cancer Cell Line Encyclopedia (CCLE)" prepared by Broad Institute. In Table 4, "N. I." means that information about truncating mutations which cause at least loss-of-function mutations is not known.

TABLE 4

| Cell line | Tissue | RAD50 | MRE11 | NBN | DNA2 | RBBP8 | EXO1 | RPA1 | RPA3 |
|---|---|---|---|---|---|---|---|---|---|
| HCT 116 | Colorectal | Truncating mutation | N.I. | N.I. | Truncating mutation | N.I. | N.I. | N.I. | N.I. |
| KM12 | Colorectal | Truncating mutation | N.I. | N.I. | Truncating mutation | Truncating mutation | Truncating mutation | N.I. | N.I. |
| RL95-2 | Uterus | Truncating mutation | N.I. | N.I. | Truncating mutation | N.I. | N.I. | N.I. | N.I. |
| LS411N | Colorectal | N.I. | Truncating mutation | N.I. | Truncating mutation | Truncating mutation | Truncating mutation | N.I. | N.I. |
| SNU-407 | Colorectal | N.I. | N.I. | N.I. | Truncating mutation | Truncating mutation | Truncating mutation | N.I. | N.I. |
| AN3 CA | Uterus | N.I. | N.I. | N.I. | Truncating mutation | N.I. | N.I. | N.I. | N.I. |
| C-33A | Uterus | Truncating mutation | N.I. | N.I. | Truncating mutation | N.I. | N.I. | Truncating mutation | N.I. |
| SNU-C5 | Colorectal | Truncating mutation | N.I. | N.I. | N.I. | N.I. | N.I. | N.I. | N.I. |
| RKO | Colorectal | Truncating mutation | N.I. | N.I. | N.I. | N.I. | N.I. | N.I. | Truncating mutation |
| CW-2 | Colorectal | Truncating mutation | N.I. | N.I. | N.I. | N.I. | N.I. | Truncating mutation | N.I. |
| CCK-81 | Colorectal | N.I. | N.I. | N.I. | N.I. | Truncating mutation | N.I. | N.I. | N.I. |
| TOV-21G | Ovary | N.I. | N.I. | Truncating mutation | N.I. | N.I. | N.I. | N.I. | N.I. |
| IM95 | Stomach | Truncating mutation | N.I. | Truncating mutation | Truncating mutation | Truncating mutation | N.I. | N.I. | N.I. |
| PA-1 | Ovary | N.I. | N.I. | N.I. | N.I. | N.I. | N.I. | N.I. | N.I. |
| MKN1 | Stomach | N.I. | N.I. | N.I. | N.I. | N.I. | N.I. | N.I. | N.I. |
| SIHA | Uterus | N.I. | N.I. | N.I. | N.I. | N.I. | N.I. | N.I. | N.I. |
| JHUEM-3 | Uterus | N.I. | N.I. | N.I. | N.I. | N.I. | N.I. | N.I. | N.I. |
| HT-29 | colorectal | N.I. | N.I. | N.I. | N.I. | N.I. | N.I. | N.I. | N.I. |

50 and MSH 3. KM 12 is a cancer cell line having mutations (truncating mutations) in at least DNA 2, RBBP 8 and EXO 1 in addition to the TTK and RAD 50. LS 411N is a cancer cell line having mutations (truncating mutations) in at least MRE 11, DNA 2, RBBP 8 and EXO 1. SNU-407 is a cancer cell line having mutations (truncating mutations) in at least DNA 2, RBBP 8 and EXO 1. SNU-C 5 is a cancer cell line having mutations (truncating mutations) in at least RAD 50. PKO is a cancer cell line having mutations (truncating mutations) in at least RAD 50 and RPA 3. CW-2 is a cancer cell line having mutations (truncating mutations) in at least RPA 1 in addition to the RAD 50. CCK-81 is a cancer cell line having mutations (truncating mutations) in at least RBBP 8. RL 95-2 is a cancer cell line having mutations (truncating mutations) in at least DNA 2 in addition to the RAD 50. AN 3 CA is a cancer cell line having mutations (truncating mutations) in at least DNA 2. C-33A is a cancer cell line having mutations (truncating mutations) in at least DNA 2 and RPA 1 in addition to the RAD 50. IM 95 is a cancer cell line having mutations (truncating mutations) in at least RAD 50, NBN, DNA 2 and RBBP 8. TOV-21G is a cancer cell line having mutations (truncating mutations) in at least NBN. HT-29, SIHA, JHUEM-3, MKN 1 and PA-1 are (2) Small Interfering (si)RNA For suppression of expression of WRN, ON-TARGETplus Individual siRNA (manufactured by Dharmacon, Inc.) was used. For transfection, Lipofectamine RNAiMAX (manufactured by Invitrogen Corporation) was used. WRN siRNA (WRN siRNA 1, Dharmacon, Inc. product code: J-010378-06, SEQ ID NO: 25) was used as a test substance, and non-target siRNA 1 (Dharmacon, Inc. product code: J-001810-01, SEQ ID NO: 26) or non-target siRNA (non-target siRNA 2, Dharmacon, Inc. product code: D-001810-03, SEQ ID NO: 27) was used as a negative control. Each siRNA was dissolved using a 1×siRNA buffer obtained by diluting a 5×siRNA buffer (manufactured by Dharmacon: B-002000-UB-100) by 5 times with nuclease free water (AM 9932 manufactured by Ambion, Inc.).

(3) Test for Suppression of Expression of WRN

In each cancer cell line, cytotoxic activity under suppression of expression of WRN was evaluated. The cell lines were cultured in a cell culture flask (430641U manufactured by Corning Incorporated) using the culture solutions shown in Table 5 below, the cell surfaces were washed with PBS (14249-24 manufactured by nacalai tesque), trypsin (35554-64 manufactured by nacalai tesque) was then added, and the cells were incubated at 37° C. for 5 minutes, and suspended with the culture solutions. The number of cells was measured using an automatic cell counter (NC-200 manufactured by Chemometec) and Via 1-Casette (941-0011 manufactured by Chemometec), and the cells then were seeded on a 96-well plate (manufactured by Greiner Bio-One GmbH) at 100 μL/well in such a manner that the number of cells coincided with the seeding density shown in Table 6 below.

Subsequently, for HCT 116, KM 12, LS 411 N, SNU-407, SNU-C 5, RKO, CW-2, CCK-81, HT-29, RL 95-2, AN 3 CA, C-33A, SIHA, JHUEM-3, IM 95 and TOV-21G, Lipofectamine RNAiMAX (13778150 manufactured by Thermo Fischer Scientific) was diluted by 50 times with Opti-Mem (31985-062 manufactured by Thermo Fischer Scientific), and then mixed with the equivalent amount of a 120 nM test substance (WRN siRNA 1) or non-target siRNA (non-target siRNA 1). The mixed solution was added at 20 μL/well to the plate on which the cells were seeded, the plate was then shaken, and the cells were each transfected with siRNA at a final concentration of 10 nM. For MKN 1 and PA-1, Lipofectamine RNAiMAX (13778150 manufactured by Thermo Fischer Scientific) was diluted by 50 times with Opti-Mem (31985-062 manufactured by Thermo Fischer Scientific), and then mixed with the equivalent amount of a 12 nM test substance (WRN siRNA 1) or non-target siRNA (non-target siRNA 2). The mixed solution was added at 20 μL/well to the plate on which the cells were seeded, and the plate was then shaken to transfect the cells with siRNA at a final concentration of 1 nM.

Figure 2:
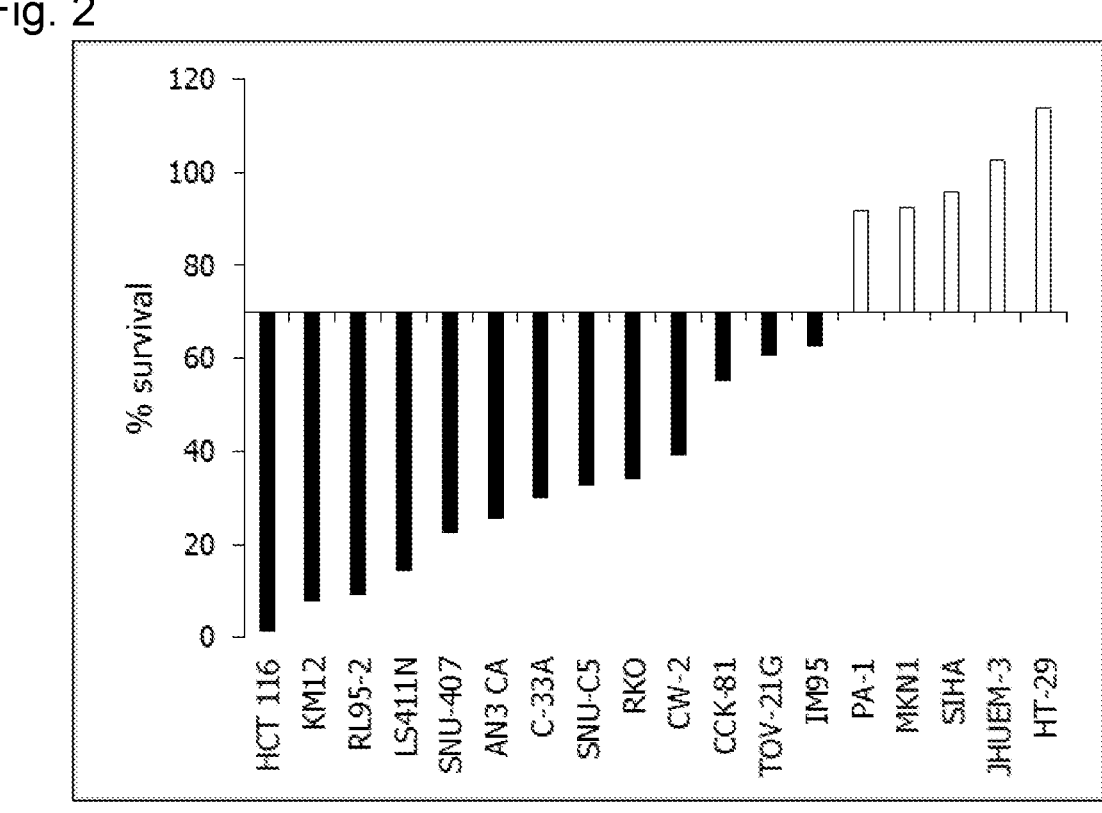
FIG. 2 is a graph showing cell survival rate under suppression of expression of WRN in a cancer cell line in Test Example 2.

The cells were cultured in an incubator at 37° C. for 7 days, Cell Titer-Glo 2.0 Cell Viability Assay (G 9243 manufactured by Promega Corporation) was then added at 20 μL/well, the cells were incubated at room temperature for 5 minutes, and luminescence was then measured with EnVision (manufactured by PerkinElmer) to determine the intracellular ATP level which is a marker for cell survival. The cell survival rate under suppression of expression of WRN was calculated, where the intracellular ATP level in each cancer cell line transfected with the negative control and cultured for 7 days was defined as 100%. FIG. 2 shows the cell survival rate (% survival) under suppression of expression of WRN in each cancer cell line.

TABLE 5

| Cell line | Composition | Culture solution Name of vendor (product code) |
|---|---|---|
| HCT 116 | McCoy's 5A | SIGMA (R8403-500 mL) |
| | 10% FBS | SIGMA (172912-500 mL) |
| KM12 | RPMI-1640 | SIGMA (R8758-500 mL) |
| | 10% FBS | SIGMA (172912-500 mL) |
| LS411N | RPMI-1640 | SIGMA (R8758-500 mL) |
| | 10% FBS | NICHIREI, 174012-18C00A |
| | 10 mM HEPES | SIGMA (H0887-100 mL) |
| | 1 mM Sodium Pyruvate | Thermo Fishcer Scientific (11140-070) |
| | 4.5 g/L D-glucose | SIGMA (G8769-500 mL) |
| SNU-407 | RPMI-1640 | SIGMA (R8758-500 mL) |
| | 10% FBS | SIGMA (172912-500 mL) |
| SNU-C5 | RPMI-1640 | SIGMA (R8758-500 mL) |
| | 10% FBS | SIGMA (172912-500 mL) |
| RKO | E-MEM | SIGMA (M4655-500 mL) |
| | 10% FBS | SIGMA (172912-500 mL) |
| | 0.1 mM NEAA | Thermo Fishcer Scientific (11140-050) |
| | 1 mM Sodium Pyruvate | Thermo Fishcer Scientific (11140-070) |
| CW-2 | RPMI-1640 | SIGMA (R8758-500 mL) |
| | 10% FBS | SIGMA (172912-500 mL) |
| CCK-81 | E-MEM | SIGMA (M4655-500 mL) |
| | 10% FBS | SIGMA (172912-500 mL) |
| HT-29 | McCoy's 5A | SIGMA (R8403-500 mL) |
| | 10% FBS | SIGMA (172912-500 mL) |
| RL95-2 | D-MEM:Ham's F-12 = 1:1 | Thermo Fishcer Scientific (11330-032) |
| | 10% FBS | SIGMA (172912-500 mL) |
| | 5 ug/mL Human insulin | Thermo Fishcer Scientific (12585-014) |
| AN3 CA | E-MEM | SIGMA (M4655-500 mL) |
| | 10% FBS | SIGMA (172912-500 mL) |
| | 0.1 mM NEAA | Thermo Fishcer Scientific (11140-050) |
| | 1 mM Sodium Pyruvate | Thermo Fishcer Scientific (11140-070) |
| C-33A | E-MEM | SIGMA (M4655-500 mL) |
| | 10% FBS | SIGMA (172912-500 mL) |
| | 0.1 mM NEAA | Thermo Fishcer Scientific (11140-050) |
| | 1 mM Sodium Pyruvate | Thermo Fishcer Scientific (11140-070) |
| SIHA | E-MEM | SIGMA (M4655-500 mL) |
| | 10% FBS | NICHIREI, 174012-18C00A |
| JHUEM-3 | D-MEM:Ham's F-12 = 1:1 | Thermo Fishcer Scientific (11330-032) |
| | 10% FBS | NICHIREI, 174012-18C00A |
| | 0.1 mM NEAA | Thermo Fishcer Scientific (11140-050) |
| IM95 | D-MEM (high glucose) | SIGMA (D5796-500 mL) |
| | 10% FBS | SIGMA (172912-500 mL) |
| | 10 μg/mL Insulin | Thermo Fishcer Scientific (12585-014) |
| MKN1 | RPMI-1640 | SIGMA (R8758-500 mL) |
| | 10% FBS | NICHIREI, 174012-18C00A |

TABLE 5-continued

| | Culture solution | |
|---|---|---|
| Cell line | Composition | Name of vendor (product code) |
| TOV-21G | MCDB105:Medium 199 = 1:1 | SIGMA (M6395-1L), SIGMA (M4530-1L) |
| | 15% FBS | SIGMA (172912-500 mL) |
| | 0.75 g/L sodium bicarbonate | Thermo Fishcer Scientific (25080094) |
| PA-1 | E-MEM | SIGMA (M4655-500 mL) |
| | 10% FBS | NICHIREI, 174012-18C00A |
| | 0.1 mM NEAA | Thermo Fishcer Scientific (11140-050) |

TABLE 6

| Cell line | Cell density (cells/mL) | Seeding density (cells/well) |
|---|---|---|
| HCT 116 | 15000 | 1500 |
| KM12 | 20000 | 2000 |
| LS411N | 30000 | 3000 |
| SNU-407 | 20000 | 2000 |
| SNU-C5 | 20000 | 2000 |
| RKO | 10000 | 1000 |
| CW-2 | 50000 | 5000 |
| CCK-81 | 20000 | 2000 |
| HT-29 | 15000 | 1500 |
| RL95-2 | 50000 | 5000 |
| AN3 CA | 30000 | 3000 |
| C-33A | 20000 | 2000 |
| SIHA | 20000 | 2000 |
| JHUEM-3 | 40000 | 4000 |
| IM95 | 30000 | 3000 |
| MKN1 | 10000 | 1000 |
| TOV-21G | 20000 | 2000 |
| PA-1 | 5000 | 500 |

2. Results

As shown in FIG. 2, all of the thirteen cancer cell lines having at least one of RAD 50 mutation, MRE 11 mutation, NBN mutation, DNA 2 mutation and RBBP 8 mutation, particularly at least one of RAD 50 mutation, NBN mutation, DNA 2 mutation and RBBP 8 mutation, had a low cell survival rate of 70% or less in the test for suppression of expression of WRN. For other cancer cell lines subjected to the test, similarly the cancer cell lines having at least one of RAD 50 mutation, MRE 11 mutation, NBN mutation, DNA 2 mutation and RBBP 8 mutation had a markedly low cell survival rate. These results showed that the survival of a cancer cell line having at least one mutation selected from the group (second group) consisting of RAD 50 mutation, MRE 11 mutation, NBN mutation, DNA 2 mutation and RBBP 8 mutation highly depended on the function of helicase, and it was revealed that when in these cancer cells, expression of helicase was suppressed, growth of the cancer cells was markedly suppressed.

Test Example 3

1. Experimental Material and Method
(1) Cell Line

HCT 116 was used as a cancer cell line to be tested. HCT 116 is a cancer cell line having mutations (truncating mutations) in at least TTK, RAD 50, MSH 3 and DNA 2 as described above.

(2) Small Interfering (si)RNA

For suppression of expression of WRN, ON-TAR-GETplus Individual siRNA (manufactured by Dharmacon, Inc.) was used. For transfection, Lipofectamine RNAiMAX (manufactured by Invitrogen Corporation) was used. As siRNA, WRN siRNA (WRN siRNA 2, Dharmacon, Inc.

product code: J-010378-07, SEQ ID NO: 28) was used. siRNA was dissolved using a 1×siRNA buffer obtained by diluting a 5×siRNA buffer (manufactured by Dharmacon: B-002000-UB-100) by 5 times with nuclease free water (AM 9932 manufactured by Ambion, Inc.).

(3) Transfection

For overexpression of WRN, ViaFect Transfection Reagent (manufactured by Promega Corporation) was used. A plasmid in which a siRNA-resistant wild-type WRN gene (SEQ ID NO: 29) is cloned into a pCMV-3Tag-1a vector was used as a control substance, a plasmid in which a typical nucleotide sequence (SEQ ID NO: 1) of genome DNA encoding the human-derived natural WRN as a siRNA-non-resistant wild-type WRN gene is cloned into a pCMV-3Tag-1a vector was used as a test substance 1, and a plasmid in which a siRNA-resistant K 577MWRN gene (K 577MWRN, SEQ ID NO: 30) containing K 577M mutation and lacking helicase activity is cloned into a pCMV-3Tag-1a vector was used as a test substance 2.

(4) Test for Rescue of WRN

In the HCT 116 cancer cell line, cytotoxic activity was evaluated when the siRNA-resistant wild-type WRN gene or the siRNA-non-resistant wild-type WRN gene or the siRNA-resistant K 577MWRN gene was overexpressed while expression of WRN was suppressed. First, the HCT 116 cell line was cultured in a cell culture flask (430641U manufactured by Corning Incorporated) using the culture solutions shown in Table 2 above, the cell surfaces were washed with PBS (14249-24 manufactured by nacalai tesque), trypsin (35554-64 manufactured by nacalai tesque) was then added, and the cells were incubated at 37° C. for 5 minutes, and suspended with the culture solution. The number of cells was measured using an automatic cell counter (NC-200 manufactured by Chemometec) and Via 1-Casette (941-0011 manufactured by Chemometec), the cell density was then adjusted to 7500 cells/76 μL for each culture solution, and the culture solution was seeded at 76 μL/well.

Subsequently, Opti-Mem (31985-062 manufactured by Thermo Fischer Scientific) and Lipofectamine RNAiMAX (13778150 manufactured by Thermo Fischer Scientific) were mixed in such a manner that the final concentration of siRNA (WRN siRNA 2) was 5 nM and the Lipofectamine RNAiMAX was diluted by 100 times. The mixed solution was incubated at room temperature for 20 minutes, and then added at 19 μL/well to the plate on which the cells were seeded, and the plate was shaken to transfect the cells with siRNA at a final concentration of 1 nM.

On the following day, 0.1 μg of the control substance (plasmid of siRNA-resistant wild-type WRN gene), the test substance 1 (plasmid of siRNA-non-resistant wild-type WRN gene) or the test substance 2 (plasmid of siRNA-resistant K 577MWRN gene) and 0.3 μL of ViaFect Transfection Reagent were mixed with 10 μL of Opti-MeM. The mixed solution was incubated at room temperature for 20 minutes, and then added at 10 μL/well to the wells transfected with the siRNA, and the plate was shaken to overexpress the siRNA-resistant wild-type WRN gene, the siRNA-non-resistant wild-type WRN gene or the siRNA-resistant K 577 MWRN gene.

Figure 3:
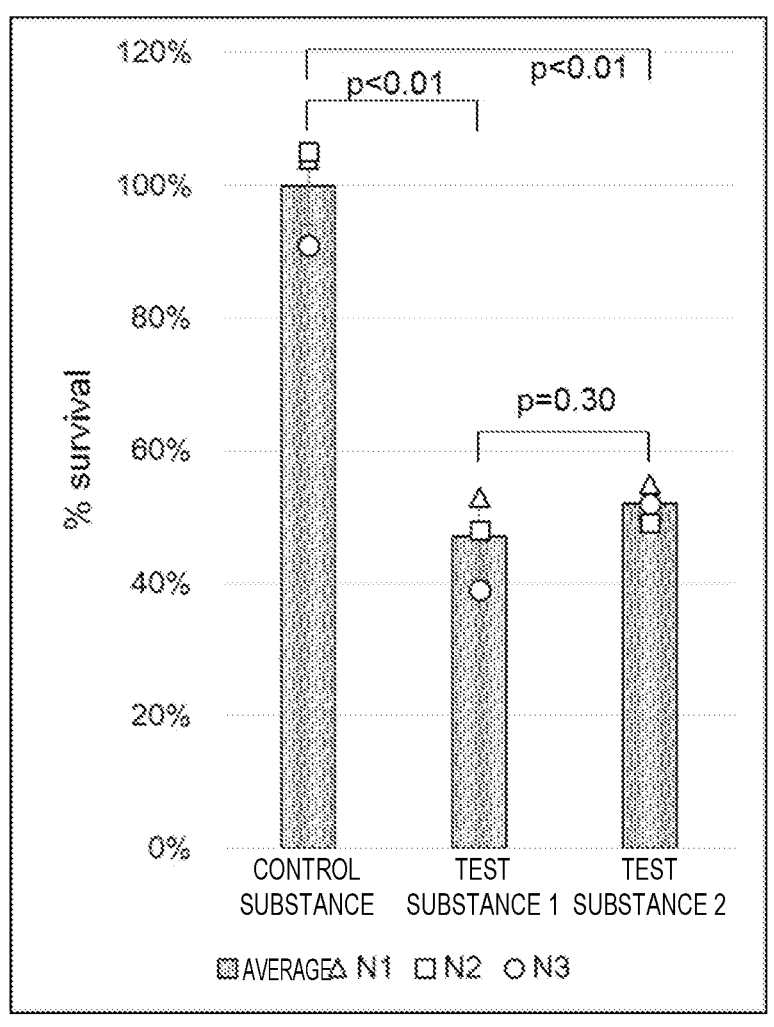
FIG. 3 is a graph showing cell survival rate under suppression of expression of WRN in a cancer cell line in Test Example 3.

The cells were cultured in an incubator at 37° C. for 6 days, Cell Titer-Glo 2.0 Cell Viability Assay (G 9243 manufactured by Promega Corporation) was then added at 50 μL/well, the cells were incubated at room temperature for 5 minutes, luminescence was then measured with EnVision (manufactured by PerkinElmer) to determine the intracellular ATP level which is a marker for cell survival, and the average thereof was calculated (n=3 (N1, N2 and N3)). The cell survival rate under suppression of expression of WRN was calculated, where the intracellular ATP level in each cancer cell line transfected with the control substance and cultured for 6 days was defined as 100%. FIG. 3 shows cell survival rates (% survival) when the cancer cell lines are transfected with the control substance, the test substance 1 or the test substance 2. A T-test was conducted between the control substance and the test substance 1 or 2 and between the test substance 1 and the test substance 2. It was determined that there was a significant difference when p<0.01 as a result of the T-test.

2. Results

As shown in FIG. 3, there was a significant difference between the control substance (cell line transfected with the plasmid of siRNA-resistant wild-type WRN gene) and the test substance 1 (cell line transfected with the plasmid of siRNA-non-resistant wild-type WRN gene) or the test substance 2 (cell line transfected with the plasmid of siRNA-resistant K 577MWRN gene), and there was no significant difference between the test substance 1 and the test substance 2. These results and the results from Test Examples 1 and 2 above showed that evidently, the survival of cancer cells having at least the above-described mutation highly depended on the function of helicase of WRN, and it was shown that in such cancer cells, suppression of expression of helicase resulted in marked suppression of growth of the cancer cells.

INDUSTRIAL APPLICABILITY

As described above, according to the present invention, it is possible to efficiently predict sensitivity to cancer treatment with a helicase inhibitor using at least one mutation selected from the first group consisting of TTK mutation and RAD 50 mutation and/or at least one mutation selected from the second group consisting of RAD 50 mutation, MRE 11 mutation, NBN mutation, DNA 2 mutation and RBBP 8 mutation as an indicator. In addition, according to the present invention, it is possible to detect the presence or absence of the mutation in a cancer patient-derived sample and select a patient having the mutation detected, followed by subjecting the patient to treatment of cancer with a helicase inhibitor. This enables significant improvement of cancer treatment outcomes. In addition, it is possible to efficiently perform companion diagnosis by detection of the presence or absence of the mutation by using an oligonucleotide probe or primer against at least one gene selected from the first group consisting of TTK and RAD 50 and/or at least one gene selected from the second group consisting of RAD 50, MRE 11, NBN, DNA 2 and RBBP 8, and an antibody against at least one protein selected from the first group consisting of TTK protein and RAD 50 protein and/or at least one protein selected from the second group consisting of RAD 50 protein, MRE 11 protein, NBS 1 protein, DNA 2 protein and CtIP protein.

The invention claimed is:

1. A method for treating cancer, the method comprising:
   (a) providing, or having provided, a sample comprising cancer cells from a cancer patient;
   (b) detecting, or having detected, the presence in the cancer cells of at least one mutation selected from an RAD 50 loss-of-function mutation, an MRE 11 loss-of-function mutation, an NBN loss-of-function mutation, a DNA 2 loss-of-function mutation, and an RBBP 8 loss-of-function mutation; and (c) administering a WRN inhibitor to the patient, thereby treating the patient's cancer.

2. The method of claim 1, wherein step (b) further comprises detecting, or having detected, the presence in the cancer cells of at least one of the following mutations: an EXO 1 loss-of-function mutation, an RPA 1 loss-of-function mutation, an RPA 2 loss-of-function mutation, and an RPA 3 loss-of-function mutation.

* * * * *